United States Patent [19]

Katagiri et al.

[11] Patent Number: 4,629,670
[45] Date of Patent: Dec. 16, 1986

[54] PHOTOCONDUCTIVE FILM OF AZULENIUM SALT AND ELECTROPHOTOGRAPHIC PHOTOSENSITIVE MEMBER

[75] Inventors: Kazuharu Katagiri, Tama; Yoshihiro Oguchi, Yokohama; Takeshi Ohtake, Fujisawa; Kozo Arao, Tokyo; Yoshio Takasu, Tama, all of Japan

[73] Assignee: Canon Kabushiki Kaisha, Tokyo, Japan

[21] Appl. No.: 742,570

[22] Filed: Jun. 7, 1985

[30] Foreign Application Priority Data

| Jun. 12, 1984 | [JP] | Japan | 59-120128 |
| Jun. 30, 1984 | [JP] | Japan | 59-134117 |
| Jun. 30, 1984 | [JP] | Japan | 59-134118 |
| Jun. 30, 1984 | [JP] | Japan | 59-134120 |
| Jun. 30, 1984 | [JP] | Japan | 59-134121 |
| Jun. 30, 1984 | [JP] | Japan | 59-134122 |

[51] Int. Cl.$^4$ .......................... G03G 5/00; G03G 5/09; G03G 5/14

[52] U.S. Cl. ................................. 430/58; 430/59; 430/72; 430/73; 430/74; 430/75; 430/76; 430/78; 430/83; 430/90; 430/91; 430/95; 430/945

[58] Field of Search ............... 430/58, 59, 72, 73, 430/74, 75, 76, 78, 83, 90, 91, 95

[56] References Cited

U.S. PATENT DOCUMENTS

| 4,548,886 | 10/1985 | Katagini et al. | 430/57 X |
| 4,565,761 | 1/1986 | Katagini et al. | 430/75 X |
| 4,579,799 | 4/1986 | Katagini et al. | 430/58 |

FOREIGN PATENT DOCUMENTS

| 59-146060 | 8/1984 | Japan | 430/72 |
| 59-149369 | 8/1984 | Japan | 430/72 |
| 59-162556 | 9/1984 | Japan | 430/58 |
| 59-191059 | 10/1984 | Japan | 430/72 |

*Primary Examiner*—Roland E. Martin
*Attorney, Agent, or Firm*—Fitzpatrick, Cella, Harper & Scinto

[57] ABSTRACT

Photoconductive films contain specified azulenium salt compounds. Electrophotographic photosensitive members are provided with a photoconductive film containing at least one of the specified azulenium salt compounds.

20 Claims, No Drawings

PHOTOCONDUCTIVE FILM OF AZULENIUM SALT AND ELECTROPHOTOGRAPHIC PHOTOSENSITIVE MEMBER

BACKGROUND OF THE INVENTION

1. Field of the Invention

This invention relates to a novel photoconductive film and an electrophotographic photosensitive member of high sensitivity using said photoconductive film.

2. Description of the Prior Art

Heretofore, there have been disclosed pigments and dyes exhibiting photoconductivity in many literatures. For example, RCA Review, Vol. 23, pp. 413–419 (1962.9) disclosed photoconductivity of a phthalocyanine pigment, and U.S. Pat. Nos. 3397086 and 3816118 discloses an electrophotographic photosensitive member employing a phthalocyanine pigment. Further, as an organic semiconductor used in an electrophotographic photosensitive member, there is mentioned, for example, a pyrylium type dye disclosed in U.S. Pat. Nos. 4,315,983 and 4,327,169 and "Research Disclosure" 20517 (1981.5), a methine sequaric acid dye disclosed in U.S. Pat. No. 3,824,099, a disazo pigment disclosed in U.S. Pat. Nos. 3,898,084 and 4,251,613, or the like.

Such organic semiconductors can be prepared easily as compared with inorganic semiconductors, and also can be prepared as compounds having photoconductivity sensitive to a light of a desired wavelength range. Electrophotographic photosensitive members constituted of such an organic semiconductor film formed on a conductive substrate have advantageously good color sensitivity. However, there are only a few organic semiconductors having practically good sensitivity and durability. In particular, as the result of recent development of low power semiconductor laser, there are actively developed organic semiconductors of a high sensitivity characteristics as to long wavelength lights such as those of 700 nm or more, but compounds having a large light absorbing coefficient as to long wavelength lights are, in general, thermally unstable and are liable to be decomposed due to even a slight temperature rise. Therefore, electrophotographic photosensitive members sensitive to infrared ray are practically difficult to be produced.

SUMMARY OF THE INVENTION

An object of the present invention is to provide a novel organic semiconductor.

Another object of the present invention is to provide a photoconductive film composed of the novel organic semiconductor.

A further object of the present invention is to provide an electrophotographic photosensitive member employing the novel photoconductive film.

Still another object of the present invention is to provide an electrophotographic photosensitive member suitable for an electrophotographic copying machine.

A still further object of the present invention is to provide an electrophotographic photosensitive member suitable for a laser-beam-scanning electrophotographic printer.

Still another object of the present invention is to provide an electrophotographic photosensitive member highly sensitive to rays of long wavelengths.

According to one aspect of the present invention, there is provided a photoconductive film which comprises at least one of azulenium salt compounds represented by formulae (1)–(9) as shown below;

General formula

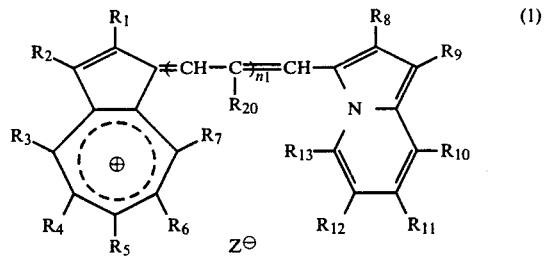

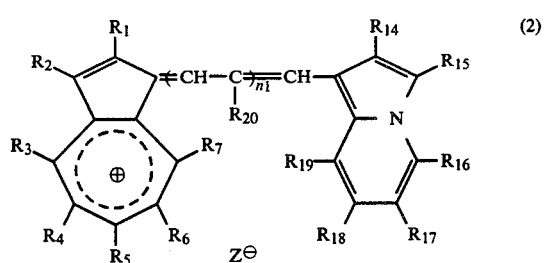

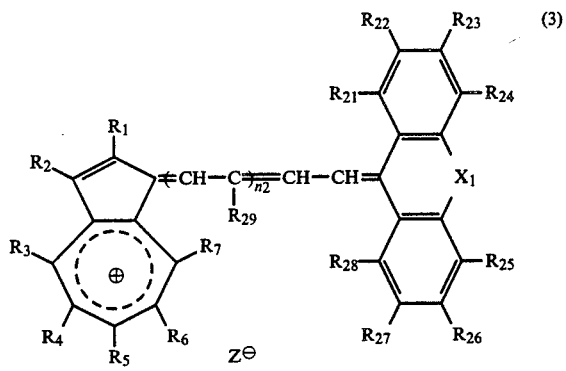

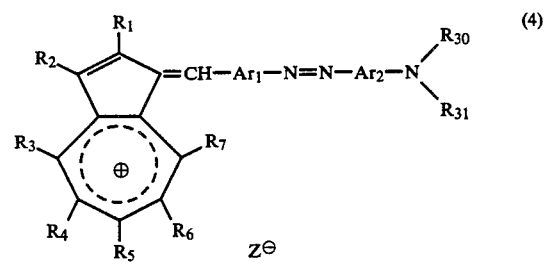

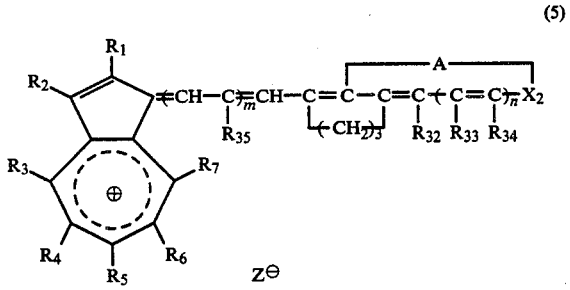

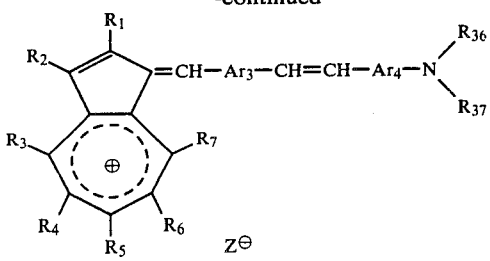

(6)

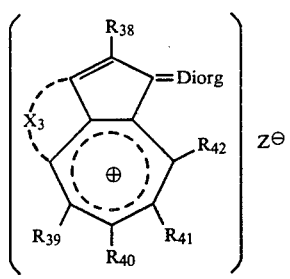

(7)

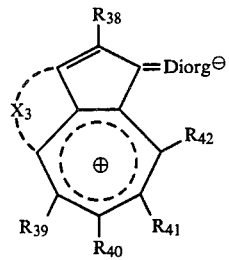

(8)

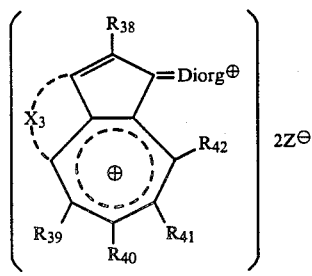

(9)

wherein
each of $R_1$, $R_2$, $R_3$, $R_4$, $R_5$, $R_6$ and $R_7$ is hydrogen, halogen, or an organic monovalent residue and at least one of the combinations ($R_1$ and $R_2$), ($R_2$ and $R_3$), ($R_3$ and $R_4$), ($R_4$ and $R_5$), ($R_5$ and $R_6$), and ($R_6$ and $R_7$) may form a substituted or unsubstitued condensed ring;

each of $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ is hydrogen, halogen, alkyl, alkoxy, substituted or unsubstituted aryl, substituted or unsubstituted aralkyl, nitro, or acyl where at least one of the combinations ($R_8$ and $R_9$), ($R_9$ and $R_{10}$), ($R_{10}$ and $R_{11}$), ($R_{11}$ and $R_{12}$), ($R_{12}$ and $R_{13}$), ($R_{14}$ and $R_{15}$), ($R_{15}$ and $R_{16}$), ($R_{16}$ and $R_{17}$), ($R_{17}$ and $R_{18}$), and ($R_{18}$ and $R_{19}$) may form a substituted or unsubstituted condensed ring;

$R_{20}$ is hydrogen, nitro, alkyl, or aryl;

$n_1$ is 0, 1, or 2;

each of $R_{21}$, $R_{22}$, $R_{23}$, $R_{24}$, $R_{25}$, $R_{26}$, $R_{27}$, and $R_{28}$ is hydrogen, halogen, alkyl, alkoxy, hydroxyl, substituted or unsubstituted aryl, substituted or unsubstituted aralkyl, or nitro, and at least one of the combinations ($R_{21}$ and $R_{22}$), ($R_{22}$ and $R_{23}$), ($R_{23}$ and $R_{24}$), ($R_{25}$ and $R_{26}$), ($R_{26}$ and $R_{27}$), and ($R_{27}$ and $R_{28}$) may form a substituted or unsubstituted aromatic ring;

$X_1$ is oxygen, sulfur, or selenium;

$R_{29}$ is hydrogen, nitro, cyano, alkyl, or aryl;

$n_2$ is 0, 1, or 2;

each of $R_{30}$ and $R_{31}$ is substituted or unsubstituted alkyl, aryl or aralkyl, and $R_{30}$ and $R_{31}$ may be joined together with the nitrogen atom to which there are attached to form a ring;

each of Ar1 and Ar2 is substituted or unsubstituted arylene;

each of $R_{32}$, $R_{33}$, and $R_{34}$ is hydrogen, alkyl, alkoxy, substituted or unsubstituted aryl, substituted or unsubstituted styryl, substituted or unsubstituted 4-phenyl-1, 3-butadienyl, or a substituted or unsubstituted heterocyclic ring group, and the combination ($R_{32}$ and $R_{33}$) or ($R_{33}$ and $R_{34}$) may form a substituted or unsubstituted benzene ring;

$R_{35}$ is hydrogen, nitro, alkyl, or aryl;

$X_2$ is oxygen, sulfur, or selenium;

A is an atomic group necessary to complete pyran, thiapyran, selenapyran, benzopyran, benzothiapyran, benzoselenapyran, naphthopyran, naphthothiapyran, or naphthoselenapyran which may be substituted;

$m_1$ is 0, 1, or 2;

$m_2$ is 0 or 1;

each of $R_{36}$ and $R_{37}$ is substituted or unsubstituted alkyl, aryl, or aralkyl, and $R_{36}$ and $R_{37}$ may be joined together with the nitrogen atom to which they are attached to form a ring;

each of Ar3 and Ar4 is substituted or unsubstituted arylene;

each of $R_{38}$, $R_{39}$, $R_{40}$, $R_{41}$, and $R_{42}$ is hydrogen, halogen, or an organic monovalent residue;

$X_3$ is an atomic group necessary to form a substituted or unsubstituted 5-, 6- or 7-membered aromatic ring;

at least one of the combinations ($R_{38}$ and an aromatic ring formed by $X_3$), (an aromatic ring formed by $X_3$ and $R_{39}$), ($R_{39}$ and $R_{40}$), ($R_{40}$ and $R_{41}$), and ($R_{41}$ and $R_{42}$) may form a substituted or unsubstituted aromatic ring, heterocyclic ring or aliphatic ring;

Diorg is an organic divalent residue linked with a double bond;

$Z^-$ is an anionic residue.

According to another aspect of the present invention, there is provided an electrophotographic photosensitive member which comprises an electroconductive substrate and an photoconductive film comprising at least one of the azulenium salt compounds represented by the formulae (1)–(9) as shown below;

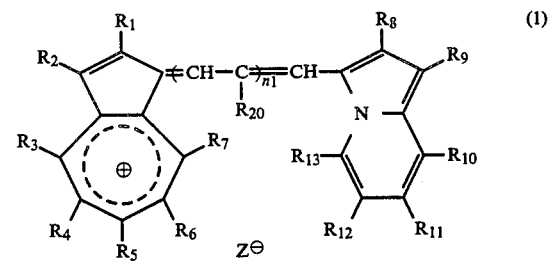

(1)

-continued

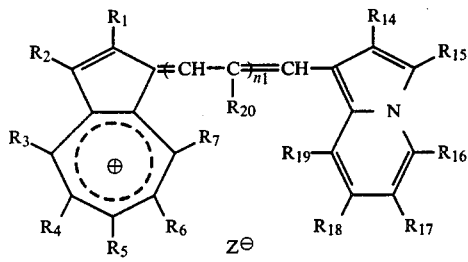 (2)

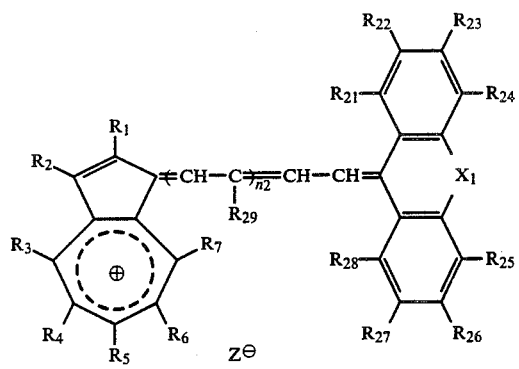 (3)

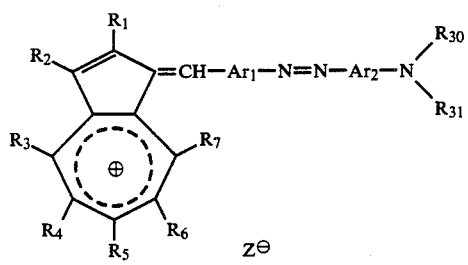 (4)

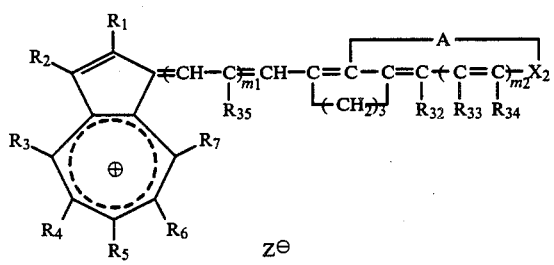 (5)

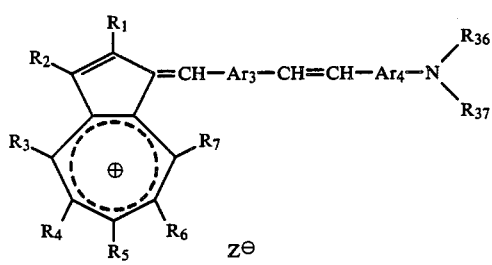 (6)

-continued

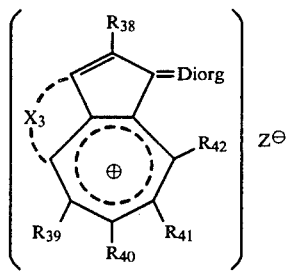 (7)

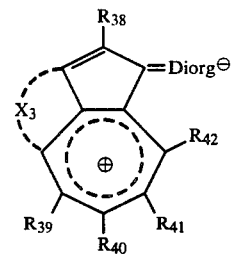 (8)

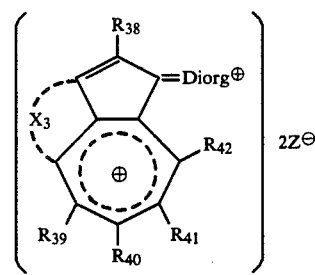 (9)

wherein
each of $R_1$, $R_2$, $R_3$, $R_4$, $R_5$, $R_6$, and $R_7$ is hydrogen, halogen, or an organic monovalent residue and at least one of the combinations ($R_1$ and $R_2$), ($R_2$ and $R_3$), ($R_3$ and $R_4$), ($R_4$ and $R_5$), ($R_5$ and $R_6$), and ($R_6$ and $R_7$) may form a substituted or unsubstituted condensed ring;

each of $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ is hydrogen, halogen, alkyl, alkoxy, substituted or unsubstituted aryl, substituted or unsubstituted aralkyl, nitro, or aryl, and at least one of the combinations ($R_8$ and $R_9$), ($R_9$ and $R_{10}$), ($R_{10}$ and $R_{11}$), ($R_{11}$ and $R_{12}$), ($R_{12}$ and $R_{13}$), ($R_{14}$ and $R_{15}$), ($R_{15}$ and $R_{16}$), ($R_{16}$ and $R_{17}$), ($R_{17}$ and $R_{18}$), and ($R_{18}$ and $R_{19}$) may form a substituted or unsubstituted condensed ring;

$R_{20}$ is hydrogen, nitro, alkyl, or aryl;

$n_1$ is 0, 1, or 2;

each of $R_{21}$, $R_{22}$, $R_{23}$, $R_{24}$, $R_{25}$, $R_{26}$, $R_{27}$, and $R_{28}$ is hydrogen, halogen, alkyl, alkoxy, hydroxyl, substituted or unsubstituted aryl, substituted or unsubstituted aralkyl, or nitro, and at least one of the combinations ($R_{21}$ and $R_{22}$), ($R_{22}$ and $R_{23}$), ($R_{23}$ and $R_{24}$), ($R_{25}$ and $R_{26}$), ($R_{26}$ and $R_{27}$), and ($R_{27}$ and $R_{28}$) may form a substituted or unsubstituted aromatic ring;

$X_1$ is oxygen, sulfur, or selenium;

$R_{29}$ is hydrogen, nitro, cyano, alkyl, or aryl;

$n_2$ is 0, 1, or 2;

each of $R_{30}$ and $R_{31}$ is substituted or unsubstituted alkyl, aryl, or aralkyl, and $R_{30}$ and $R_{31}$ may be joined together with the nitrogen atom to which they are attached to form a ring;

each of Ar1 and Ar2 is substituted or unsubstituted arylene;

each of $R_{32}$, $R_{33}$, and $R_{34}$ is hydrogen, alkyl, alkoxy, substituted or unsubstituted aryl, substituted or unsubstituted styryl, substituted or unsubstituted 4-phenyl-1, 3-butadienyl, or a substituted or unsubstituted heterocyclic ring group, and the combination ($R_{32}$ and $R_{33}$) or ($R_{33}$ and $R_{34}$) may form a substituted or unsubstituted benzene ring;

$R_{35}$ is hydrogen, nitro, alkyl, or aryl;

$X_2$ is oxygen, sulfur, or selenium;

A is an atomic group necessary to complete pyran, thiapyran, selenapyran, benzopyran, benzothiapyran, benzoselenapyran, naphthopyran, naphthothiapyran, or naphthoselenapyran which may be substituted;

$m_1$ is 0, 1, or 2;

$m_2$ is 0 or 1;

each of $R_{36}$ and $R_{37}$ is substituted or unsubstituted alkyl, aryl, or aralkyl, and $R_{36}$ and $R_{37}$ may be joined together with the nitrogen atom to which they are attached to form a ring;

each of Ar3 and Ar4 is substituted or unsubstituted arylene;

each of $R_{38}$, $R_{39}$, $R_{40}$, $R_{41}$, and $R_{42}$ is hydrogen, halogen, or an organic monovalent residue;

$X_3$ is an atomic group necessary to form a substituted or unsubstituted 5-, 6- or 7-membered aromatic ring;

at least one of the combinations ($R_{38}$ and an aromatic ring formed by $X_3$), (an aromatic ring formed by $X_3$ and $R_{39}$), ($R_{39}$ and $R_{40}$), ($R_{40}$ and $R_{41}$), and ($R_{41}$ and $R_{42}$) may form a substituted or unsubstituted aromatic ring, heterocyclic ring or aliphatic ring;

Diorg is an organic divalent residue linked with a double bond;

$Z^-$ is an anionic residue.

DETAILED DESCRIPTION OF THE PREFERRED EMBODIMENTS

In embodiments of the present invention, each of $R_1$ to $R_7$ of the azulenium salt compounds represented by the formulae (1) to (9) represents hydrogen, halogen (chlorine, bromine, or iodine), or an monovalent organic residue. The monovalent organic residue can be selected from a wide variety of groups. Preferred ones among them are alkyl groups (e.g. methyl, ethyl, n-propyl, isopropyl, n-butyl, t-butyl, n-amyl, n-hexyl, n-octyl, 2-ethylhexyl and t-octyl), alkoxy groups (e.g. methoxy, ethoxy, propoxy and butoxy), substituted or unsubstituted aryl groups (e.g. phenyl, tolyl, xylyl, ethylphenyl, methoxyphenyl, ethoxyphenyl), chlorophenyl, nitrophenyl, dimethylaminophenyl, α-naphthyl and β-naphthyl), substituted or unsubstituted heterocyclic groups (e.g. pyridyl, quinolyl, carbazolyl, furyl, thienyl and pyrazolyl), substituted or unsubstituted aralkyl groups (e.g. benzyl, 2-pheylethyl, 2-phenyl-1-methylethyl, bromobenzyl, 2-bromophenylethyl, methylbenzyl, methoxybenzyl and nitrobenzyl), aryl groups (e.g. acetyl, propionyl, butyryl, valeryl, benzoyl, toluoyl, naphtoyl, phthaloyl and furoyl), substituted or unsubstituted amino groups (e.g. amino, dimethylamino, diethylamino, dipropylamino, acetylamino and benzoylamino), substituted or unsubstituted styryl groups (e.g. styryl, dimethylaminostyryl, diethylaminostyryl, dipropylaminostyryl, methoxystyryl, ethoxystyryl and methylstyryl), nitro, hydroxy, merxapto, thioether, carboxyl, carboxylate, carboxamide, cyano, substituted or unsubstituted arylazo groups (e.g. phenylazo, α-naphthylazo, β-naphthylazo, dimethylaminophenylazo, chlorophenylazo, nitrophenylazo, methoxyphenylazo and tolylazo). At least one of the combinations of $R_1$–$R_2$, $R_2$–$R_3$, $R_3$–$R_4$, $R_4$–$R_5$, $R_5$–$R_6$ and $R_6$–$R_7$ can form a substituted or unsubstituted, fused-ring. The fused ring is a 5-, 6- or 7-membered aromatic ring, heterocycle or ring formed by aliphatic chains.

Each of $R_8$, $R_9$, $R_{10}$, $R_{11}$, $R_{12}$, $R_{13}$, $R_{14}$, $R_{15}$, $R_{16}$, $R_{17}$, $R_{18}$ and $R_{19}$ represents hydrogen, halogen (chlorine, bromine or iodine), alkyl group e.g. methyl, ethyl, n-propyl, isopropyl, n-butyl, t-butyl, n-amyl, n-hexyl, n-oxtyl, or 2-ethylhexyl, alkoxy group (e.g. methoxy, ethoxy, propoxy, or botoxy), substituted or unsubstituted aryl group (e.g. phenyl, tolyl, xylyl, ethylphenyl, methoxyphenyl, ethoxyphenyl, chlorophenyl, nitrophenyl, dimethylaminophenyl, α-naphthyl, or β-naphthyl), substituted or unsubstituted aralkyl group (e.g. benzyl, 2-phenylethyl, 2-phenyl-1-methylethyl, bromobenzyl, methylbenzyl, methoxybenzyl, or nitrobenzyl), nitro, or acyl group (e.g. acetyl, propionyl, butyryl, valeryl, benzoyl, toluoyl, naphthoyl, phthaloyl, or furoyl).

At least one of the combinations of $R_8$–$R_9$, $R_9$–$R_{10}$, $R_{10}$–$R_{11}$, $R_{11}$–$R_{12}$, $R_{12}$–$R_{13}$, $R_{13}$–$R_{14}$, $R_{14}$–$R_{15}$, $R_{15}$–$R_{16}$, $R_{16}$–$R_{17}$, $R_{17}$–$R_{18}$ and $R_{18}$–$R_{19}$ can form a 5-, 6- or 7-membered aromatic ring or heterocycle which can be substituted or unsubstituted.

$R_{20}$ represents hydrogen, nitro, cyano, alkyl (e.g. methyl, ethyl, propyl or butyl), or aryl (e.g. phenyl, tolyl or xylyl). $n_1$ is 0, 1 or 2.

Each of $R_{21}$, $R_{22}$, $R_{23}$, $R_{24}$, $R_{25}$, $R_{26}$, $R_{27}$ and $R_{28}$ represents hydrogen, halogen (e.g. chlorine, bromine or iodine), alkyl group (e.g. methyl, ethyl, n-propyl, isopropyl, n-butyl or t-butyl, alkoxy group (e.g. methoxy, ethoxy, propoxy, or butoxy), hydroxy, substituted or unsubstituted aryl group (e.g. phenyl, tolyl, xylyl, ethylphenyl, methoxyphenyl, nitrophenyl, dimethylaminophenyl, α-naphthyl, or β-naphthyl), substituted or unsubstituted aralkyl group (e.g. benzyl, 2-phenylethyl, 2-phenyl-1-methylethyl, bromobenzyl, methylbenzyl, or nitrogenzyl), or nitro.

At least one of the combinations of $R_{21}$–$R_{22}$, $R_{23}$–$R_{24}$, $R_{24}$–$R_{25}$, $R_{26}$–$R_{27}$, and $R_{27}$–$R_{28}$ can form a substituted or unsubstituted aromatic ring. $X_1$ is O, S or Se.

$R_{29}$ represents hydrogen, nitro, cyano, alkyl (e.g. methyl, ethyl, propyl or butyl), or aryl (e.g. phenyl, tolyl or xylyl). $n_2$ is 0, 1 or 2.

$R_{30}$ and $R_{31}$ each is alkyl group (e.g. methyl, ethyl, n-propyl, isopropyl, n-butyl, t-butyl, n-amyl n-hexyl, n-octyl, 2-ethylhexyl, or t-octyl, substituted or unsubstituted aryl group (e.g., phenyl, tolyl, xylyl, ethylphenyl, methoxyphenyl, ethoxyphenyl, chlorophenyl, nitrophenyl, α-naphthyl, or β-naphthyl), or substituted or unsubstituted aralkyl group (e.g. benzyl, 2-phenylethyl, 2-phenyl-1-methylethyl, methylbenzyl, methoxybenzyl, or nitrobenzyl). $R_{30}$ and $R_{31}$ together with the N atom can form a 5- or 6-membered ring (e.g. morpholino, pyrrolidino, piperidinylpiperadino, phenothiazino, phenoxazino, carbazolyl, indolyl, pyrrolyl or pyrazolyl).

Ar1 and Ar2 each is a substituted or unsubstituted arylene group (e.g. phenylene, 1,4-naphthylene, 1,5-naphthylene or 9,10-anthrylene), and the substituents thereof are alkyl groups (e.g. methyl, ethyl, n-propyl, isopropyl, n-butyl, t-butyl, n-hexyl and 2-ethylhexyl), alkoxyl groups (e.g. methoxy, ethoxy, propoxy and butoxy, halogens (e.g. chlorine, bromine and iodine), and the like.

Each of $R_{32}$, $R_{33}$ and $R_{34}$ represents hydrogen, alkyl group (e.g. methyl, ethyl, n-propyl, isopropyl, n-butyl, t-butyl, n-amyl, n-hexyl, n-octyl, 2-ethylhexyl, t-octyl, nonyl or dodecyl), alkoxy group (e.g. methoxy, ethoxy, propoxy, butoxy, amyloxy, hexyloxy, octyloxy), substituted or unsubstituted aryl group (phenyl, tolyl, xylyl, ethylphenyl, methoxyphenyl, chlorophenyl, nitrophenyl, dimethylaminophenyl, dibenzylaminophenyl, α-naphthyl or β-naphthyl), substituted or unsubstituted styryl or 4-phenyl-1,3-butadienyl group (styryl, methoxystyryl, dimethoxystyryl, ethoxystyryl, diethoxystyryl, dimethylaminostyryl, diethylaminostyryl, 4-phenyl-1,3-butadienyl, 4-(p-dimethylaminophenyl)-1,3-butadienyl, or 4-(p-diethylaminophenyl)-1,3-butadienyl), or substituted or unsubstituted heterocyclic group (e.g. 3-carbazolyl, 9-methyl-3-carbozolyl, 9-ethyl-3-carbazolyl or 9-carbazolyl). The respective combinations of $R_{32}$–$R_{33}$ and $R_{33}$–$R_{34}$ can be joined to form a substituted or unsubstituted benzene ring.

$R_{35}$ represents hydrogen, nitro, cyano, alkyl group (e.g. methyl, ethyl, propyl or butyl), or aryl group (e.g. phenyl, tolyl or xylyl).

$X_2$ is S, O or Se.

A represents an atom necessary to complete pyran, thiapyran, selenapyran, benzopyran, benzothiapyran, benzoselenapyran, naphthopyran, naphthothiapyran or naphthoselenapyran. $m_1$ is 0, 1 or 2, and $m_2$ is 0 or 1.

$R_{36}$ and $R_{37}$ each represents alkyl group (e.g. methyl, ethyl, n-propyl, isopropyl, n-butyl, t-butyl, n-amyl, n-hexyl, n-octyl, 2-ethylhexyl, or t-octyl), substituted or unsubstituted aryl group (e.g. phenyl, tolyl, xylyl, ethylphenyl, methoxyphenyl, ethoxyphenyl, chlorophenyl, nitrophenyl, dimethylaminophenyl, α-naphthyl, or β-naphthyl), or substituted or unsubstituted aralkyl group (e.g. benzyl, 2-phenylethyl, 2-phenyl-1-methylethyl, methylbenzyl, methoxybenzyl, or nitrobenzyl).

$R_{36}$ and $R_{37}$ together with a nitrogen atom can form a 5- or 6-membered ring (e.g. morpholino, pyrrolidino, piperidinylpiperadino, phenothiazino, phenoxazino, carbazolyl, indolyl, pyrroly or pyrazolyl).

Each of Ar3 and Ar4 represents a arylene group (e.g. phenylene, 1,4-naphthylene, 1,5-naphthylene, or 9,10-anthrylene). The substituted thereof are alkyl groups (e.g. methyl, ethyl, n-propyl, isopropyl, n-butyl, t-butyl, n-hexyl, and 2-ethykhexyl), alkoxy groups (e.g. methoxy, ethoxy, propoxy and butoxy), and halogens (e.g. chlorine, bromine and iodine).

Each of $R_{38}$ to $R_{42}$ represents hydrogen, halogen (e.g. chlorine, bromine or iodine) or a monovalent organic residue, and $X_3$ represents an atomic group necessary to form a substituted or unsubstituted aromatic ring constituted with 5-, 6- or 7-members. The monovalent organic residue can be selected from a wide variety of groups. Preferred ones thereof are alkyl groups (e.g. methyl, ethyl, n-propyl, isopropyl, n-butyl, t-butyl, n-amyl, n-hexyl, n-octyl, 2-ethylhexyl, and t-octyl), alkoxy groups (e.g. methoxy, ethoxy, propoxy, and butoxy), substituted or unsubstituted aryl groups (e.g. phenyl, tolyl, xylyl, ethylphenyl, methoxyphenyl, ethoxyphenyl, chlorophenyl, nitrophenyl, dimethylaminophenyl, α-naphthyl, and β-naphthyl), substituted or unsubstituted heterocyclic groups (e.g. pyridyl, quinolyl, carbazolyl, furyl, thienyl and pyrazolyl), substituted or unsubstituted aralkyl groups (e.g. benzyl, 2-phenylethyl, 2-phenyl-1-methylethyl, bromobenzyl, 2-bromophenylethyl, methylbenzyl, methoxybenzyl, and nitrobenzyl), acyl groups (e.g. acetyl, propionyl, butyryl, valeryl, benzoyl, toluoyl, naphthoyl, phthaloyl, and furoyl), substituted or unsubstituted amino groups (e.g. amino, dimethylamino, diethylamino, dipropylamino, acetylamino, and benzoylamino), substituted or unsubstituted styryl groups (e.g. styryl, dimethylaminostyryl, diethylaminostyryl, dipropylaminostyryl, methoxystyryl, ethoxystyryl, and methylstyryl), nitro, hydroxyl, mercapto, thioether, carboxyl, carboxylate, carboxamide, cyano, and substituted or unsubstituted arylazo groups (e.g. phenylazo, α-naphthylazo, β-naphthylazo, dimethylaminophenylazo, chlorophenylazo, nitrophenylazo, methoxyphenylazo, and tolylazo).

At least one of the combinations of $R_{38}$-aromatic ring (formed by $X_3$), aromatic ring (formed by $X_3$)—$R_{39}$, $R_{39}$–$R_{40}$, $R_{40}$–$R_{41}$ and $R_{41}$–$R_{42}$ can form a substituted or unsubstituted aromatic ring (e.g. benzene, naphthalene, chlorobenzene, ethylbenzene or methoxybenzene), heterocycle (e.g. furan, benzofuran, pyrrole, thiophene, pyridine or quinoline), or ring formed by aliphatic chains (e.g. dimethylene, trimethylene or tetramethylene). "Diorg" represents a bivalent organic residue linked by a double bond. The embodiments including said "Diorg" of the present invention can be exemplified by the following formulae (10)–(20): wherein $Q^{\oplus}$ represents the following azulenium skeleton, and the right-hand moieties, excluding $Q^{\oplus}$, represent "Diorg".

Azulenium skeleton ($Q^{\oplus}$):

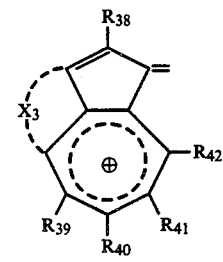

General formula (10):

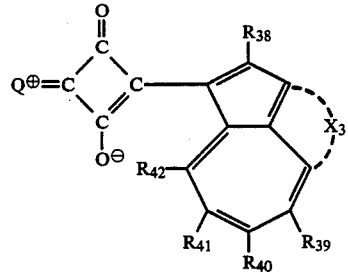

$R_{38}$ to $R_{42}$, and $X_3$ in this formula are as defined above.

General formula (11):

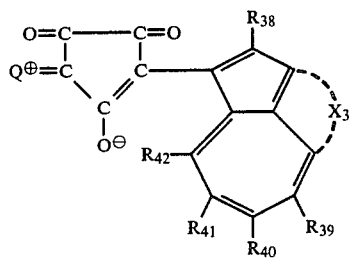

$R_{38}$ to $R_{42}$ and $X_3$ in this formula are as defined above.

General formula (12):

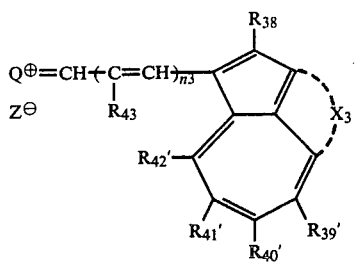

Each of $R_{38}'$ to $R_{42}'$ in this formula represents hydrogen, halogen, (e.g. chlorine, bromine, or iodine), or an organic monovalent residue, and $X_3$ forms an aromatic ring constituted with 5-, 6- or 7-members. The organic monovalent residue can be selected from a variety of radicals. Preferred examples of the organic monovalent residues are alkyl groups (e.g. methyl, ethyl, n-propyl, isopropyl, n-butyl, t-butyl, n-amyl, n-hexyl, n-octyl, 2-ethylhexyl, and t-octyl), alkoxy groups (e.g. methoxy, ethoxy, propoxy, and butoxy), substituted or unsubstituted aryl groups (e.g. phenyl, tolyl, xylyl, ethylphenyl, methoxyphenyl, ethoxyphenyl, chlorophenyl, nitrophenyl, dimethylaminophenyl, α-naphthyl, and β-naphtyl), substituted or unsubstituted heterocyclic groups (e.g. pyridyl, quinolyl, carbazolyl, furyl, thienyl and pyrazolyl), substituted or unsubstituted aralkyl groups (e.g. benzyl, 2-phenylethyl, 2-phenyl-1-methylethyl, bromobenzyl, 2-bromophenylethyl, methylbenzyl, methoxybenzyl, and nitrobenzyl), acyl groups (e.g. acetyl, propionyl, butyryl, valeryl, benzoyl, toluoyl, naphthoyl, phthaloyl, and furoyl), substituted or unsubstituted amino groups (e.g. amino, dimethylamino, diethylamino, dipropylamino, acetylamino, and benzoylamino), substituted or unsubstituted styryl groups (e.g. styryl, dimethylaminostyryl, diethylaminostyryl, dipropylaminostyryl, methoxystyryl, ethoxystyryl, and methylstyryl), nitro, hydroxyl, mercapto, thioether, carboxyl, carboxylate, carboxyamide, cyano, and substituted or unsubstituted arylazo groups (e.g. phenylazo, α-naphthylazo, β-naphthylazo, dimethylaminophenylazo, chlorophenylazo, nitrophenylazo, methoxyphenylazo, and tolyazo) of the combinations of $R_{38}'$-aromatic ring $X_3'$, aromatic ring $X_3'$—$R_{39}'$, $R_{39}'$-$R_{40}'$, $R_{40}'$-$R_{41}'$, and $R_{41}'$-$R_{42}'$, at least one may or may not form a substituted or unsubstituted aromatic ring (e.g. benzene, naphthalene, chlorobenzene, ethylbenzene, or methoxybenzene, heterocyclic ring (e.g. furan, benzofuran, pyrrole, thiophene, pyriline or quinoline), or ring formed with aliphatic chains (e.g. dimethylene, trimethylene or tetramethylene). The azulenium skelton represented by $Q^{\oplus}$ can be symmetrical or asymmetrical. $R_{43}$ represents hydrogen, nitro, cyano, or alkyl (e.g. methyl, ethyl, propyl, or butyl), or aryl (e.g. phenyl, tolyl, or xylyl), and $n_3$ is 0, 1, or 2.

General formula (13):

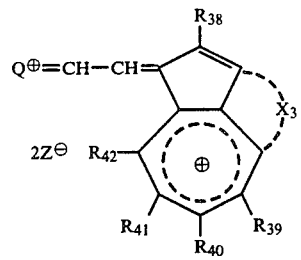

$R_{38}$ to $R_{42}$ and $X_3$ in this formula are as defined above.

General formula (14):

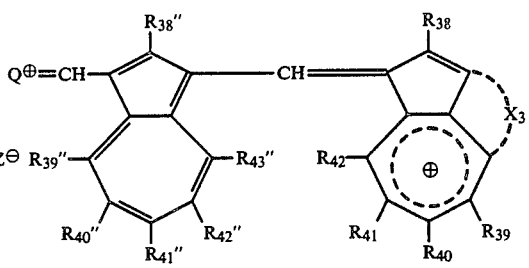

In this formula, $R_{38}$ to $R_{42}$, and $X_3$ are as defined above.

Each of $R_{37}''$ and $R_{38}''$ in this formula represents hydrogen, halogen (e.g, chlorine, bromine, or iodine), or an organic monovalent residue, which can be selected from a variety of radicals. Preferred examples of the organic monovalent residues are alkyl groups (e.g. methyl, ethyl, n-propyl, isopropyl, n-butyl, t-butyl, n-amyl, n-hexyl, n-octyl, 2-ethylhexyl, and t-octyl), alkoxy groups (e.g. methoxy, ethoxy, propoxy, and butoxy), substituted or unsubstituted aryl groups (e.g. phenyl, tolyl, xylyl, ethylphenyl, methoxyphenyl, ethoxyphenyl, chlorophenyl, nitrophenyl, dimethylaminophenyl, α-naphthyl, and β-naphthyl), substituted or unsubstituted heterocyclic groups (e.g. pyridyl, quinolyl, carbazolyl, furyl, thienyl and pyrazolyl), substituted or unsubstituted aralkyl groups (e.g. benzyl, 2-phenylethyl, 2-phenyl-1-methylethyl, bromobenzyl, 2-bromophenylethyl, methylbenzyl, methoxybenzyl, and nitrobenzyl), acyl groups (e.g. acetyl, propionyl, butyryl, valeryl, benzoyl, toluoyl, naphthoyl, phthaloyl, and furoyl), substituted or unsubstituted amino groups (e.g. amino, dimethylamino, diethylamino, dipropylamino, acetylamino, and benzoylamino), substituted or unsubstituted styryl groups (e.g. styryl, dimethylaminostyryl, diethylaminostyryl, dipropylaminostyryl, methoxystyryl, ethoxystyryl, and methylstyryl), nitro, hydroxyl, mercapto, thioether, carboxy, carboxylate, carboxyamide, cyano, and substituted or unsubstituted arylazo groups (e.g. phenylazo, α-naphthylazo, β-naphthylazo, dimethylaminophenylazo, chlorophenylazo, nitrophenylazo, methoxyphenylazo, and tolylazo). At least one of the combinations of $R_{39}''$-$R_{40}''$, $R_{40}''$-$R_{41}''$, $R_{41}''$-$R_{42}''$, and $R_{42}''$-$R_{43}''$ may or may not form a substituted or unsubstituted aromiatic ring (e.g. benzene, naphthalene, chlorobenzene, ethylbenzene, or methoxybenzene, heterocyclic ring (e.g. furan, benzofuran, pyrrole, thiophene, pyridine or quinoline), or ring formed with aliphatic chains (e.g. dimethylene, trimethylene or tetramethylene).

General formula (15):

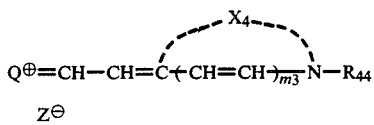

In this formula, $X_4$ represents a non-metal-atomic group necessary to complete a nitrogen-containing heterocyclic ring (e.g, pyridine, thiazole, benzothiazole, oxazole, benzoxazole, naphthoxazole, imidazole, benzimidazole, naphthoimidazole, 2-quinoline, 4-quinoline, isoquinoline or indole). This heterocyclic ring may be substituted with halogen (e.g. chlorine, bromine, or iodine), alkyl (e.g. methyl, ethyl, propyl, or butyl), or aryl (e.g. phenyl, tolyl, or xylyl). $R_{44}$ represents alkyl (e.g. methyl, ethyl, propyl, or butyl), substituted alkyl (e.g. 2-hydroxyethyl, 2-methoxyethyl, 2-ethoxyethyl, 3-hydroxypropyl, 3-methoxypropyl, 3-ethoxypropyl, 3-chloropropyl, 3-bromopropyl, or 3-carboxypropyl), cycloalkyl (e.g. cyclohexyl or cyclopropyl), allyl, aralkyl (e.g. benzyl, 2-phenylethyl, 3-phenylpropyl, 4-phenylbutyl, α-naphthylmethyl, or β-naphthylmethyl), substituted aralkyl (e.g. methylbenzyl, ethylbenzyl, dimethylbenzyl, trimethylbenzyl, chlorobenzyl, or bromobenzyl), aryl (e.g. phenyl, tolyl, xylyl, α-naphthyl, or β-naphthyl), or substituted aryl (e.g. chlorophenyl, dichlorophenyl, trichlorophenyl, ethylphenyl, methoxyphenyl, dimethoxyphenyl, aminophenyl, nitrophenyl, or hydroxyphenyl). $m_3$ represents an integer of 0 or 1.

General formula (16):

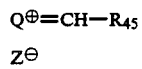

In this formula; $R_{45}$ represents substituted or unsubstituted aryl (e.g. phenyl, tolyl, xylyl, biphenyl, α-naphthyl, β-naphthyl, anthryl, pyrenyl, methoxyphenyl, dimethoxyphenyl, trimethoxyphenyl, ethoxyphenyl, diethoxyphenyl, chlorophenyl, trichlorophenyl, bromophenyl, dibromophenyl, tribromophenyl, ethylphenyl, diethylphenyl, nitrophenyl, aminophenyl, dimethylaminophenyl, diethylaminophenyl, dibenzylaminophenyl, dipropylaminophenyl, morpholinophenyl, piperidylphenyl, piperazinophenyl, diphenylaminophenyl, acetylaminophenyl, benzoylaminophenyl, acetylphenyl, benzoylphenyl, or cyanophenyl).

General formula (17):

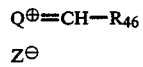

In this formula; $R_{46}$ represents a monovalent heterocyclic residue derived from a heterocyclic ring (furan, thiophene, benzofran, thionaphthene, dibenzofuran, carbazole, phenothiazine, phenoxazine, pyridine or the like.

General formula (18):

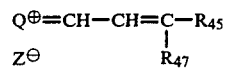

In this formula; $R_{47}$ represents hydrogen, alkyl (e.g. methyl, ethyl, propyl, or butyl), or substituted or unsubstituted aryl (e.g. phenyl, tolyl, xylyl, biphenyl, ethylphenyl, chlorophenyl, methoxyphenyl, ethoxyphenyl, nitrophenyl, aminophenyl, dimethylaminophenyl, α-naphthyl, β-naphthyl, anthryl, or pyrenyl) and $R_{45}$ is as defined above.

General formula (19):

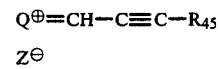

In this formula, $R_{45}$ is as defined above.

General formula (20):

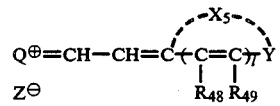

In this formula, $X_5$ represents an atomic group necessary to complete pyrane, thiapyrane, selenapyrane, benzopyrane, benzothiapyrane, benzoselenapyrane, naphthopyrane, naphthothiapyrane, or naphthoselenapyrane ring substituted or unsubstituted; l is 0 or 1; Y is sulfur, oxygen, or selenium; $R_{11}$ and $R_{12}$ each represents hydrogen alkyl (e.g. methyl, ethyl, propyl, or butyl), alkoxy (e.g. methoxy, ethoxy, propoxy, or butoxy), substituted or unsubstituted aryl (e.g. phenyl, tolyl, xylyl, chlorophenyl, biphenyl, or methoxyphenyl), substituted or unsubstituted styryl (e.g. styryl, p-methylstyryl, o-chlorostyryl, or p-methoxystyryl), substituted or unsubstituted 4-phenyl-1,3-butadienyl (e.g. 4-phenyl-1,3-butadienyl or 4-(p-methylphenyl)-1,3-butadienyl), or a substituted or unsubstituted heterocyclic group (e.g. quinolyl, pyridyl, carbazolyl, or furyl).

Examples of $Z^\ominus$ in the above general formulae are anionic moieties of perchlorate, fluoroborate, sulfoacetate, iodide, chloride, bromide, p-toluenesulfonate, alkylsulfonates, alkyldisulfonates, benzenedisulfonate, halosulfonates, picrate, tetracyanoethylene anion moiety, tetracyanoquinodimethane anion moiety and the like.

Examples of the azulenium compound used in this invention are enumerated below.

The azulenium salt compounds having the
General formula (1) or (2)

Compound

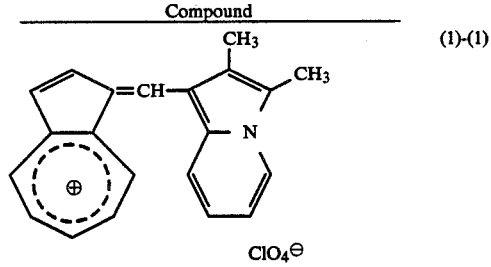

(1)-(1)

-continued
The azulenium salt compounds having the
General formula (1) or (2)
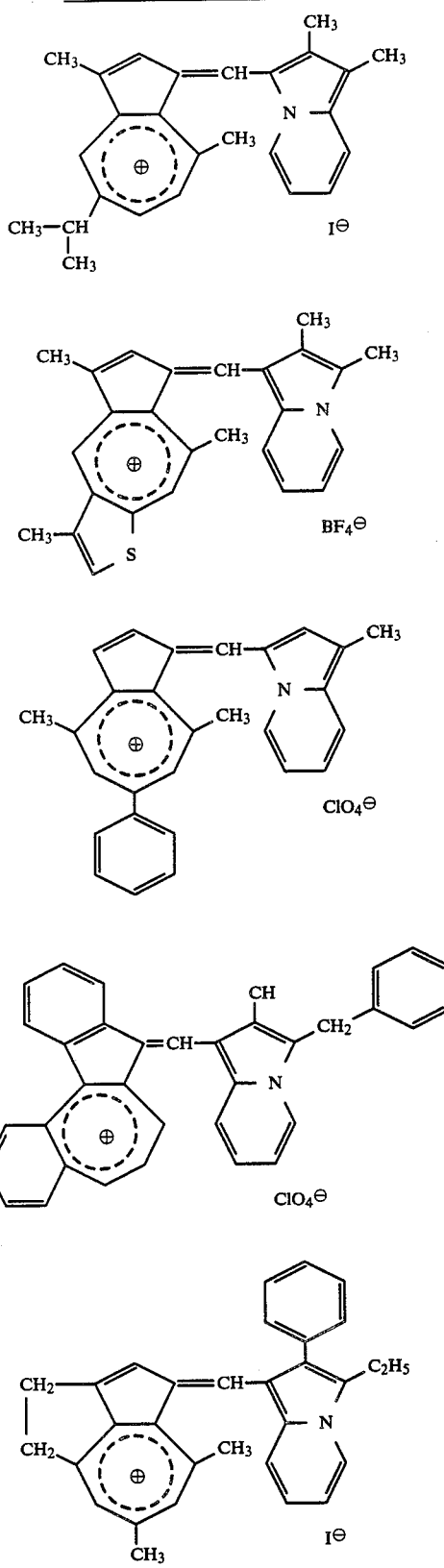
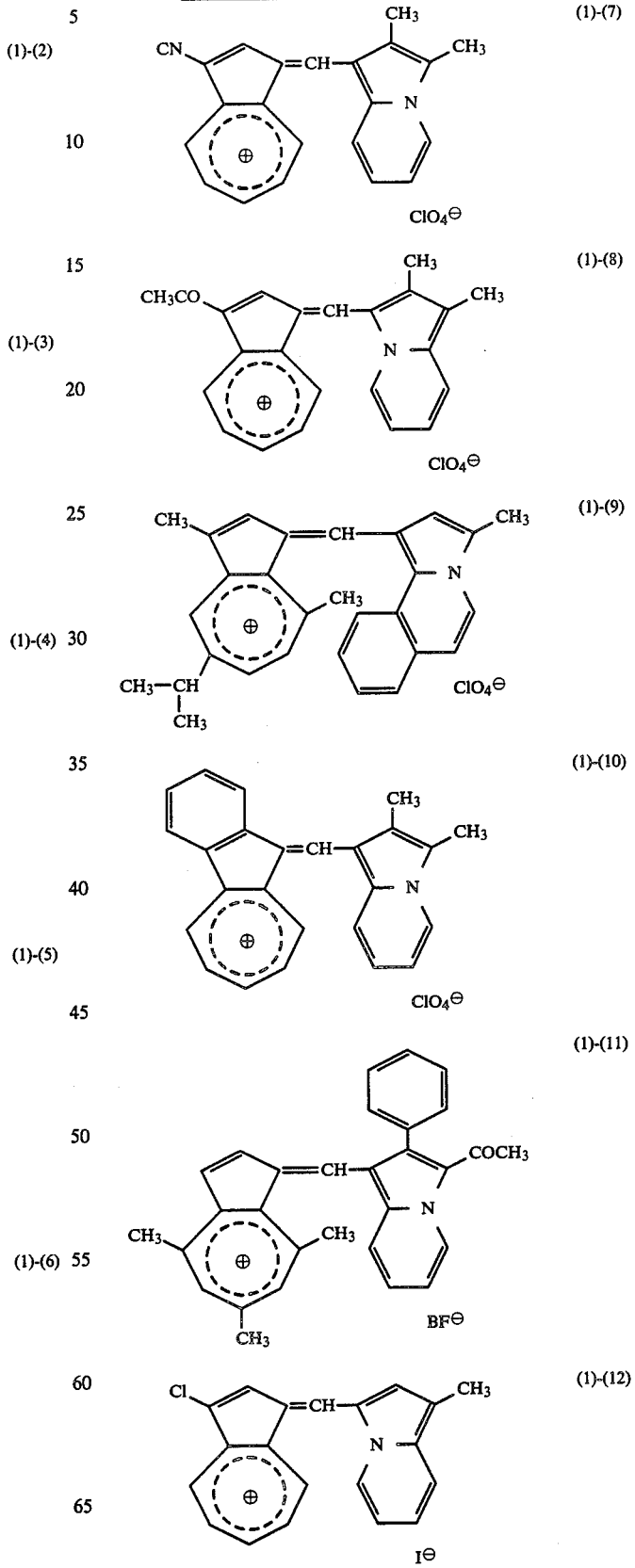

-continued
The azulenium salt compounds having the
General formula (1) or (2)

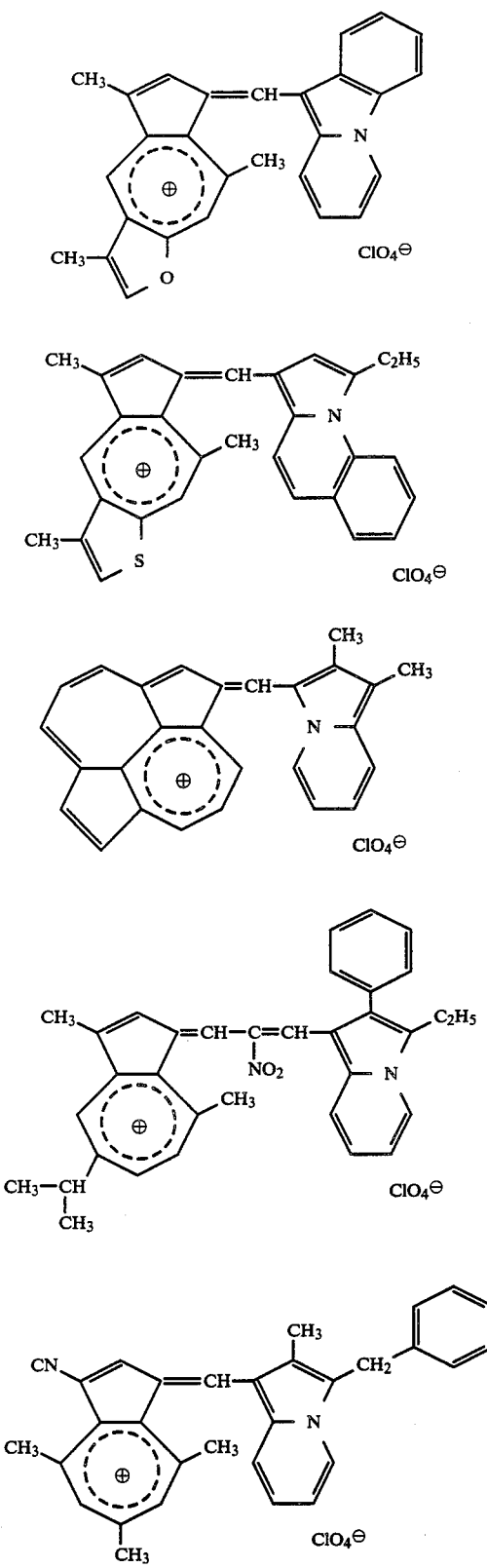
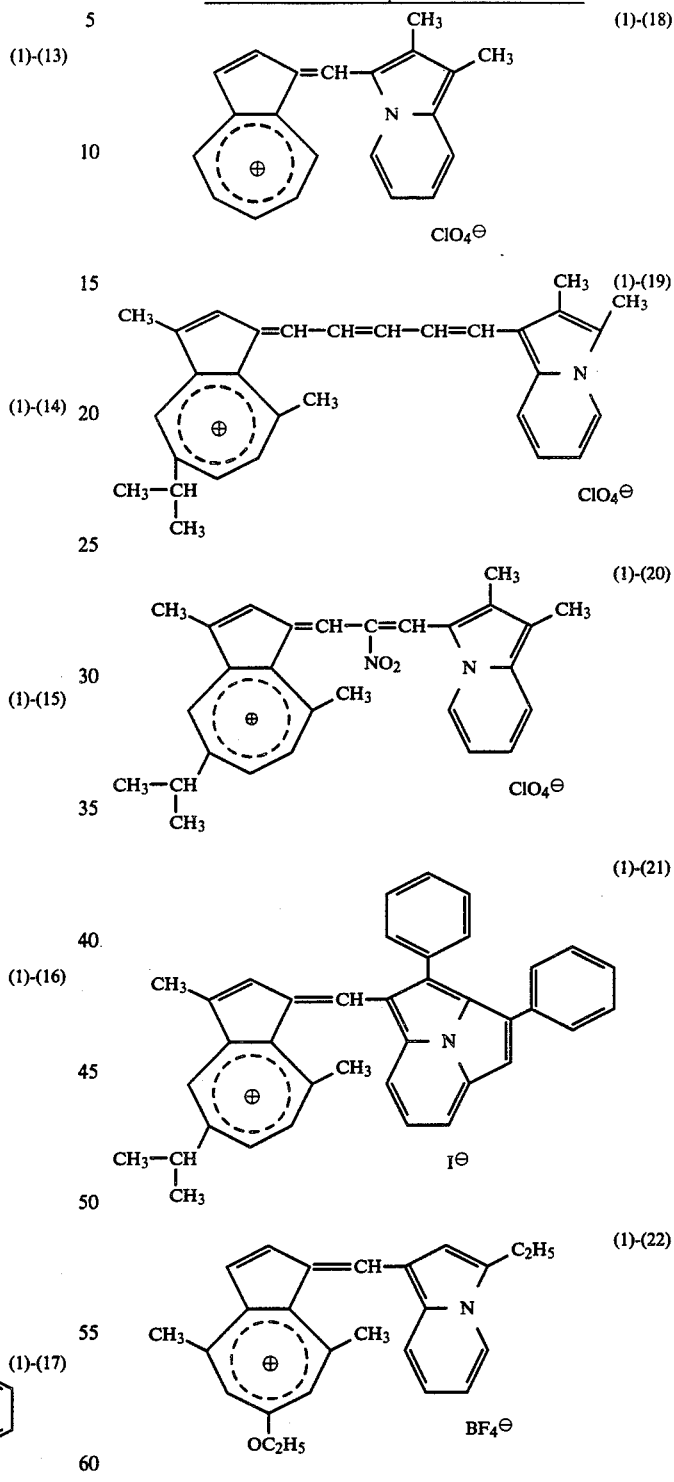

The compounds having the formula (1) or (2) wherein $n_1=0$ are prepared by allowing 1-formylazulene compounds to react with 1- or 3-unsubstituted indolizine compounds in the presence of weak acids in an appropriate solvent as described in Angew. Chem., Vol. 71, No. 3, page 125 (1959). They are also prepared by allowing azulene compounds react with 1- or 3-formylindolizine compounds. In addition, the compounds of such formulae wherein $n_1=1$ or 2 are prepared by allowing the aldehyde compounds having the general formula:

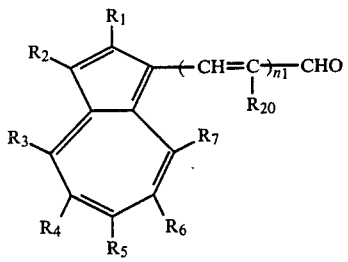

that is described in J. Chem. Soc. (1961), pages 3579-3593, wherein $R_1$-$R_7$, $R_{20}$ and n are as defined in the description of the general formula of the present invention, to react with 1- or 3-unsubstituted indolizine compounds.

As the reaction solvent, there may be used alcohols such as ethanol, butanol, benzyl alcohol and the like, nitriles such as acetonitrile, propionitrile and the like, carboxylic acids such as acetic acid and the like, alicyclic ethers such as dioxane, tetrahydrofuran and the like. Also, aromatic hydrocarbons such as benzene and the like may be used by mixing with butanol, benzyl alcohol or the like. The temperature during reaction may be selected from a range of room temperature to the boiling point.

A representative preparation example is described below.

Preparation example 1: Compound No. (1)-(1)

1-Formylazulene (0.94 g) and 1,2-dimethylindolizine (0.87 g) were mixed in tetrahydrofuran (80 ml) at room temperature, and to the liquid was added 70% perchloric acid (2.5 ml). Then the resulting liquid was allowed to react at room temperature for two hours, to be cooled and to stand overnight. The precipitate was filtered and washed with tetrahydrofuran (20 ml), water (50 ml×4) and tetrahydrofuran (20 ml×2) to afford compound No. (1)-(1) (1.20 g).

Yield: 52%

Absorption spectrum in ethanol, λmax: 568 nm

Anal.: $C_{21}H_{18}ClNO_4$

|   | Calcd. (%) | Found (%) |
|---|---|---|
| C | 65.71 | 65.53 |
| H | 4.74 | 4.87 |
| N | 3.65 | 3.72 |
| Cl | 9.24 | 9.14 |

The azulenium salt compounds having the general formula (3)

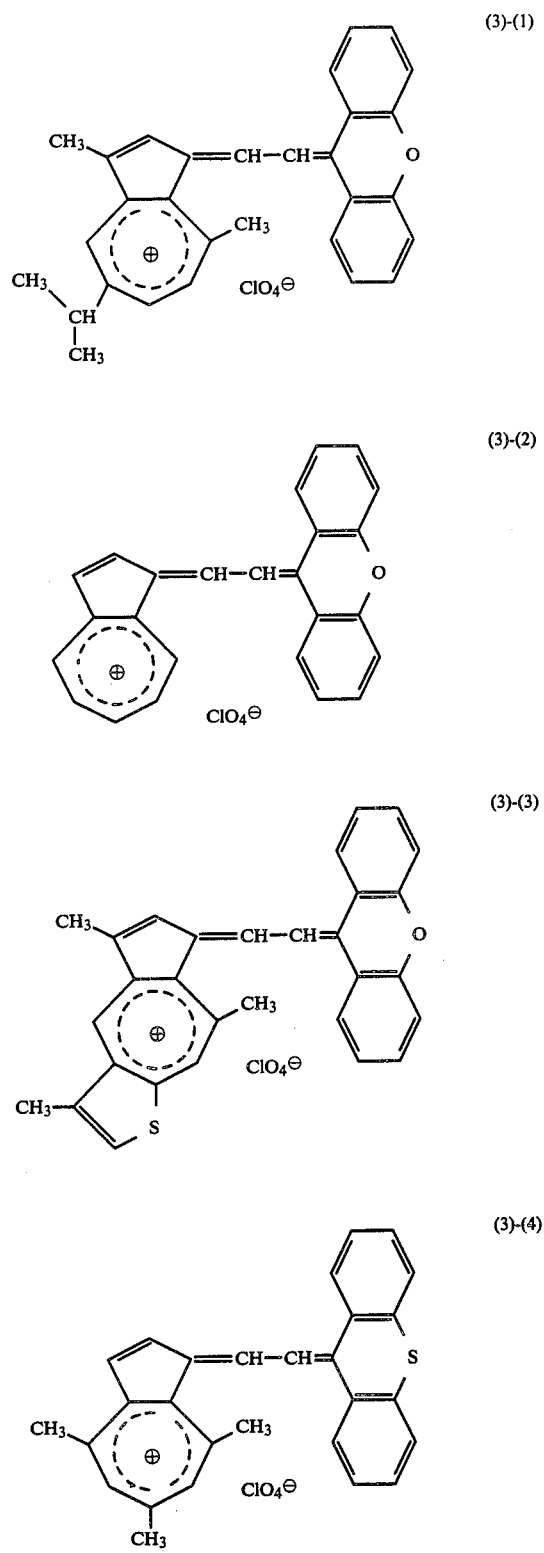

-continued
The azulenium salt compounds having the
general formula (3)
(3)-(5)
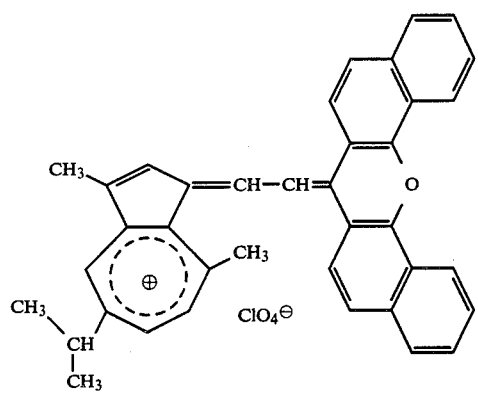
(3)-(6)
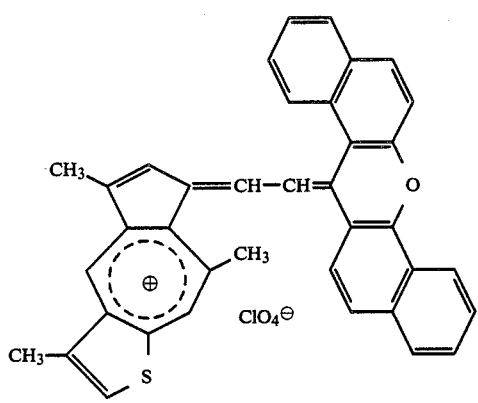
(3)-(7)
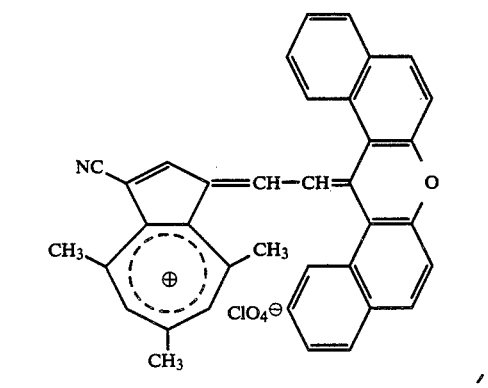
(3)-(8)
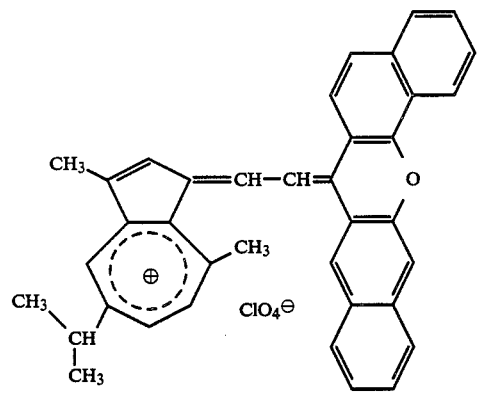
-continued
The azulenium salt compounds having the
general formula (3)
(3)-(9)
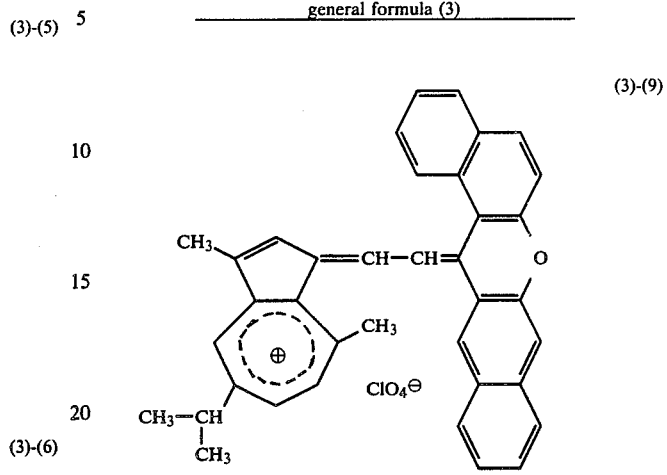
(3)-(10)
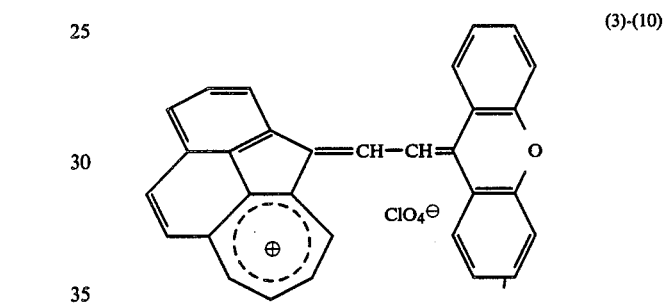
(3)-(11)
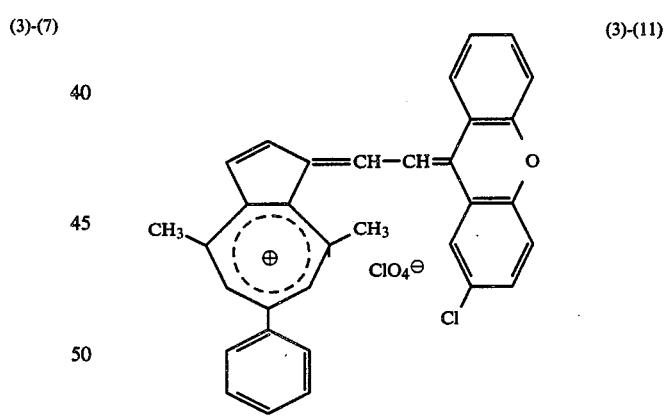
(3)-(13)
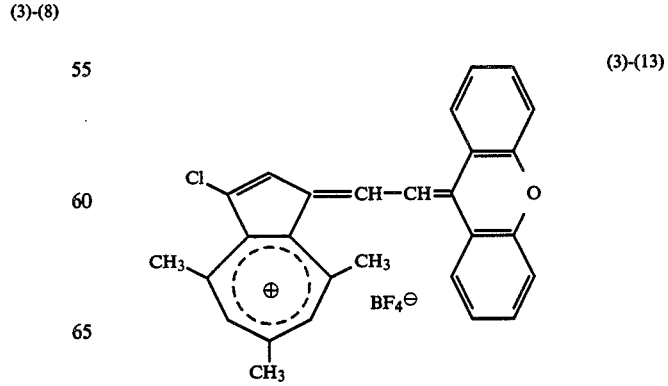

-continued
The azulenium salt compounds having the general formula (3)
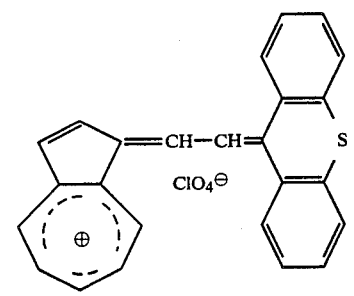 (3)-(14)
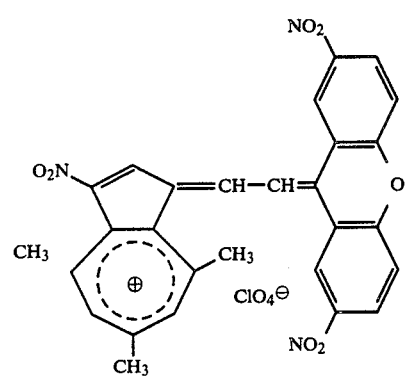 (3)-(15)
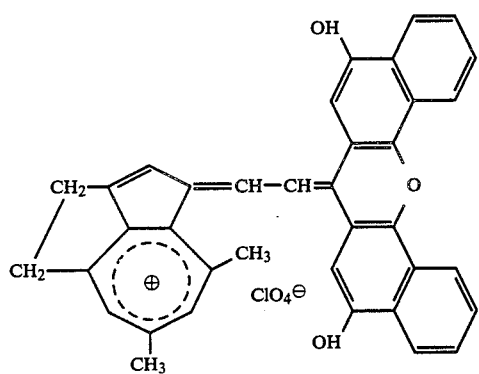 (3)-(16)
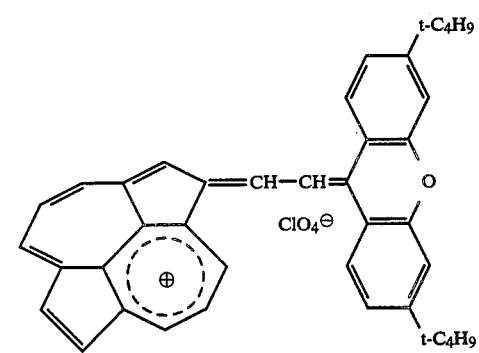 (3)-(17)
-continued
The azulenium salt compounds having the general formula (3)
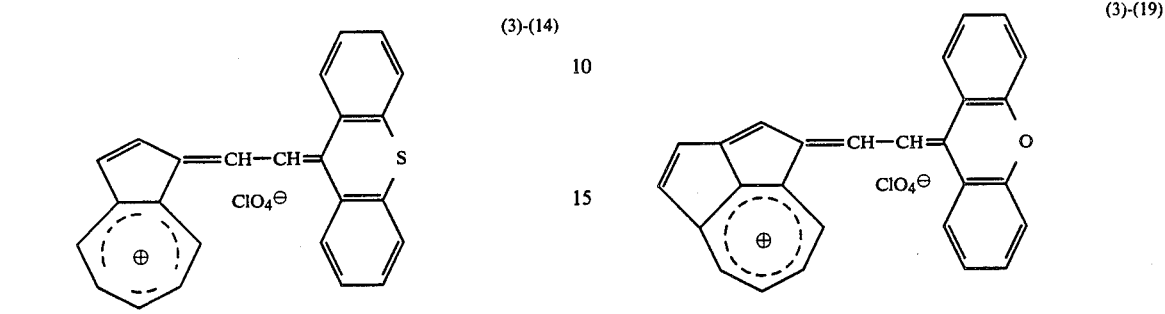 (3)-(19)
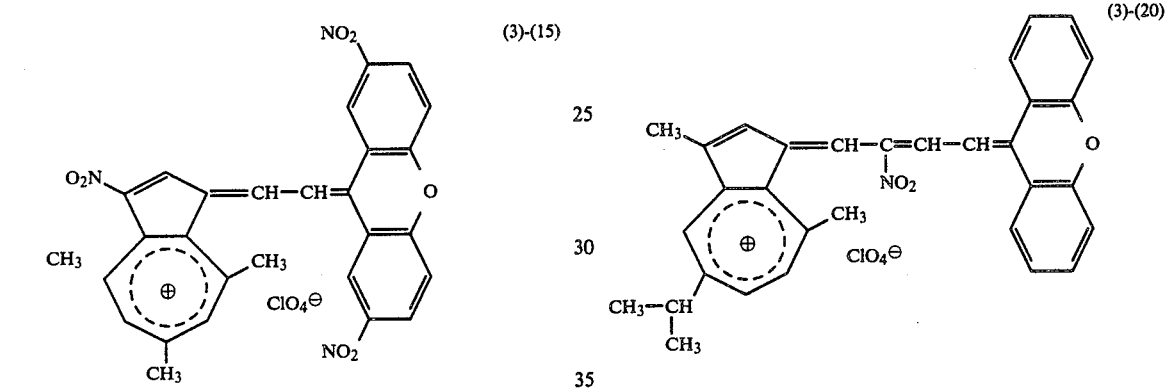 (3)-(20)
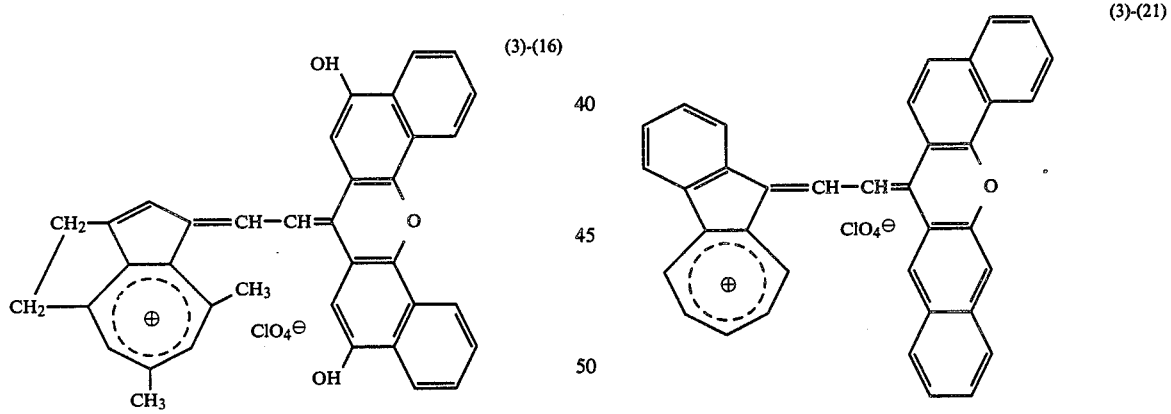 (3)-(21)
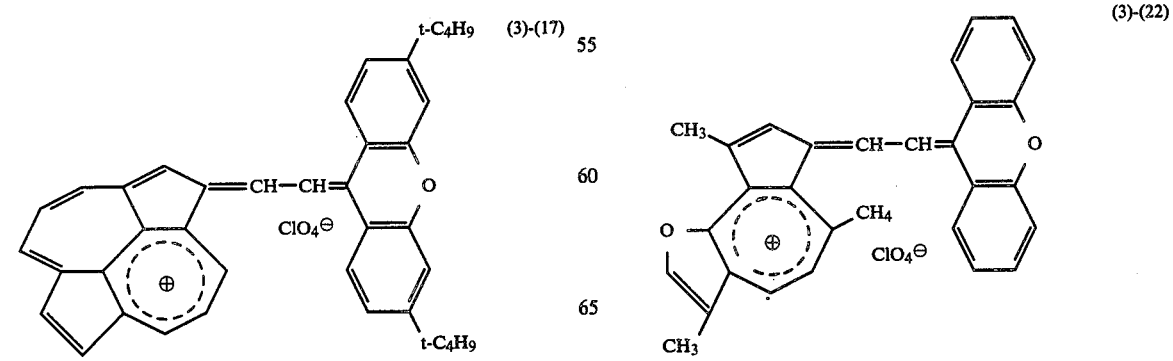 (3)-(22)

-continued
The azulenium salt compounds having the
general formula (3)

(3)-(23)
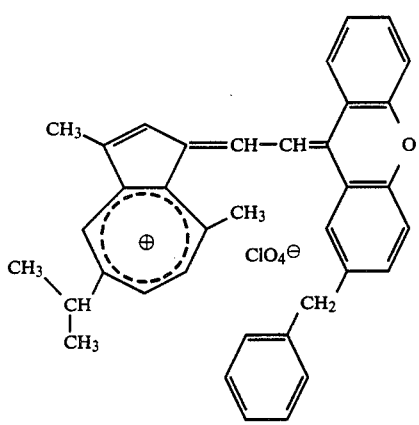

(3)-(24)
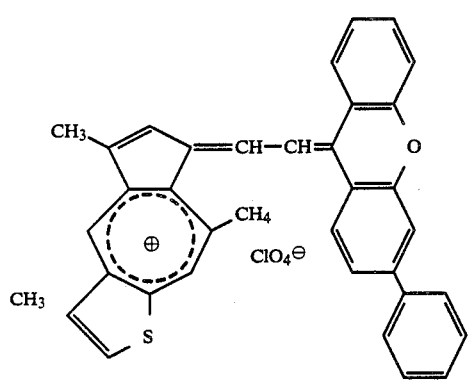

(3)-(25)
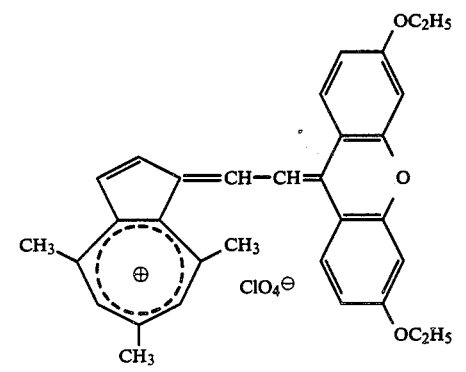

(3)-(26)
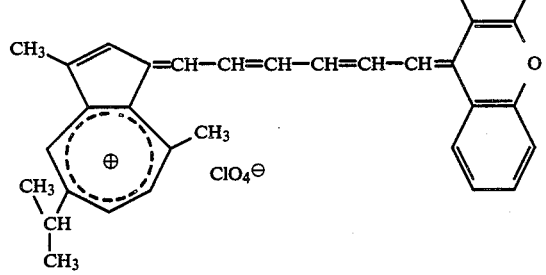

-continued
The azulenium salt compounds having the
general formula (3)

(3)-(27)
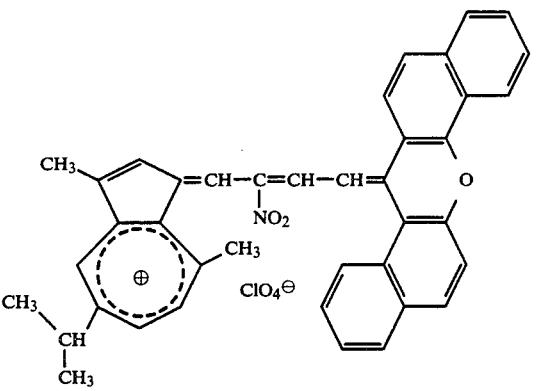

The azulenium compounds having the general formula (3) are prepared by allowing formylazulene compounds having a general formula (21):

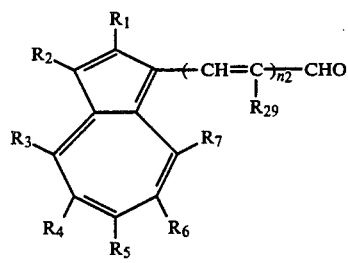

wherein $R_1$-$R_7$, $R_{29}$ and $n_2$ are as previously defined, to react in an appropriate solvent with the compounds having a general formula (22):

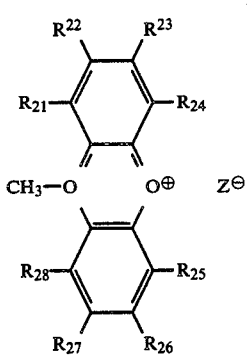

wherein $R_{21}$-$R_{28}$ and $Z^{\ominus}$ are as previously defined.

Also, the azulenium salt compounds having the general formula (3) wherein $n_2=2$ are readily prepared by allowing the azulene compounds having a general formula (23):

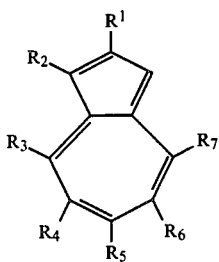

wherein R₁–R₇ are as previously defined, to react in an appropriate solvent with the aldehyde compounds having a general formula (24):

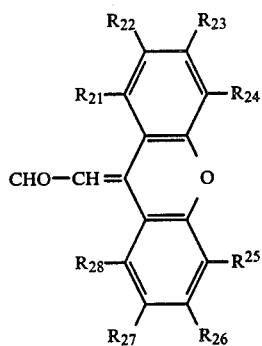

wherein R₂₁–R₂₈ are as previously defined, in the presence of strong acids.

Some representative preparation examples are described below.

Preparation Example 2: Compound No. (3)-(1)

1-Formyl-3,8-dimethyl-5-isopropylazulene (2.26 g) was allowed to react with 9-methylxanthilium perchlorate (2.95 g) in acetic anhydride (180 ml) at a liquid temperature of 80°–90° C. for two hours. After allowed to be cooled, precipitated crystals were filtered, washed with glacial acetic acid, water and ethanol successively and dried to afford the azulenium salt compound (4.07 g).

Yield: 81%
Anal.: $C_{30}H_{27}ClO_5$

|   | Calcd. (%) | Found (%) |
|---|---|---|
| C | 71.63 | 71.52 |
| H | 5.42 | 5.50 |
| Cl | 7.05 | 7.12 |

Preparation Example 3: Compound No. (3)-(5)

To a solution of 1,4-dimethyl-7-isopropylazulene (0.74 g) and 9-formylmethylene-3,4,5,6-dibenzoxanthene (1.2 g) in tetrahydrofuran (80 ml) was added dropwise 70% perchloric acid (2 ml) at room temperature, followed by stirring at the same temperature for four hours. The precipitate was filtered, washed with tetrahydrofuran, water and tetrahydrofuran succeissively, and dried to afford the azulenium salt compound (1.01 g).

Yield: 45%
Anal.: $C_{38}H_{31}ClO_5$

|   | Calcd. (%) | Found (%) |
|---|---|---|
| C | 75.67 | 75.71 |
| H | 5.19 | 5.26 |
| Cl | 5.88 | 5.79 |

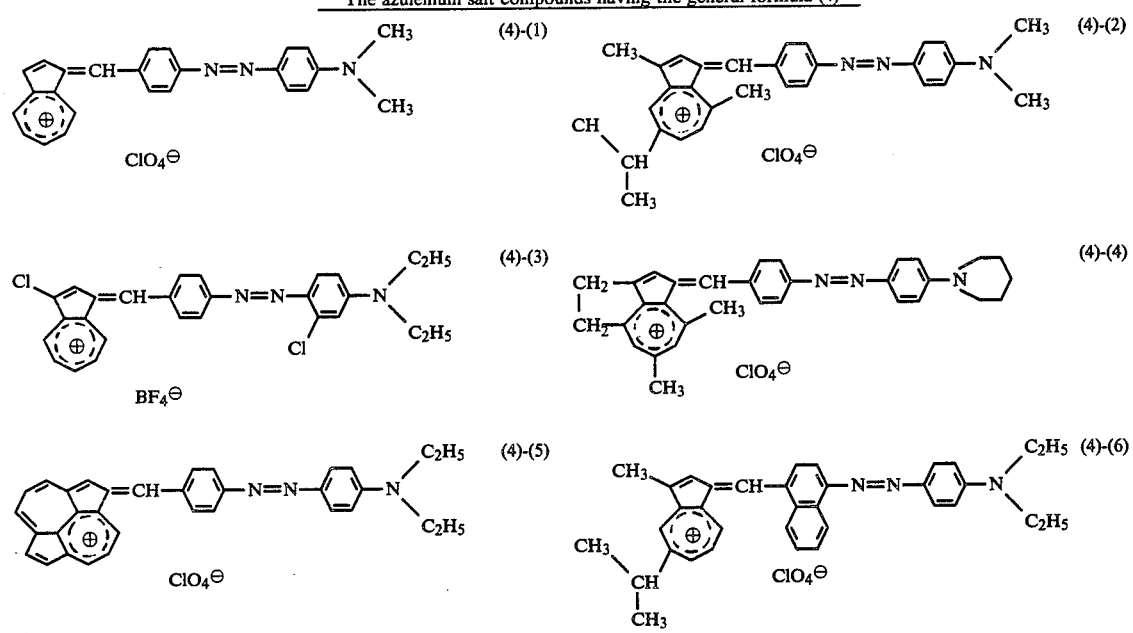

The azulenium salt compounds having the general formula (4)

-continued
The azulenium salt compounds having the general formula (4)

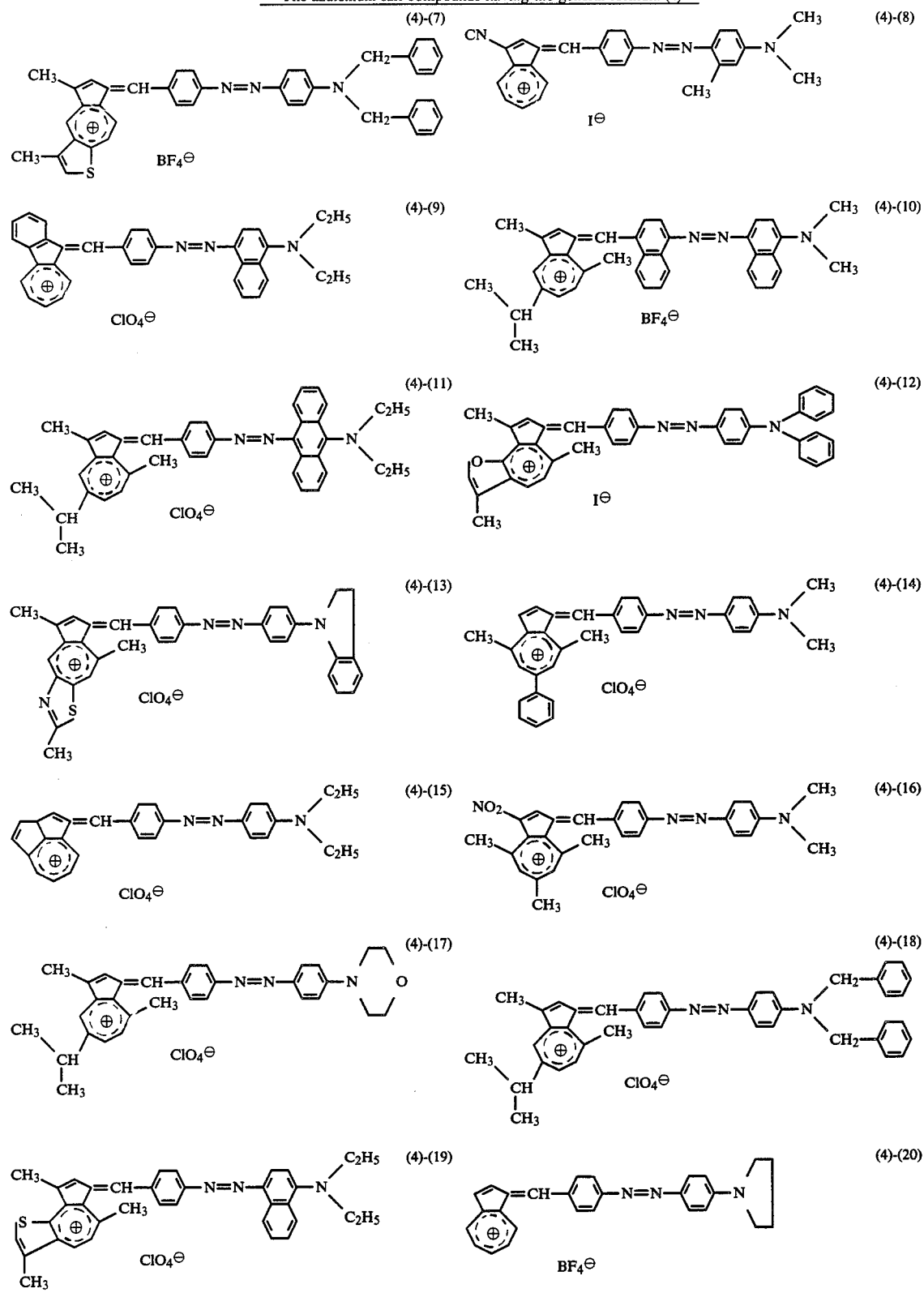

The compounds having the general formula (4) are prepared by mixing azulene compounds with the corresponding aldehyde compounds in an appropriate solvent in the presence of strong acids as described in J. Chem. Soc. (1958), pages 1110–1117, ibid. (1960), pages 494–501 and ibid. (1961), pages 3579–3593.

As the reaction solvent, there may be used alcohols such as ethanol, butanol, benzyl alcohol and the like;

nitriles such as acetonitrile, propionitrile and the like; organic carboxyl acids such as acetic acid and the like; acid anhydrides such as acetic anhydride and the like; alicyclic ethers such as dioxane, tetrahydrofuran and the like. Also, aromatic hydrocarbons such as benzene may be used by mixed with buthanol, benzyl alcohol or the like. The temperature during reaction may be selected from a range of room temperature to the boilding point.

The azulenium salt compounds having the general formula (5)

-continued
The azulenium salt compounds having the general formula (5)

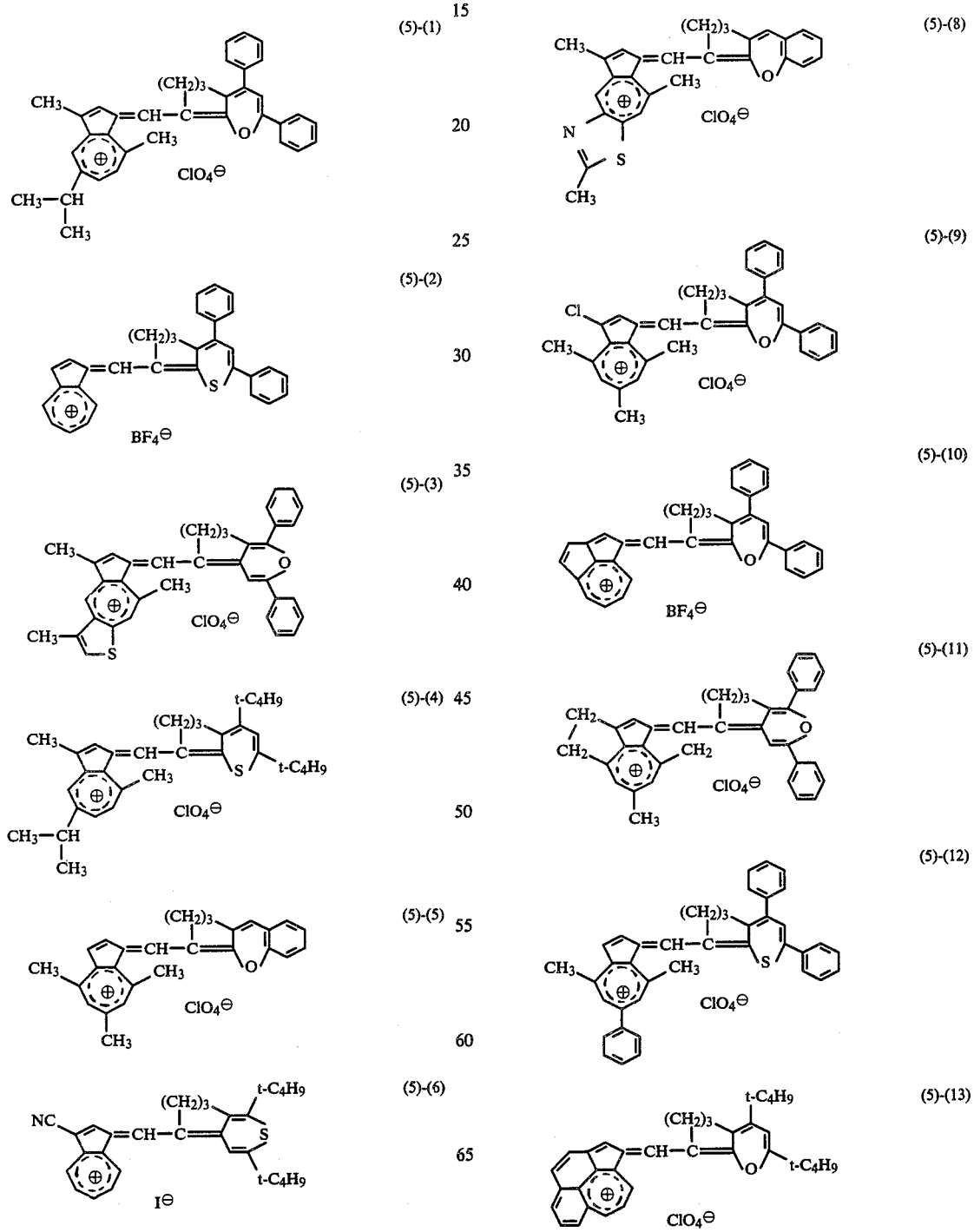

-continued
The azulenium salt compounds having the general formula (5)

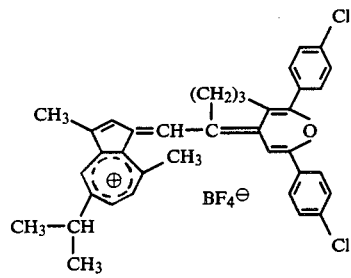
(5)-(14)

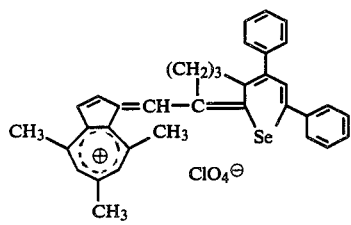
(5)-(15)

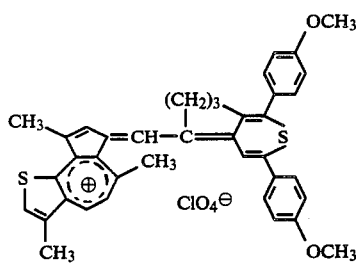
(5)-(16)

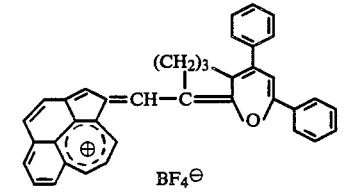
(5)-(17)

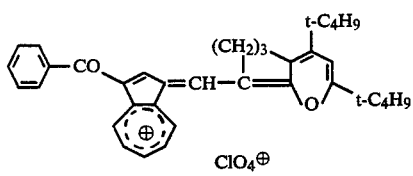
(5)-(18)

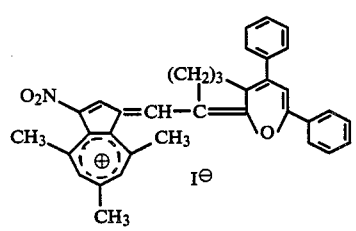
(5)-(19)

-continued
The azulenium salt compounds having the general formula (5)

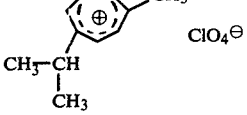
(5)-(20)

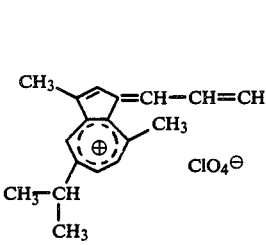
(5)-(21)

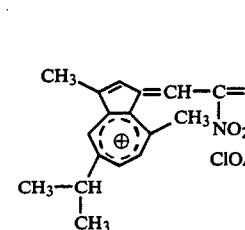
(5)-(22)

The compounds having the general formula (5) are prepared by allowing the formylazulene compounds having a general formula (25):

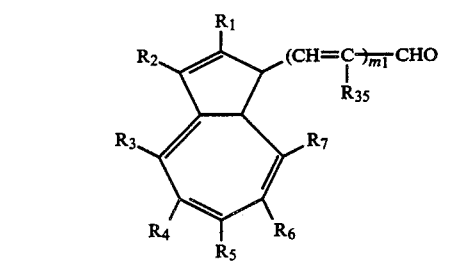

wherein $R_1-R_7$, $R_{35}$ and $m_1$ are as previously defined, to react in an appropriate solvent with the compounds having a general formula (26):

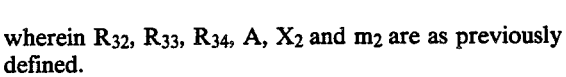

wherein $R_{32}$, $R_{33}$, $R_{34}$, A, $X_2$ and $m_2$ are as previously defined.

Also, the azulenium salt compounds having the general formula (5) wherein $m_1=0$ are readily prepared by allowing the azulene compounds having a general formula (27):

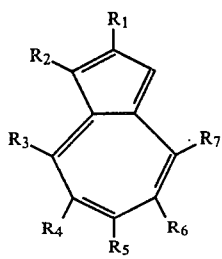

wherein R$_1$–R$_7$ are as previously defined, to react with the aldehyde compounds having a general formula (28):

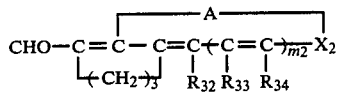

wherein R$_{32}$, R$_{33}$, R$_{34}$, A, X$_2$ and m$_2$ are as previously defined in the presence of strong acids in an appropriate solvent. appropriate solvent.

As the solvent to be used, there may be enumerated a wide range of organic solvent, in particular alcohols such as ethanol, propanol, butanol and the like; nitriles such as acetonitrile and the like, ketones such as methyl ethyl ketone and the like, nitro compounds such as nitrobenzene and the like, halogenated hydrocarbons such as tetrachloroethane and the like, organic acids such as acetic acid and the like, and acid anhydrides such as acetic anhydride and the like.

Some representative preparation examples for azulenium salt compounds of the general formula (5) are described below.

Preparation Example 4: Compound (5)-(1)

1-Formyl-3,8-dimethyl-5-isopropylazulene (1.5 g) was allowed to react with 2,4-diphenyl-5,6,7,8-tetrahydrobenzopyrylium perchlorate (2.56 g) in acetic anhydride (50 ml) at a liquid temperature of 80°–90° C. for two hours. After cooled to room temperature, precipitated crystals were filtered, washed with glacial acetic acid, water and ethanol successively, and dried to afford the azulenium salt compound (3.35 g).

Yield: 85%

Anal.: C$_{37}$H$_{35}$ClO$_5$

|   | Calcd. (%) | Found (%) |
|---|---|---|
| C | 74.66 | 74.57 |
| H | 5.94 | 6.03 |
| Cl | 5.96 | 5.83 |

Preparation Example 5: Compound No. (5)-(9)

1-Chloro-4,6,8-trimethylazulene (2.4 g) and 2,4-diphenyl-tetrahydrobenzopyrrolo-8-ω-aldehyde (3.69 g) were dissolved in tetrahydrofuran (150 ml), and 70% perchloric acid (4 ml) was added at a liquid temperature of 25° C., then the resulting solution was stirred at the same temperature for six hours. The precipitate was filtered, washed with tetrahydrofuran, water and tetrahydrofuran successively, and dried to afford the azulenium salt (3.88 g).

Yield: 55%

Anal.: C$_{35}$H$_{30}$Cl$_2$O$_5$

|   | Calcd. (%) | Found (%) |
|---|---|---|
| C | 69.88 | 69.73 |
| H | 5.04 | 5.18 |
| Cl | 11.79 | 11.64 |

The azulenium salt compounds having the general formula (6)

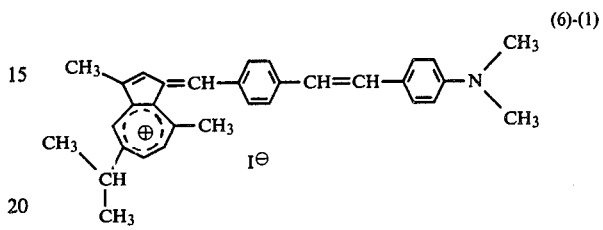

(6)-(1)

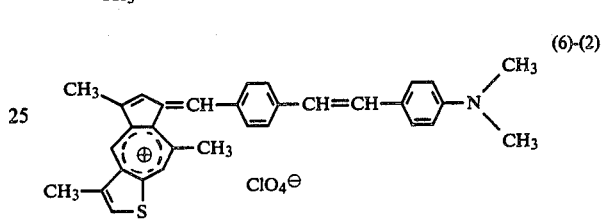

(6)-(2)

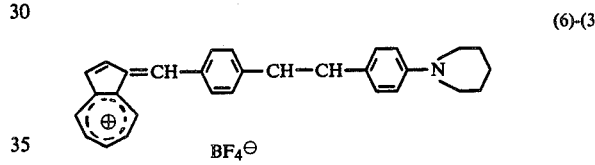

(6)-(3)

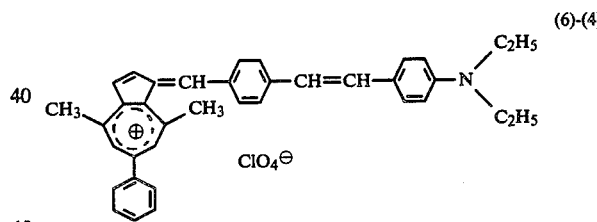

(6)-(4)

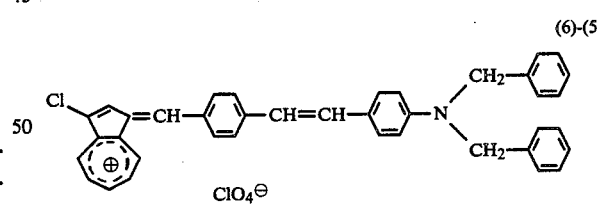

(6)-(5)

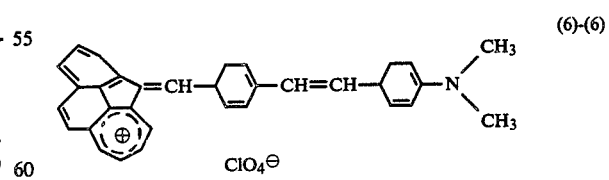

(6)-(6)

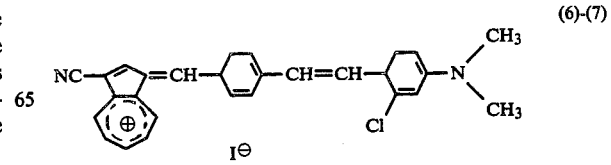

(6)-(7)

-continued
The azulenium salt compounds having the general formula (6)

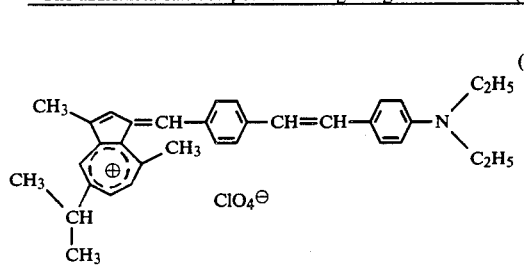
(6)-(8)

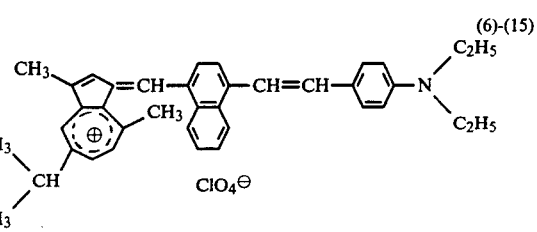
(6)-(15)

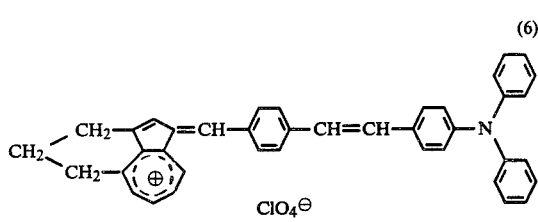
(6)-(9)

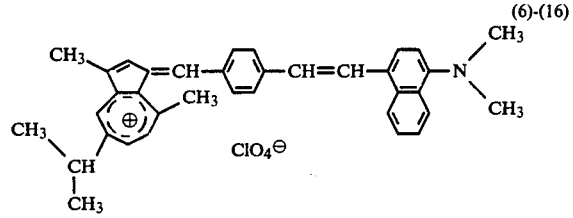
(6)-(16)

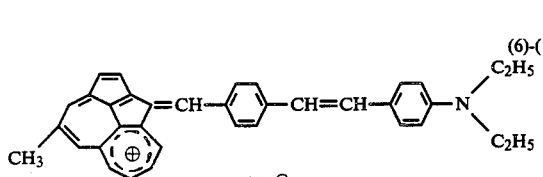
(6)-(10)

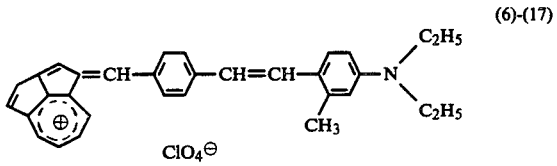
(6)-(17)

(6)-(11)

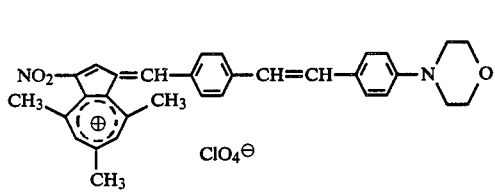
(6)-(18)

(6)-(12)

(6)-(13)

The compounds having the general formula (6) are prepared by mixing azulene compounds with the corresponding aldehyde compounds in an appropriate solvent in the presence of strong acids as described in J. Chem. Soc. (1958), pages 1110–1117, ibid. (1960), pages 494–501 and ibid. (1961), pages 3579–3593.

As the reaction solvent, there may be used alcohols such as ethanol, butanol, benzyl alcohol and the like; nitriles such as acetonitrile, propionitrile and the like; organic carboxylic acids such as acetic acid and the like; acid anhydrides such as acetic anhydride and the like; alicyclic ethers such as dioxane, tetrahydrofuran and the like. Also, aromatic hydrocarbons such as benzene and the like may be used by mixed with butanol, benzyl aocohol or the like. The temperature during reaction may be selected from a range of room temperature to the boiling point.

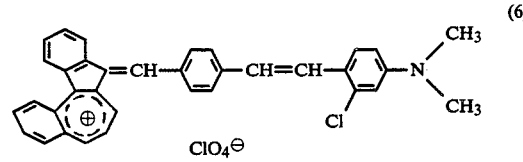

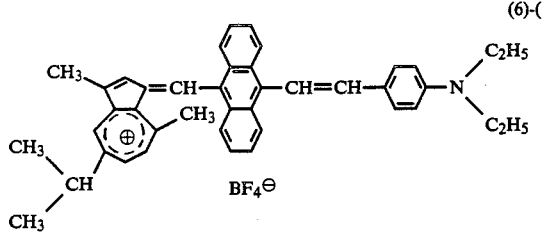
(6)-(14)

Examples of the compounds having the general formula (10)

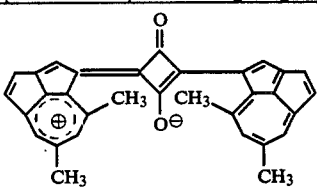
(7)-(1)

Examples of the compounds having the general formula (10)
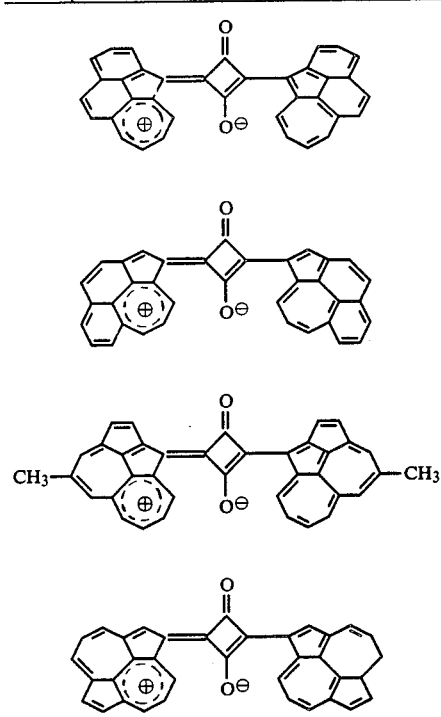
Examples of the compounds having the general formula (11)
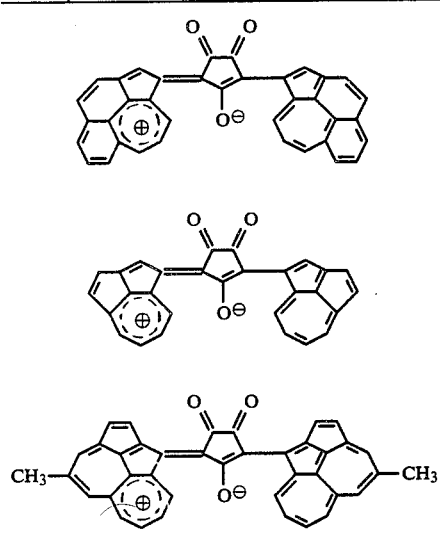
Examples of the compounds having the general formula (12)
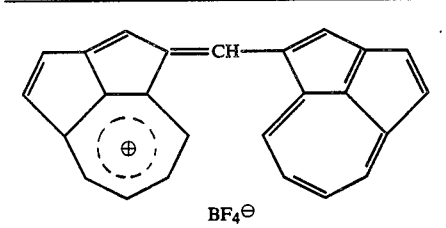
Examples of the compounds having the general formula (12)
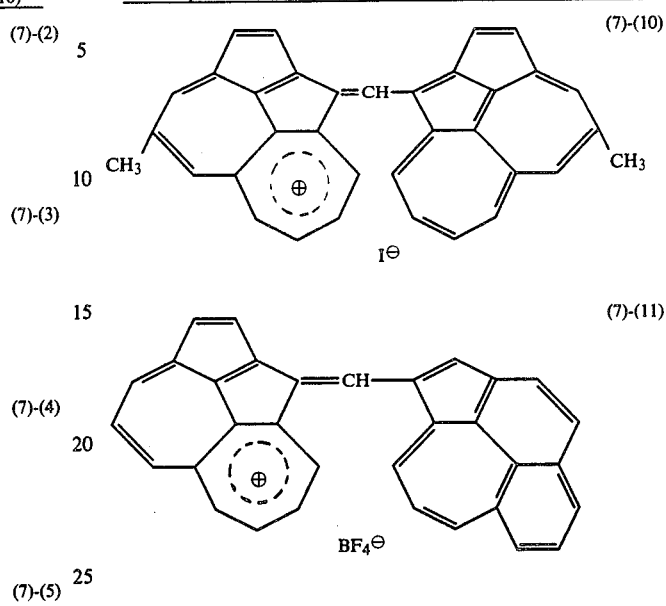
Examples of the compounds having the general formula (13)
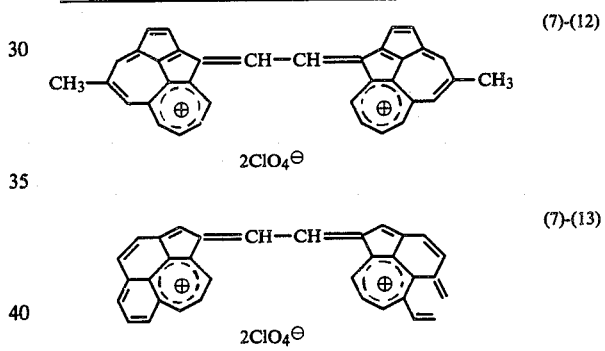
Examples of the compounds having the general formula (14)
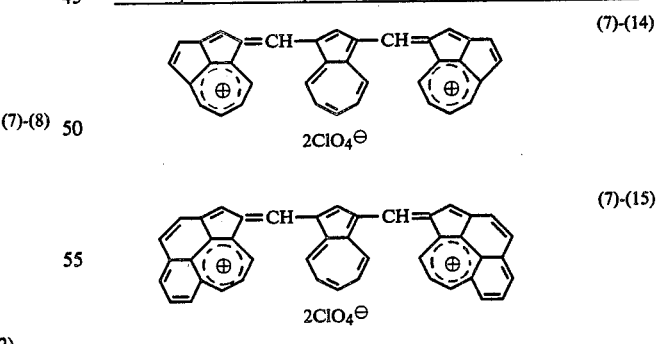
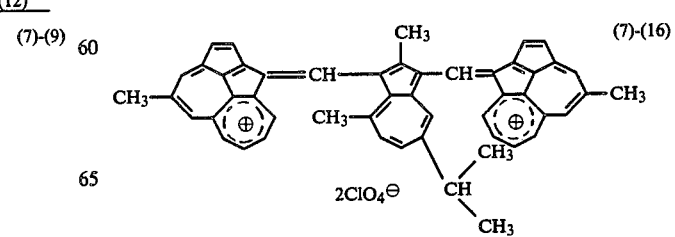

Examples of the compounds having the general formula (15)
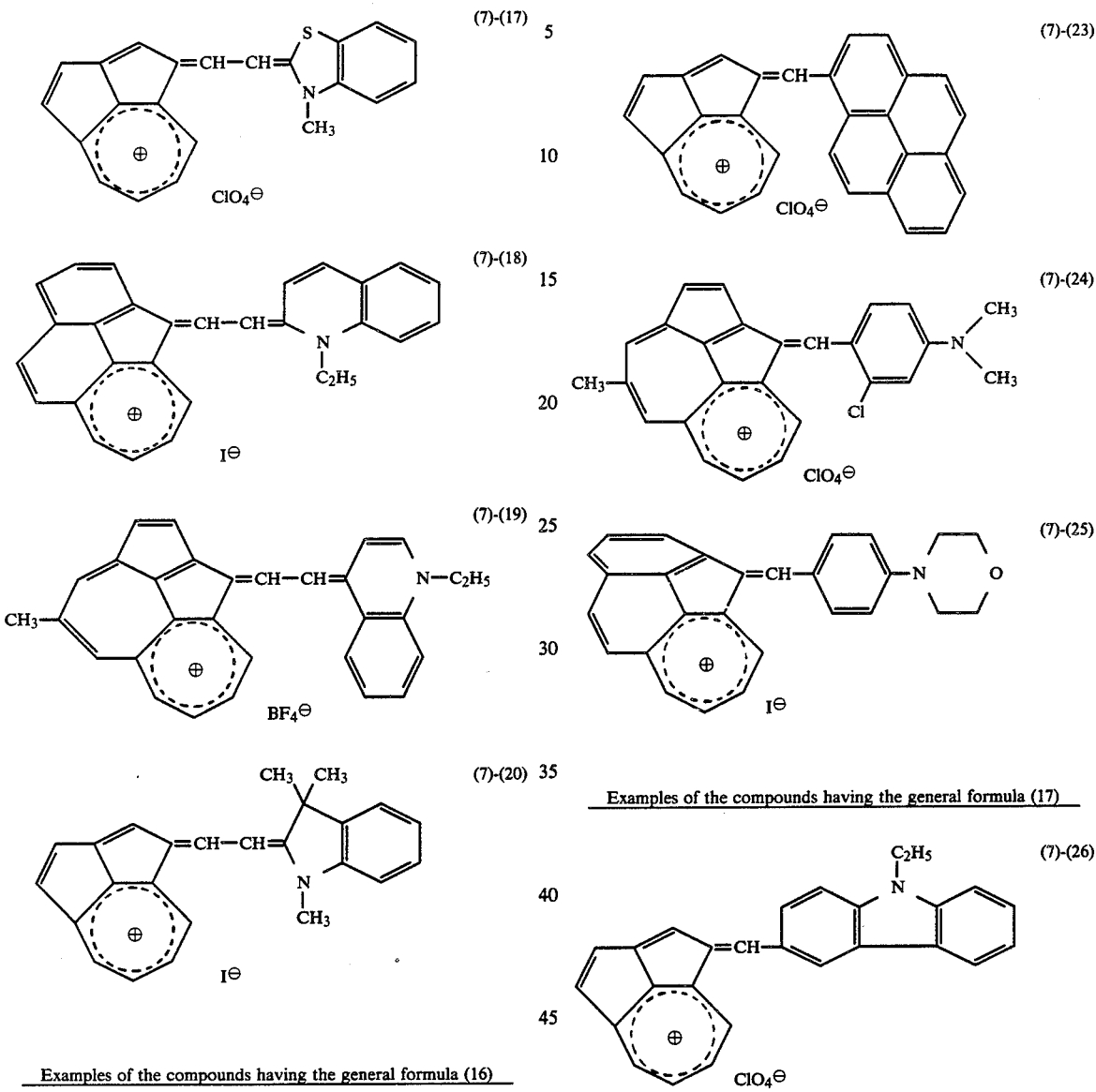
Examples of the compounds having the general formula (16)
Examples of the compounds having the general formula (17)
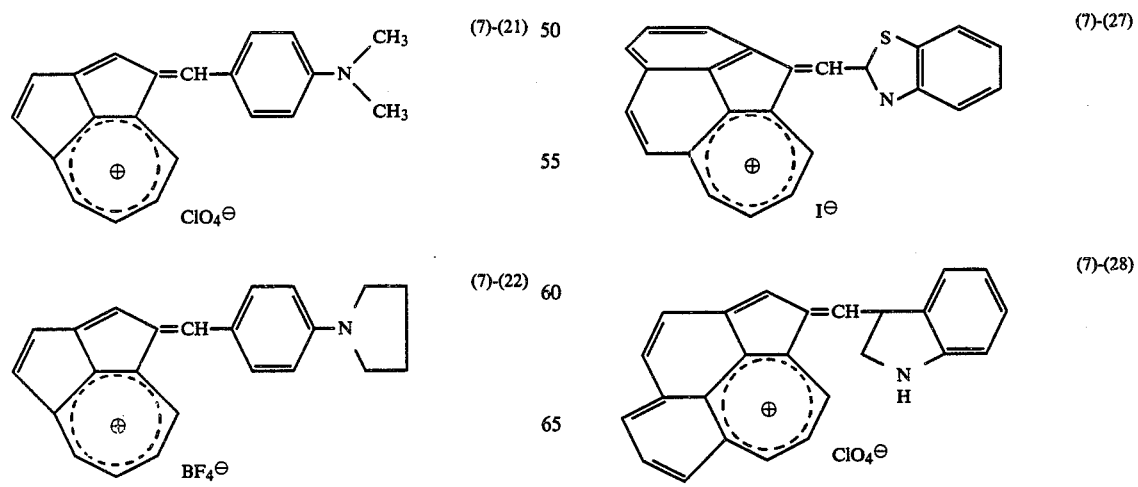

-continued
Examples of the compounds having the general formula (17)
(7)-(29)
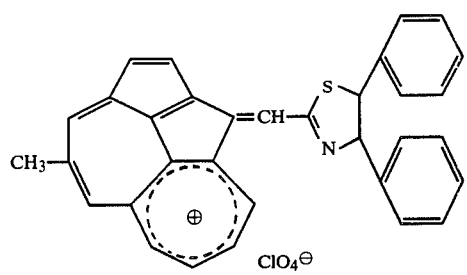
Examples of the compounds having the general formula (18)
(7)-(35)
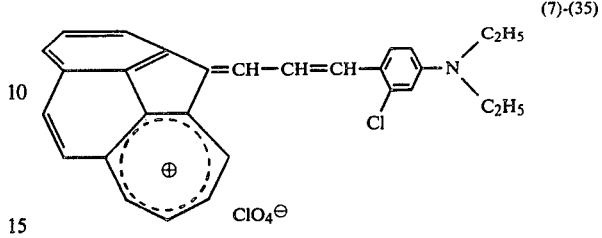
(7)-(36)
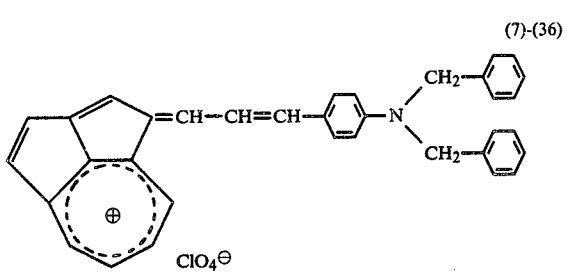
Examples of the compounds having the general formula (18)
(7)-(30)
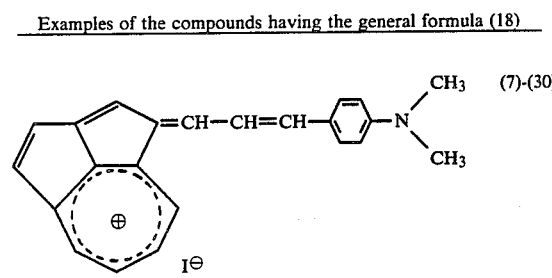
(7)-(31)
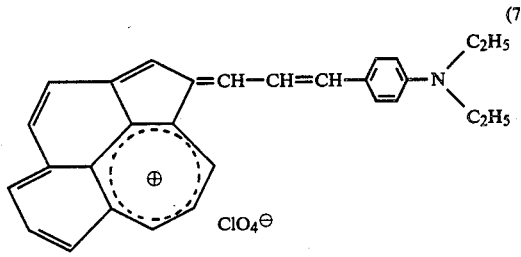
(7)-(37)
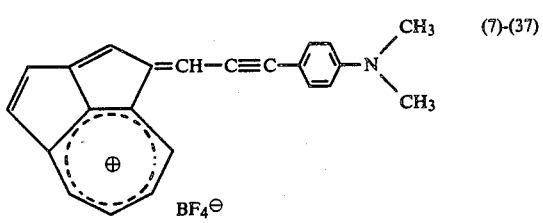
(7)-(32)
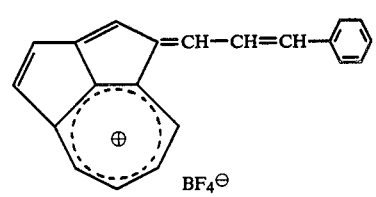
(7)-(38)
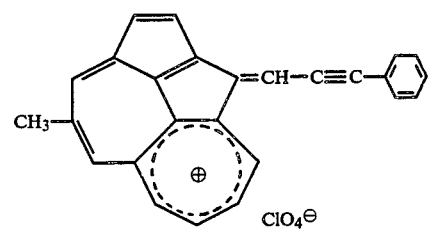
(7)-(33)
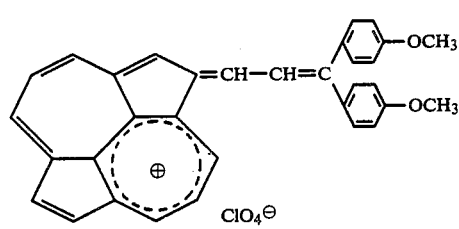
Examples of the compounds having the general formula (20)
(7)-(39)
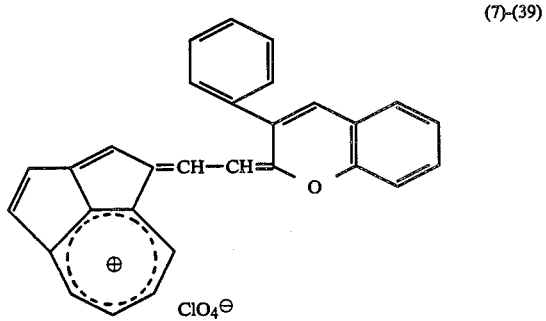
(7)-(34)
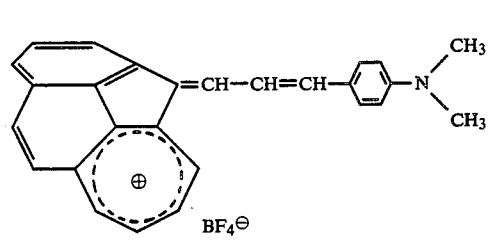

-continued
Examples of the compounds having the general formula (20)

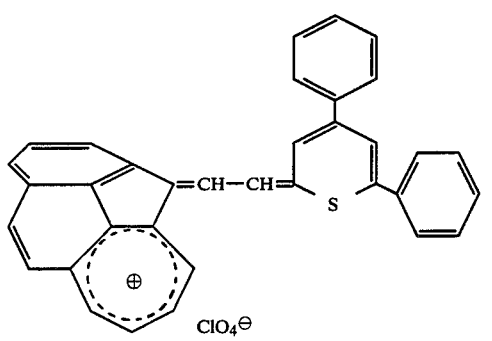
(7)-(40)

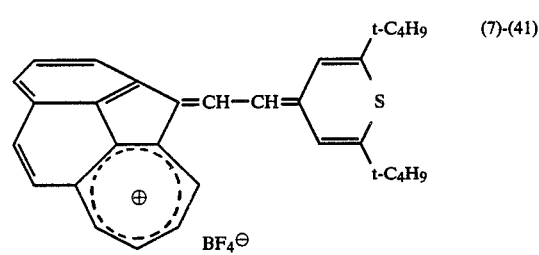
(7)-(41)

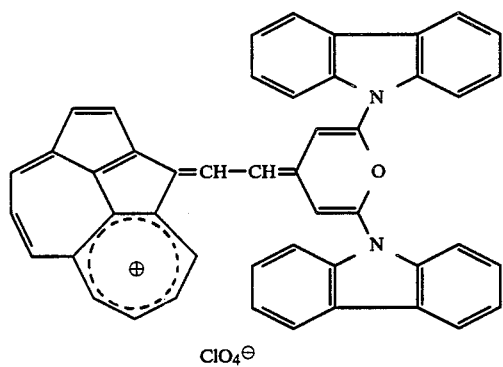
(7)-(42)

The compounds having the general formula (10) or (11) are readily prepared by allowing azulene compounds to react with squaric acid or croconic acid in an appropriate solvent as described in Angew. Chem., Vol. 78 (1966), No. 20, page 937.

The compounds having the general formula (12) wherein $n_3=0$ are prepared by heating a solution of 1-formylazulene compounds and azulene compounds in an appropriate solvent in the presence of strong acids as described in J. Chem. Soc. (1960), page 501, by mixing 1-ethoxymethyleneazulenium salt compounds with azulene compounds in an appropriate solvent as described in ibid. (1961), pages 1724–1730, or by heating a solution of 2-hydroxymethylenecyclohexanone and azulene compounds in an appropriate solvent in the presence of strong acids as described in ibid. (1961), pages 359. Also, the compounds having the general formula (12) wherein $n=1$, $n_3=1$ or 2 are prepared by mixing azulene compounds with malondialdehydes or glutacondialdehydes in an appropriate solvent in the presence of strong acids as described in J. Chem. Soc. (1961), pages 3591–3592.

The compounds having the general formula (13) are readily prepared by heating azulene compounds and glyoxal in the presence of strong acids in an appropriate solvent as described in J. Chem. Soc. (1961), page 3588.

The compounds having the general formula (14) are prepared by heating 1,3-diformylazulene compounds and azulene compounds in the presence of strong acids in an appropriate solvent as described in J. Chem. Soc. (1960), page 501.

The compounds having the general formula (15) are prepared by heating 1-formylazulene compounds and heterocyclic quaternary ammonium salt compounds having active methyl groups in an appropriate solvent as described in J. Chem. Soc., (1961), pages 163–167.

The compounds having the general formula (16), (17), (18) or (19) are prepared by mixing azulene compounds with the corresponding aldehyde compounds in the presence of strong acids in an appropriate solvent as described in J. Chem. Soc. (1958), pages 1110–1117, ibid. (1960), pages 494–501, and ibid. (1961), pages 3579–3593.

The compounds having the general formula (20) are prepared by allowing 1-formylazulene compounds to react in an appropriate solvent with the compounds having a general formula (29):

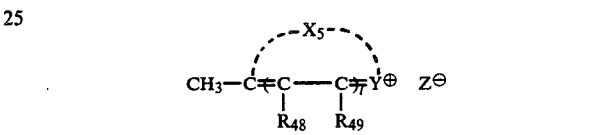

wherein $X_5$, $Y$, $R_{48}$, $R_{49}$, $Z^{\ominus}$ and 1 are as previously defined.

As the reaction solvent, there may be used alcohols such as ethanol, butanol, benzyl alcohol and the like; nitriles such as acetonitrile, propionitrile and the like; organic carboxylic acids such as acetic acid and the like; acid anhydrides such as acetic anhydride and the like; alicyclic ethers such as dioxane, tetrahydrofuran and the like. Also, aromatic hydrocarbons such as benzen and the like may be used by mixed with butanol, benzyl alcohol or the like. The temperature during reaction may be selected from a range of room temperature to the boiling point.

Films containing the above azulenium compounds exhibit photoconductivity and accordingly can be used for the following photosensitive layers of electrophotographic photosensitive members.

In this invention, electrophotographic photosensitive members can be prepared by forming layers of the above azulenium salt compounds on electrically conductive substrates by vacuum deposition or application of a solution or dispersion thereof in a suitable binder.

In preferred embodiments of this invention, the above photoconductive films can be applied as the charge generation layer of an electrophotographic photosensitive member the photosensitive layer of which is functionally devided into a charge generation layer and a charge transport layer.

The charge generation layer is desired to contain the above photoconductive compound as much as possible for the purpose of affording sufficient absorptivity, i.e., absorbing most of the incident light to generate a great number of charge carriers. Additionally, the charge generation layer is desirably as thin as 5μ or less, preferably 0.01–1μ, for the purpose of effective injection of the generated charge carriers into the charge transport layer without substantial deactivation of the carriers due to the recombination or capture (trapping).

The charge generation layer can be formed by applying a solution or dispersion of the above azulenium compound in a suitable binder on a substrate or by forming a deposited film of the compound using a vacuum deposition apparatus. Suitable binders can be selected from a wide variety of insulating resins and from organic photoconductive polymers such as poly(N-vinylcarbazole), polyvinylanthracene, polyvinylpyrene, and the like. Preferred examples of the binder are insulating resins such as poly(vinyl butyral), polyarylates (including a condensation polymer of bisphenol A and phthalic acid), polycarbonates, polyesters, phenoxy resins, poly(vinyl acetate), acrylic resins, polyacrylamides, polyamides, polyvinylpyridine, cellulosic resins, urethane resins, epoxy resins, casein, poly(vinyl alcohol), and polyvinylpyrrolidone. Contents of the binder resin in the charge generation layer are up to 80%, preferably up to 40%, by weight.

Solvents suitable for these resins vary depending upon the kind of resin and are desired to be selected from those not dissolving the charge transport layer(infra) or undercoating layer. As examples of the solvents may be cited alcohols such as methanol, ethanol, isopropanol and the like; ketones such as acetone, methyl ethyl ketone, cyclohexanone and the like; amides such as N,N-dimethylformamide, N,N-dimethylacetamide and the like; sulfoxides such as dimethylsulfoxide and the like; ethers such as tetrahydrofuran, dioxane, ethylene glycol monomethyl ether and the like; esters such as methyl acetate, ethyl acetate and the like; halogenated aliphatic hydrocarbons such as chloroform, methylene chloride, dichloroethylene, carbon tetrachloride, trichloroethylene and the like; and aromatics such as benzene, toluene, xylene, ligroin, monochlorobenzene, dichlorobenzene, and the like.

The coating can be accomplished by dip coating, spray coating, spinner coating, bead coating, Meyer bar coating, blade coating, roller coating, curtain coating and the like. The coating film is dried preferably by heating after the set to touch at room temperature. The heat drying can be performed at 30°–200° C. for 5 minutes to 2 hours with or without blowing air.

The charge transport layer, being electrically in communication with the above-mentioned charge generation layer, has a function of receiving charge carriers from the charge generation layer in an electric field and a function of transporting these charge carriers to its surface. The charge transport layer may be laminated either on the upper side or the lower side (substrate side) of the charge generation layer, but preferably on the upper side.

A material transporting charge carriers in the charge transport layer (hereinafter, simply referred to as "charge-transporting material") is desired to be virtually insensitive to a wavelength of electromagnetic waves to which the charge generation layer is sensitive. The electromagnetic waves herein referred to mean rays of light in a broad sense including γ-rays, X-rays, ultraviolet rays, visible rays, near infrared rays, infrared rays, far infrared rays, etc. When the wavelength region of rays to which the charge transport layer is sensitive agrees or overlaps with that of rays to which the charge generation layer is sensitive, the charge carriers generated in both layers tend to trap each other, thus the sensitivity lowering.

The charge-transporting materials are classified into electron-transporting materials and hole-transporting materials. Electron-transporting materials utilizable in this invention include electron attractive materials, e.g. chloranyl, bromanyl, tetracyanoethylene, tetracyanoquinodimethane, 2,4,7-trinitro-9-fluorenone, 2,4,5,7-tetranitro-9-fluorenone, 2,4,7-trinitro-9-dicyanomethylenefluorenone, 2,4,5,7-tetranitroxanthone, and 2,4,8-trinitrothioxanthone, and their polymeric materials.

Hole-transporting materials utilizable include pyrene, N-ethylcarbazole, N-isopropylcarbazole, N-methyl-N-phenylhydrazino-3-methylidene-9-ethylcarbazole, N,N-diphenylhydrazino-3-methylidene-9-ethylcarbazole, N,N-diphenylhydrazino-3-methylidene-10-ethylphenothiazine, N,N-diphenylhydrazino-3-methylidene-10-ethylphenoxazine; hydrozones such as p-diethylaminobenzaldehyde-N,N-diphenylhydrazone, p-diethylaminobenzaldehyde-N-α-naphthyl-N-phenylhydrazone, p-pyrrolidinylbenzaldehyde-N,N-diphenylhydrozone, 1,3,3-trimethylindolenine-ω-aldehyde-N,N-diphenylhydrazone, and p-diethylaminobenzaldehyde-3-methylbenzthiazolinone-2-hydrazone; 2,5-bis(p-diethylaminophenyl)-1,3,4-oxadiazole; pyrazolines such as 1-phenyl-3-(p-diethylaminostyryl)-5-(p-diethylaminophenyl)pyrazoline, 1-[quinolyl (2)]-3-(p-diethylaminostyryl)-5-(p-diethylaminophenyl)pyrazoline, 1-[pyridyl (2)]-3-(p-diethylaminostyryl)-5-(p-diethylaminophenyl)pyrazoline, 1-[6-methoxypyridyl (2)]-3-(p-diethylaminostyryl)-5-(p-diethylaminophenyl)pyrazoline, 1-[pyridyl (3)]-3-(p-diethylaminostyryl)-5-(p-diethylaminophenyl)pyrazoline, 1-[lepidyl (2)]-3-(p-diethylaminostyryl)-5-(p-diethylaminophenyl)pyrazoline, 1-[pyridyl (2)]-3-(p-diethylaminostyryl)-4-methyl-5-(p-diethylaminophenyl)pyrazoline, 1-[pyridyl (2)]-3-(α-methyl-p-diethylaminostyryl)-5-(p-diethylaminophenyl)pyrazoline, 1-phenyl-3-(p-diethylaminostyryl)-4-methyl-5-(p-diethylaminophenyl)pyrazoline, 1-pnenyl-3-(α-benzyl-p-diethylaminostyryl)-5-(p-diethylaminophenyl)pyrazoline, spiropyrazoline and the like; oxazole compounds such as 2-(p-diethylaminostyryl)-6-diethylaminobenzoxazole, 2-(p-diethylaminophenyl)-4-(p-dimethylaminophenyl-5-(2-chlorophenyl)oxazole and the like; thiazole compounds such as 2-(p-diethylaminostyryl)-6-diethylaminobenzothiazole and the like; triarylmethane compounds such as bis(4-diethylamino-2-methylphenyl)-phenylmethane and the like; polyarylalkanes such as 1,1-bis(4-N,N-diethylamino-2-methylphenyl)heptane, 1,1,2,2-tetrakis (4-N,N-dimethylamino-2-methylphenyl)-ethane and the like; triphenylamine, poly(N-vinylcarbazole), polyvinylpyrene, polyvinylanthracene, polyvinylacridine, poly(9-vinylphenlyanthracene), pyrene-formaldehyde resin, ethylcarbazole-formaldehyde resin and the like.

Besides these organic charge-transporting materials, such inorganic materials can also be used as selenium, selenium-tellurium, amorphous silicon, cadmium sulfide and the like.

These charge-transporting materials can be used singly or in combination of two or more.

When the charge-transporting material employed has no film-forming ability, its coating film can be formed by mixing with a suitable binder. Such binders are insulating resins including, for example, acrylic resins, polyarylates, polyesters, polycarbonates, polystyrene, acrylonitrile-styrene copolymer, acrylonitrile-butadiene copolymer, poly(vinyl butyral), poly(vinyl formal), polysulfone, polyacrylamides, polyamides, chlorinates rubber and the like; and organic photoconductive polymers including, for example, poly(N-vinylcarbazole), polyvinylanthracene, polyvinylpyrene, and the like.

The charge transport layer cannot be made thicker than necessary because the possible charge-carrier transport distance is limited. Its thickness ranges generally from 5 to 30μ, preferably from 8 to 20μ. For forming the charge transport layer by coating, coating methods as cited above can be applied.

The photosensitive layer having a laminate structure comprising such charge generation and charge transport layers as stated above is formed on a substrate having a conductive layer. The substrates having a conductive layer include; sheets or films having conductivity in themselves, such as aluminium, aluminum alloys, copper, zinc, stainless steel, vanadium, molybdenum, chromium, titanium, nickel, indium, gold, platinum and the like; those of plastics [e.g. polyethylene, polypropylene, poly(vinyl chloride), poly(ethylene tetephthalate), acrylic resins, polyfluoroethylene] covered with a film formed by vacuum deposition of aluminum, aluminum alloy, indium oxide, tin oxide, indium oxide-tin oxide alloy, or the like; those of plastics coated with a dispersion of conductive particles (e.g. carbon black or silver particles) in a suitable binder; those of plastics and paper impregnated with conductive particles; and those of conductive polymers.

An undercoating layer having a barrier function and a bonding function can be laid between the conductive layer and the photosensitive layer. The undercoating layer can be formed from casein, poly(vinyl alcohol), nitrocellulose, ethylene-acrylic acid copolymer, polyamides (e.g. nylon 6, nylon 66, nylon 610, nylon copolymer, or alkoxymethylated nylon), polyurethanes, gelatin, aluminum oxide, or the like.

Thickness of the undercoating layer is desirably 0.1-5μ, preferably 0.5-3μ.

When using a photosensitive member comprising a conductive layer, charge generation layer, and charge transport layer laminated in this order, it is necessary to provide positive charge to the surface of the charge transport layer if the this layer is formed from an electron-transporting material. On image exposure of the photosensitive member after the positive charging, electrons generated in the charge generation layer, in the exposed area, are injected into the charge transport layer, then arrive at the surface, and neutralize the positive charges, thus decaying the surface potential and producing an electrostatic contrast to the unexposed area. The thus produced electrostatic latent images, on development with a negative-working toner, turn into visible images. The toner images can be fixed directly or after being transferred to a transfer recording medium such as paper or a plastic film.

It is also possible that the electrostatic latent images on the photosensitive member are transferred to the insulating layer of transfer paper, then developed, and fixed. Any of known developers, development processes, and fixing processes may be adopted, viz. there are no particular restrictions thereupon.

On the other hand, if the charge transport layer is formed from a hole-transporting material, the surface needs to be negatively charged. On image exposure of the photosensitive member after the negative charging, positive holes generated in the charge generation layer, in the exposed area, are injected into the charge transport layer, then arrive at the surface, and neutralize the negative charges, thus decaying the surface potential and producing an electrostatic contrast to the unexposed area. For developing the latent images, it is necessary to use a positive-working toner, contrary to the case where an electron-transporting material is used.

In another embodiment of this invention, the azulenium compound described above can be incorporated as a sensitizer into photosensitive films comprising an organic photoconductive material such as the above-cited hole-transporting material, e.g. hydrazones, pyrazolines, oxazoles, thiazoles, triarylmethanes, polyarylalkanes, triphenylamine, poly(N-vinylcarbazoles), or the like or an inorganic photoconductive material such as zinc oxide, cadmium sulfide, selenium, or the like. These photosensitive films are formed by a coating method from mixtures, containing the azulenium compounds, of the above photoconductive material and a binder.

Any photosensitive member of this invention contains at least one azulenium salt selected from the compounds represented by the general formula (1)–(9) and if necessary, can be improved in sensitivity or made panchromatic by incorporating another photoconductive pigment or dye having a different absorption spectrum.

EXAMPLES 1 TO 63

A solution of casein in aqueous ammonia (casein 11.2 g, 28% aq. ammonia 1 g, water 222 ml) was applied to aluminum sheets by means of a Meyer bar and dried to form an intermediate layer 1.0μ thick on each sheet.

64 kinds of coating dispersions were prepared by adding 5 g each of 64 kinds of azulenium salt compounds shown in the following table to a solution of 2 g of a vinyl butyral resin (degree of butyral conversion 63 mole %) in 95 ml of isopropanol.

After dispersing in an attritor, the coating dispersions were applied separately onto the casein under coat layers by means of a Meyer bar and dried to form charge generation layers each 0.1μ thick.

Then, a solution was prepared by dissolving 5 g of a hydrazone compound represented by the structural formula

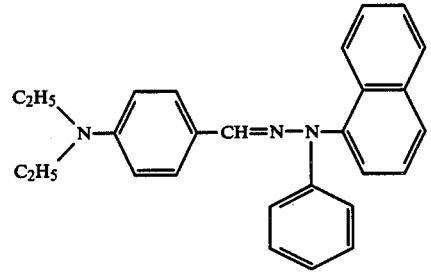

and 5 g of a poly(methyl methacrylate) resin (number average mol. wt. 100,000) in 70 ml of benzene. The solution was applied to the charge generation layers by means of a Meyer bar and dried to form charge transport layers each 12μ thick.

Thus prepared 64 kinds of electrophotographic photosensitive members were corona-charged at −5 KV in the static fashion by using an electrostatic copying paper testing machine (Model SP-428, mfd. by Kawaguchi Denki. Co., Ltd.), were retained for 10 seconds in the dark, and exposed to light at an intensity of 5 lux to examine their charging characteristics. The results are shown in Table 1, wherein Vo is the initial potential of the charged surface, Vk is the potential retention (%) after its decaying for 10 seconds in the dark, and E½ is the exposure quantity for halving the potential after decaying for 10 seconds in the dark.

TABLE 1

| Example No. | Azulenium salt (compound No.) | Vo (−V) | Vk (%) | E½ (lux·sec) |
| --- | --- | --- | --- | --- |
| 1 | (1) - (1) | 540 | 83 | 5.8 |
| 2 | (1) - (2) | 525 | 86 | 3.0 |
| 3 | (1) - (3) | 540 | 80 | 2.7 |
| 4 | (1) - (7) | 570 | 81 | 4.8 |
| 5 | (1) - (9) | 560 | 84 | 8.5 |
| 6 | (1) - (11) | 580 | 83 | 11.5 |
| 7 | (1) - (14) | 530 | 82 | 7.8 |
| 8 | (1) - (16) | 490 | 84 | 8.5 |
| 9 | (1) - (19) | 520 | 85 | 10.3 |
| 10 | (3) - (1) | 540 | 87 | 3.8 |
| 11 | (3) - (2) | 575 | 89 | 5.7 |
| 12 | (3) - (3) | 560 | 81 | 4.6 |
| 13 | (3) - (5) | 540 | 84 | 8.9 |
| 14 | (3) - (6) | 550 | 86 | 11.4 |
| 15 | (3) - (9) | 545 | 78 | 6.4 |
| 16 | (3) - (14) | 515 | 83 | 7.0 |
| 17 | (3) - (16) | 510 | 85 | 14.3 |
| 18 | (3) - (20) | 560 | 84 | 8.7 |
| 19 | (3) - (26) | 570 | 81 | 10.5 |
| 20 | (4) - (1) | 570 | 81 | 5.6 |
| 21 | (4) - (2) | 545 | 84 | 3.2 |
| 22 | (4) - (4) | 520 | 87 | 7.8 |
| 23 | (4) - (6) | 540 | 80 | 10.5 |
| 24 | (4) - (7) | 590 | 83 | 6.5 |
| 25 | (4) - (9) | 525 | 76 | 4.5 |
| 26 | (4) - (10) | 520 | 82 | 13.4 |
| 27 | (4) - (14) | 545 | 80 | 7.2 |
| 28 | (4) - (17) | 560 | 84 | 5.8 |
| 29 | (4) - (20) | 545 | 81 | 12.0 |
| 30 | (5) - (1) | 535 | 81 | 4.2 |
| 31 | (5) - (2) | 475 | 84 | 3.5 |
| 32 | (5) - (3) | 540 | 80 | 6.5 |
| 33 | (5) - (5) | 520 | 86 | 3.1 |
| 34 | (5) - (8) | 560 | 84 | 2.7 |
| 35 | (5) - (9) | 545 | 80 | 7.4 |
| 36 | (5) - (12) | 540 | 83 | 2.4 |
| 37 | (5) - (18) | 530 | 87 | 10.5 |
| 38 | (5) - (20) | 515 | 84 | 13.0 |
| 39 | (6) - (1) | 530 | 81 | 2.3 |
| 40 | (6) - (2) | 545 | 80 | 4.5 |
| 41 | (6) - (3) | 510 | 81 | 2.8 |
| 42 | (6) - (7) | 525 | 83 | 7.8 |
| 43 | (6) - (10) | 570 | 84 | 5.5 |
| 44 | (6) - (14) | 525 | 87 | 10.4 |
| 45 | (6) - (15) | 585 | 85 | 6.4 |
| 46 | (6) - (18) | 540 | 84 | 12.5 |
| 47 | (7) - (1) | 520 | 84 | 7.8 |
| 48 | (7) - (2) | 540 | 80 | 6.5 |
| 49 | (7) - (4) | 570 | 82 | 10.5 |
| 50 | (7) - (7) | 515 | 80 | 17.6 |
| 51 | (7) - (9) | 520 | 80 | 12.7 |
| 52 | (7) - (10) | 520 | 84 | 10.0 |
| 53 | (7) - (12) | 545 | 89 | 11.6 |
| 54 | (7) - (14) | 480 | 90 | 21.5 |
| 55 | (7) - (18) | 510 | 87 | 6.5 |
| 56 | (7) - (21) | 520 | 86 | 4.0 |
| 57 | (7) - (24) | 515 | 84 | 3.7 |
| 58 | (7) - (26) | 560 | 85 | 10.5 |
| 59 | (7) - (30) | 575 | 86 | 2.7 |
| 60 | (7) - (33) | 570 | 84 | 6.8 |
| 61 | (7) - (38) | 580 | 89 | 26.5 |
| 62 | (7) - (40) | 520 | 86 | 4.5 |
| 63 | (7) - (41) | 515 | 84 | 5.8 |

EXAMPLE 64

A coating dispersion was prepared by dissolving 5 g of a polyester resin (Vylon 200, mfd. by Toyobo Co., Ltd.) and 5 g of 1-[pyridyl-(2)]-3-(4-N,N-diethylaminostyryl)-5-(4-N,N-diethylaminophenyl)pyrazoline in 80 ml of methyl ethyl ketone and dispersing 1.0 g of the azulenium salt compound No. (1)-(2) in the solution. The dispersion was applied to an aluminum layer vapor-deposited on a polyester film and was dried to prepare a photosensitive member having a photosensitive layer 13$\mu$ thick.

Charging characteristics of this photosensitive member measured according to the same manner as in Example 1 were as follows:

Vo: −545 V
Vk: 81%
E½: 37.4 lux·sec

EXAMPLES 65–68

Photosensitive members were prepared in the same manner as in Example 64 except that azulenium salt compounds shown in the following Table were used in place of the azulenium salt compound No. (1)-(2) employed in preparing a photosensitive member in Example 64. Charging characteristics of these photosensitive members are shown in Table 2.

TABLE 2

| Example No. | Azulenium salt (compound No.) | Vo (−V) | Vk (%) | E½ (lux·sec) |
| --- | --- | --- | --- | --- |
| 65 | (1) - (1) | −520 | 84 | 40.5 |
| 66 | (1) - (3) | −490 | 82 | 28.4 |
| 67 | (1) - (12) | −480 | 81 | 53.4 |
| 68 | (1) - (20) | −510 | 80 | 61.5 |

EXAMPLE 69

A coating dispersion was prepared by adding 1 g of poly(N-vinylcarbazole) and 5 mg of the azulenium salt compound No. (1)-(1) to 10 g of 1,2-dichloroethane, followed by sufficient stirring. The dispersion was applied by doctor blade coating on an aluminum layer vapor-deposited on a poly(ethylene terephthalate) film and was dried to form an electrophotographic photosensitive layer 15$\mu$ thick.

Charging characteristics of the photosensitive member thus prepared were measured by the same manner as in Example 1. The results were as follows. (positive charging polarity):

Vo: +420 V
Vk: 78%
E½: 24.5 lux·sec

EXAMPLE 70

An electrophotographic photosensitive member was prepared in the same manner as in Example 69 but using the azulenium salt compound No. (1)-(12) in place of No. (1)-(1). Charging characteristics of this photosensitive member were measured. The results were as follows. (positive charging polarity):

Vo: +450 V
Vk: 81%
E½: 57.0 lux·sec

EXAMPLE 71

A coating dispersion was prepared by thoroughly mixing 10 g of finely divided zinc oxide (Sazex 2000, mfd. by Sakai Chem. Ind. Co., Ltd.), 4 g of an acrylic resin (Dianal LR009, mfd. by Mitsubishi Rayon Co., Ltd.), 10 g of toluene, and 10 mg of the azulenium salt compound No. (1)-(2) in a ball mill. The dispersion was applied by doctor blade coating on an aluminum layer vapor-deposited on a poly(ethylene terephthalate) film and was dried to prepare an electrophotographic photosensitive member having a photosensitive layer 21$\mu$ thick.

The spectral sensitivity of this photosensitive member was measured with an electrophotographic spectrograph. The results indicated that this photosensitive layer is sensitive to rays of longer wavelengths as compared with the same zinc oxide layer but not containing such an azulenium salt compound.

EXAMPLE 72

A solution of casein in aqueous ammonia was applied to an 100-$\mu$ aluminum sheet and dried to form a 1.1-$\mu$ undercoat.

A charge-transfer complex was formed by dissolving 5 g of 2,4,7-trinitro-9-fluorenone and 5 g of poly(N-vinylcarbazole) (number-average mol. wt. 300,000) in 70 ml of tetrahydrofuran. This solution and 1 g of the azulenium salt compound No. (1)-(2) were added to a solution of 5 g of a polyester resin (Vylon, mfd. by Toyobo Co., Ltd.) in 70 ml of tetrahydrofuran to form a dispersion, which was applied to the undercoat and dried to form an electrophotographic photosensitive layer 12$\mu$ thick.

Charging characteristics of the photosensitive member thus prepared were measured in the same manner as in Example 1 but by positive charging. The results were as follows:
Vo: +470 V
Vk: 87%
E½: 9.4 lux·sec

EXAMPLE 73

A 1.1-$\mu$ poly(vinyl alcohol) film was formed on an aluminum layer vapor-deposited on a poly(ethylene terephthalate) film.

A coating dispersion containing the azulenium salt compound as shown in Example 2 was applied onto the previously formed poly(vinyl alcohol) layer by means of a Meyer bar and dried to form a charge generation layer 0.1$\mu$ thick.

A solution prepared by dissolving 5 g of a pyrazoline compound represented by the formula

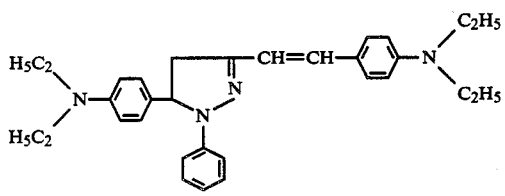

and 5 g of a polyarylate resin (product of polycondensation of bisphenol A and a terephthalic acid-isophthalic acid mixture) in 70 ml of tetrahydrofuran was applied to the charge generation layer and dried to form a charge transport layer 10$\mu$ thick.

Charging characteristics of the photosensitive member thus prepared were measured by the same manner as in Example 1. The results were as follows.
Vo: −520 V
Vk: 87%
E½: 3.5 lux·sec

EXAMPLE 74

A solution of casein in aqueous ammonia (casein 11.2 g, 28% aqueous ammonia 1 g, water 222 ml) was applied to an aluminum cylinder by a dip coating method and dried to form an undercoat layer of 1.0 g/m².

1 wt. parts of the azulenium salt compound No. (1)-(2), 1 wt. part of a butyral resin (S-lec BM-2, mfd. by Sekisui Chem. Co., Ltd.), and 30 wt. parts of isopropyl alcohol were dispersed in a ball mill for 4 hours. The dispersion was applied to the previously formed undercoat by the dip coating method and dried to form a charge generation layer 0.3$\mu$ thick.

A solution was prepared by dissolving 1 wt. part of p-diethylaminobenzaldehyde-N-phenyl-N-$\alpha$-naphthylhydrazone and 1 wt. part of a polysulfone resin (P 1700, mfd. by Union Carbide Corp.) in 6 wt. parts of monochlorobenzene with stirring. The solution was applied to the charge generation layer by the dip coating method and dried to form a charge transport layer 12$\mu$ thick.

The photosensitive member thus prepared was subjected to a corona discharge of −5 KV and the surface potential was measured (an initial potential Vo). Further, this photosensitive member is permitted to stand for 5 second in the dark place and surface potential was measured (a dark decay Vk). The sensitivity was evaluated by measuring the exposure quantity for halving the potential Vk after the dark decay (E ½ microjoule/cm²). In this case, a gallium-aluminum-arsenic semiconductor laser (oscillation wavelength 780 nm) was used as the light source. The results were as follows.
Vo: −570 V
Vk: 84%
E ½: 2.8 microjoule/cm²

EXAMPLES 75-82

Photosensitive members were prepared in the same manner as in Example 74 except that azulenium salt compounds shown in Table 3 were used in place of the azulenium salt compound No. (1)-(2) used in Example 74. Charging characteristics of these photosensitive members are shown in Table 3.

TABLE 3

| Example No. | Azulenium salt (compound No.) | Vo (−V) | Vk (%) | E ½ (μJ/cm²) |
|---|---|---|---|---|
| 75 | (1) - (1) | 520 | 80 | 4.5 |
| 76 | (1) - (4) | 490 | 86 | 3.5 |
| 77 | (1) - (7) | 480 | 85 | 5.4 |
| 78 | (1) - (12) | 530 | 86 | 10.5 |
| 79 | (1) - (13) | 520 | 87 | 3.0 |
| 80 | (1) - (17) | 500 | 84 | 14.0 |
| 81 | (1) - (20) | 480 | 81 | 7.4 |
| 82 | (1) - (22) | 510 | 83 | 6.8 |

EXAMPLE 83

A coating dispersion was prepared by dissolving 5 g of a polyester resin (Vylon 200, mfd. by Toyobo Co., Ltd.) and 5 g of 1-[pyridyl-(2)]-3-(4-N,N-diethylaminostyryl)-5-(4-N,N-diethylaminophenyl)pyrazoline in 80 ml of methyl ethyl ketone and dispersing 1.0 g of the azulenium salt compound No. (3)-(5) in the solution. The dispersion was applied to an aluminum layer vapor-deposited on a polyester film and was dried to prepare a photosensitive member having a photosensitive layer 13$\mu$ thick.

Charging characteristics of this photosensitive member measured according to the same manner as in Example 1 were as follows:
Vo: −470 V
Vk: 76%
E ½: 34.6 lux·sec

EXAMPLES 84–88

Photosensitive members were prepared in the same manner as in Example 83 except that azulenium salt compounds shown in the following Table were used in place of the azulenium salt compound No. (3)-(5) employed in preparing a photosensitive member in Example 83. Charging characteristics of these photosensitive members are shown in Table 4.

TABLE 4

| Example No. | Azulenium salt (compound No.) | Vo (−V) | Vk (%) | E ½ (lux · sec) |
|---|---|---|---|---|
| 84 | (3) - (1) | 430 | 84 | 30.5 |
| 85 | (3) - (3) | 470 | 89 | 27.4 |
| 86 | (3) - (10) | 510 | 74 | 39.5 |
| 87 | (3) - (13) | 440 | 83 | 37.4 |
| 88 | (3) - (20) | 480 | 80 | 50.5 |

EXAMPLE 89

A coating dispersion was prepared by adding 1 g of poly(N-vinylcarbazole) and 5 mg of the azulenium salt compound No. (3)-(4) to 10 g of 1,2-dichloroethane, followed by sufficient stirring. The dispersion was applied by doctor blade coating on an aluminum layer vapor-deposited on a poly(ethylene terephthalate) film and was dried to form an electrophotographic photosensitive layer 15μ thick.

Charging characteristics of the photosensitive member thus prepared were measured by the same manner as in Example 1. The results were as follows: (positive charging polarity):

Vo: +430 V
Vk: 83%
E ½: 32.5 lux·sec

EXAMPLE 90

An electrophotographic photosensitive member was prepared in the same manner as in Example 89 but using the azulenium salt compound No. (3)-(7) in place of No. (3)-(4). Charging characteristics of this photosensitive member were measured. The results were as follows: (positive charging polarity):

Vo: +480 V
Vk: 77%
E ½: 41.5 lux·sec

EXAMPLE 91

A coating dispersion was prepared by thoroughly mixing 10 g of finely divided zinc oxide (Sazex 2000, mfd. by Sakai Chem. Ind. Co., Ltd.), 4 g of an acrylic resin (Dianal LR009, mfd. by Mitsubishi Rayon Co., Ltd.), 10 g of toluene, and 10 mg of the azulenium salt compound No. (3)-(1) in a ball mill. The dispersion was applied by doctor blade coating on an aluminum layer vapor-deposited on a poly(ethylene terephthalate) film and was dried to prepare an electrophotographic photosensitive member having a photosensitive layer 21μ thick.

The spectral sensitivity of this photosensitive member was measured with an electrophotographic spectrograph. The results indicated that this photosensitive layer is sensitive to rays of longer wavelengths as compared with the same zinc oxide layer but not containing such an azulenium salt compound.

EXAMPLE 92

A solution of casein in aqueous ammonia was applied to an 100-μ aluminum sheet and dried to form a 1.1-μ undercoat.

A charge-transfer complex was formed by dissolving 5 g of 2,4,7-trinitro-9-fluorenone and 5 g of poly(N-vinylcarbazole) (number-average mol. wt. 300,000) in 70 ml of tetrahydrofuran. This solution and 1 g of the azulenium salt compound No. (3)-(1) were added to a solution of 5 g of a polyester resin (Vylon, mfd. by Toyobo Co., Ltd.) in 70 ml of tetrahydrofuran to form a dispersion, which was applied to the undercoat and dried to form an electrophotographic photosensitive layer 12μ thick.

Charging characteristics of the photosensitive member thus prepared were measured in the same manner as in Example 1 but by positive charging. The results were as follows:

Vo: +430 V
Vk: 87%
E ½: 7.8 lux·sec

EXAMPLE 93

A 1.1-μ poly(vinyl alcohol) film was formed on an aluminum layer vapor-deposited on a poly(ethylene terephthalate) film.

A coating dispersion containing the azulenium salt compound as shown in Example 10 was applied onto the previously formed poly(vinyl alcohol) layer by means of a Meyer bar and dried to form a charge generation layer 0.1μ thick.

A solution prepared by dissolving 5 g of a pyrazoline compound represented by the formula

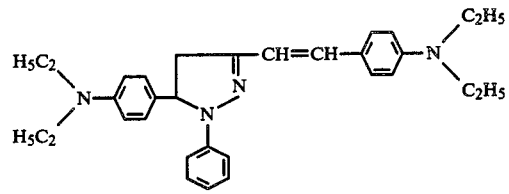

and 5 g of a polyarylate resin (product of polycondensation of bisphenol A and a terephthalic acid-isophthalic acid mixture) in 70 ml of tetrahydrofuran was applied to the charge generation layer and dried to form a charge transport layer 10μ thick.

Charging characteristics of the photosensitive member thus prepared were measured by the same manner as in Example 1. The results were as follows.

Vo: −515 V
Vk: 84%
E ½: 3.8 lux·sec

EXAMPLE 94

A solution of casein in aqueous ammonia (casein 11.2 g, 28% aqueous ammonia 1 g, water 222 ml) was applied to an aluminum cylinder by a dip coating method and dried to form an undercoat layer of 1.0 g/m².

1 wt. part of the azulenium salt compound No. (3)-(5), 1 wt. part of a butyral resin (S-lec BM-2, mfd. by Sekisui Chem. Co., Ltd.), and 30 wt. parts isopropyl alcohol were dispersed in a ball mill for 4 hours. The dispersion was applied to the previously formed undercoat by the dip coating method and dried to form a charge generation layer 0.3μ thick.

A solution was prepared by dissolving 1 wt. part of p-diethylaminobenzaldehyde-N-phenyl-N-α-naphthylhydrazone and 1 wt. part of a polysulfone resin (P 1700, mfd. by Union Carbide Corp.) in 6 wt. parts of monochlorobenzene with stirring. The solution was applied to the charge generation layer by the dip coating method and dried to form a charge transport layer 12μ thick.

The photosensitive member thus prepared was subjected to a corona discharge of −5 KV and the surface potential was measured (an initial potential Vo). Further, this photosensitive member is permitted to stand for 5 seconds in the dark place and the surface potential was measured (a dark decay Vk). The sensitivity was evaluated by measuring the exposure quantity for halving the potential Vk after the dark decay (E ½ microjoule/cm$^2$). In this case, a gallium-aluminum-arsenic semiconductor laser (oscillation wavelength 780 nm) was used as the light source. The results were as follows.

Vo: −530 V
Vk: 81%
E ½: 1.5 microjoule/cm$^2$

EXAMPLES 95-102

Photosensitive members were prepared in the same manner as in Example 94 except that azulenium salt compounds shown in Table 5 were used in place of the azulenium salt compound No. (3)-(5) employed in Example 94. Charging characteristics of these photosensitive members are shown in Table 5.

TABLE 5

| Example No. | Azulenium salt (compound No.) | Vo (−V) | Vk (%) | E ½ (μJ/cm$^2$) |
| --- | --- | --- | --- | --- |
| 95 | (3) - (1) | 480 | 86 | 2.1 |
| 96 | (3) - (3) | 510 | 81 | 3.5 |
| 97 | (3) - (7) | 535 | 83 | 2.4 |
| 98 | (3) - (12) | 520 | 80 | 4.5 |
| 99 | (3) - (15) | 490 | 84 | 8.3 |
| 100 | (3) - (16) | 510 | 83 | 7.4 |
| 101 | (3) - (20) | 520 | 78 | 10.5 |
| 102 | (3) - (22) | 500 | 76 | 14.2 |

EXAMPLE 103

A coating dispersion was prepared by dissolving 5 g of a polyester resin (Vylon 200, mfd. by Toyobo Co., Ltd.) and 5 g of 1-[pyridyl-(2)]-3-(4-N,N-diethylaminostyryl)-5-(4-N,N-diethylaminophenyl)pyrazoline in 80 ml of methyl ethyl ketone and dispersing 1.0 g of the azulenium salt compound No. (4)-(2) in the solution. The dispersion was applied to an aluminum layer vapor-deposited on a polyester film and was dried to prepare a photosensitive member having a photosensitive layer 13μ thick.

Charging characteristics of this photosensitive member measured according to the same manner as in Example 1 were as follows:
Vo: −510 V
Vk: 86%
E ½: 35.8 lux·sec

EXAMPLES 104-109

Photosensitive members were prepared in the same manner as in Example 103 except that azulenium salt compounds shown in the following Table were used in place of the azulenium salt compound No. (4)-(2) employed in preparing a photosensitive member in Example 103. Charging characteristics of these photosensitive members are shown in Table 6.

TABLE 6

| Example No. | Azulenium salt (compound No.) | Vo (−V) | Vk (%) | E ½ (lux · sec) |
| --- | --- | --- | --- | --- |
| 104 | (4) - (1) | 540 | 80 | 29.5 |
| 105 | (4) - (3) | 585 | 84 | 40.5 |
| 106 | (4) - (5) | 560 | 84 | 36.8 |
| 107 | (4) - (8) | 550 | 78 | 45.8 |
| 108 | (4) - (14) | 570 | 76 | 58.0 |
| 109 | (4) - (20) | 575 | 80 | 32.0 |

EXAMPLE 110

A coating dispersion was prepared by adding 1 g of poly(N-vinylcarbazole) and 5 mg of the azulenium salt compound No. (4)-(6) to 10 g of 1,2-dichloroethane, followed by sufficient stirring. The dispersion was applied by doctor blade coating on an aluminum layer vapor-deposited on a poly(ethylene terephthalate) film and was dried to form an electrophotographic photosensitive layer 15μ thick.

Charging characteristics of the photosensitive member thus prepared were measured by the same manner as in Example 1. The results were as follows. (positive charging polarity):
Vo: +470 V
Vk: 89%
E ½: 48.5 lux·sec

EXAMPLE 111

An electrophotographic photosensitive member was prepared in the same manner as in Example 110 but using the azulenium salt compound No. (4)-(17) in place of No. (4)-(6). Charging characteristics of this photosensitive member were measured. The results were as follows. (positive charging polarity):
Vo: +485 V
Vk: 83%
E ½: 41.5 lux·sec

EXAMPLE 112

A coating dispersion was prepared by thoroughly mixing 10 g of finely divided zinc oxide (Sazex 2000, mfd. by Sakai Chem. Ind. Co., Ltd.), 4 g of an acrylic resin (Dianal LR009, mfd. by Mitsubishi Rayon Co., Ltd.), 10 g of toluene, and 10 mg of the azulenium salt compound No. (4)-(2) in a ball mill. The dispersion was applied by doctor blade coating on an aluminum layer vapor-deposited on a poly(ethylene terephthalate) film and was dried to prepare an electrophotographic photosensitive member having a photosensitive layer 21μ thick.

The spectral sensitivity of this photosensitive member was measured with an electrophotographic spectrograph. The results indicated that this photosensitive layer is sensitive to rays of longer wavelengths as compared with the same zinc oxide layer but not containing such an azulenium salt compound.

EXAMPLE 113

A solution of casein in aqueous ammonia was applied to an 100-μ aluminum sheet and dried to form a 1.1-μ undercoat.

A charge-transfer complex was formed by dissolving 5 g of 2,4,7-trinitro-9-fluorenone and 5 g of poly(N-vinylcarbazole) (number-average mol. wt. 300,000) in 70 ml of tetrahydrofuran. This solution and 1 g of the azulenium salt compound No. (4)-(1) were added to a solution of 5 g of a polyester resin (Vylon, mfd. by Toyobo Co., Ltd.) in 70 ml of tetrahydrofuran to form a dispersion, which was applied to the undercoat and dried to form an electrophotographic photosensitive layer 12μ thick.

Charging characteristics of the photosensitive member thus prepared were measured in the same manner as in Example 1 but by positive charging. The results were as follows:

Vo: +520 V
Vk: 74%
E ½: 10.5 lux·sec

EXAMPLE 114

A 1.1-μ poly(vinyl alcohol) film was formed on an aluminum layer vapor-deposited on a poly(ethylene terephthalate) film.

A coating dispersion containing the azulenium salt compound as shown in Example 23 was applied onto the previously formed poly(vinyl alcohol) layer by means of a Meyer bar and dried to form a charge generation layer 0.1μ thick.

A solution prepared by dissolving 5 g of a pyrazoline compound represented by the formula

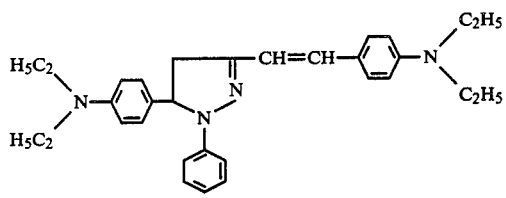

and 5 g of polyarylate (product of polycondensation of bisphenol A and a terephthalic acid-isophthalic acid mixture) in 70 ml of tetrahydrofuran was applied to the charge generation layer and dried to form a charge transport layer 10μ thick.

Charging characteristics of the photosensitive member thus prepared was measured by the same manner as in Example 1. The results were as follows.

Vo: −560 V
Vk: 81%
E ½: 6.5 lux·sec

EXAMPLE 115

A solution of casein in aqueous ammonia (casein 11.2 g, 28% aqueous ammonia 1 g, water 222 ml) was applied to an aluminum cylinder by a dip coating method and dried to form an undercoat layer of 1.0 g/m².

1 wt. part of the azulenium salt compound No. (4)-(2), 1 wt. part of a butyral resin (S-lec BM-2, mfd. by Sekisui Chem. Co., Ltd.), and 30 wt. parts of isopropyl alcohol were dispersed in a ball mill for 4 hours. The dispersion was applied to the previously formed undercoat by the dip coating method and dried to form a charge generation layer 0.3μ thick.

A solution was prepared by dissolving 1 wt. part of p-diethylaminobenzaldehyde-N-phenyl-N-α-naphthylhydrazone and 1 wt. part of a polysulfone resin (P 1700, mfd. by Union Carbide Corp.) in 6 wt. parts of monochlorobenzene with stirring. The solution was applied to the charge generation layer by the dip coating method and dried to form a charge transport layer 12μ thick.

The photosensitive member thus prepared was subjected to a corona discharged of −5 KV and the surface potential was measured (an initial potential Vo). Further, this photosensitive member is permitted to stand for 5 seconds in the dark place and the surface potential was measured (a dark decay Vk). The sensitivity was evaluated by measuring the exposure quantity for halving the potential Vk after the dark decay (E ½ microjoule/cm²). In this case, a gallium-aluminum-arsenic semiconductor laser (oscillation wavelength 780 nm) was used as the light source. The results were as follows.

Vo: −520 V
Vk: 83%
E½: 2.8 microjoule/cm²

EXAMPLES 116-121

Photosensitive members were prepared in the same manner as in Example 115 except that azulenium salt compounds shown in Table 7 were used in place of the azulenium salt compound No. (4)-(2) employed in Example 115. Charging characteristics of these photosensitive members are shown in Table 7.

TABLE 7

| Example No. | Azulenium salt (compound No.) | Vo (−V) | Vk (%) | E ½ (μJ/cm²) |
|---|---|---|---|---|
| 116 | (4) - (1) | 540 | 84 | 3.8 |
| 117 | (4) - (4) | 550 | 81 | 4.5 |
| 118 | (4) - (7) | 570 | 83 | 3.2 |
| 119 | (4) - (12) | 525 | 87 | 5.2 |
| 120 | (4) - (15) | 490 | 89 | 8.4 |
| 121 | (4) - (19) | 510 | 84 | 10.2 |

EXAMPLE 122

A coating dispersion was prepared by dissolving 5 g of a polyester resin (Vylon 200, mfd. by Toyobo Co., Ltd.) and 5 g of 1-[pyridyl-(2)]-3-(4-N,N-diethylaminostyryl)-5-(4-N,N-diethylaminophenyl)pyrazoline in 80 ml of methyl ethyl ketone and dispersion 1.0 g of the azulenium salt compound No. (5)-(1) in the solution. The dispersion was applied to an aluminum layer vapor-deposited on a polyester film and was dried to prepare a photosensitive member having a photosensitive layer 13μ thick.

Charging characteristics of this photosensitive member measured according to the same manner as in Example 1 were as follows:

Vo: −430 V
Vk: 81%
E½: 43.5 lux·sec

EXAMPLES 123-128

Photosensitive members were prepared in the same manner as in Example 122 except that azulenium salt compounds shown in the following Table were used in place of the azulenium salt compound No. (5)-(1) employed in preparing a photosensitive member in Example 122. Charging characteristics of these photosensitive members are shown in Table 8.

TABLE 8

| Example No. | Azulenium salt (compound No.) | Vo (−V) | Vk (%) | E ½ (lux · sec) |
|---|---|---|---|---|
| 123 | (5) - (2) | 490 | 76 | 45.8 |
| 124 | (5) - (4) | 440 | 80 | 36.5 |
| 125 | (5) - (7) | 470 | 83 | 47.2 |
| 126 | (5) - (10) | 510 | 81 | 58.4 |
| 127 | (5) - (20) | 400 | 79 | 35.8 |

TABLE 8-continued

| Example No. | Azulenium salt (compound No.) | Vo (−V) | Vk (%) | E ½ (lux · sec) |
|---|---|---|---|---|
| 128 | (5) - (24) | 525 | 84 | 60.5 |

EXAMPLE 129

A coating dispersion was prepared by adding 1 g of poly(N-vinylcarbazole) and 5 mg of the azulenium salt compound No. (5)-(5) to 10 g of 1,2-dichloroethane, followed by sufficient stirring. The dispersion was applied by doctor blade coating on an aluminum layer vapor-deposited on a poly(ethylene terephthalate) film and was dried to form an electrophotographic photosensitive layer 15μ thick.

Charging characteristics of the photosensitive member thus prepared were measured by the same manner as in Example 1. The results were as follows. (positive charging polarity):
Vo: +510 V
Vk: 79%
E½: 42.5 lux·sec

EXAMPLE 130

An electrophotographic photosensitive member was prepared in the same manner as in Example 129 but using the azulenium salt compound No. (5)-(7) in place of No. (5)-(5). Charging characteristics of this photosensitive member were measured. The results were as follows. (positive charging polarity):
Vo: +520 V
Vk: 83%
E½: 35.4 lux·sec

EXAMPLE 131

A coating dispersion was prepared by thoroughly mixing 10 g of finely divided zinc oxide (Sazex 2000, mfd. by Sakai Chem. Ind. Co., Ltd.), 4 g of an acrylic resin (Dianal LR009, mfd. by Mitsubishi Rayon Co., Ltd.), 10 g of toluene, and 10 mg of the azulenium salt compound No. (5)-(1) in a ball mill. The dispersion was applied by doctor blade coating on an aluminum layer vapor-deposited on a poly(ethylene terephthalate) film and was dried to prepare an electrophotographic photosensitive member having a photosensitive layer 21μ thick.

The spectral sensitivity of this photosensitive member was measured with an electrophotographic spectrograph. The results indicated that this photosensitive layer is sensitive to rays of longer wavelengths as compared with the same zinc oxide layer but not containing such an azulenium salt compound.

EXAMPLE 132

A solution of casein in aqueous ammonia was applied to an 100-μ aluminum sheet and dried to form a 1.1-μ undercoat.

A charge-transfer complex was formed by dissolving 5 g of 2,4,7-trinitro-9-fluorenone and 5 g of poly(N-vinylcarbazole) (number-average mol. wt. 300,000) in 70 ml of tetrahydrofuran. This solution and 1 g of the azulenium salt compound No. (5)-(1) were added to a solution of 5 g of a polyester resin (Vylon, mfd. by Toyobo Co., Ltd.) in 70 ml of tetrahydrofuran to form a dispersion, which was applied to the undercoat and dried to form an electrophotographic photosensitive layer 12μ thick.

Charging characteristics of the photosensitive member thus prepared were measured in the same manner as in Example 1 but by positive charging. The results were as follows:
Vo: +470 V
Vk: 81%
E½: 8.4 lux·sec

EXAMPLE 133

A 1.1-μ poly(vinyl alcohol) film was formed on an aluminum layer vapor-deposited on a poly(ethylene terephthalate) film.

A coating dispersion containing the azulenium salt compound as shown in Example 31 was applied onto the previously formed (vinyl alcohol) layer by means of a Meyer bar and dried to form a charge generation layer 0.1μ thick.

A solution prepared by dissolving 5 g of a pyrazoline compound represented by the formula

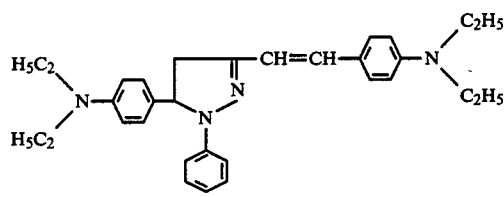

and 5 g of polyarylate (product of polycondensation of bisphenol A and a terephthalic acid-isophthalic acid mixture) in 70 ml of tetrahydrofuran was applied to the charge generation layer and dried to form a charge transport layer 10μ thick.

Charging characteristics of the photosensitive member thus prepared were measured by the same manner as in Example 1. The results were as follows.
Vo: −545 V
Vk: 86%
E½: 46 lux·sec

EXAMPLE 134

A solution of casein in aqueous ammonia (casein 11.2 g, 28% aqueous ammonia 1 g, water 222 ml) was applied to an aluminum cylinder by a dip coating method and dried to form an undercoat layer of 1.0 g/m².

1 wt. part of the azulenium salt compound No. (5)-(1), 1 wt. part of a butyral resin (S-lec BM-2, mfd. by Sekisui Chem. Co., Ltd.), and 30 wt. parts of isopropyl alcohol were dispersed in a ball mill for 4 hours. The dispersion was applied to the previously formed undercoat by the dip coating method and dried to form a charge generation layer 0.3μ thick.

A solution was prepared by dissolving 1 wt. part of p-diethylaminobenzaldehyde-N-phenyl-N-α-naphthyl-hydrazone and 1 wt. part of polysulfone (P 1700, mfd. by Union Carbide Corp.) in 6 wt. parts of monochlorobenzene with stirring. The solution was applied to the charge generation layer by the dip coating method and dried to form a charge transport layer 12μ thick.

The photosensitive member thus prepared was subjected to a corona discharge of −5 KV and the surface potential was measured (an initial potential Vo). Further, this photosensitive member is permitted to stand for 5 seconds in the dark place and the surface potential was measured (a dark decay Vk). The sensitivity was evaluated by measuring the exposure quantity for halving the potential Vk after the dark decay (E½ microjoule/cm$^2$). In this case, a gallium-aluminum-arsenic semiconductor laser (oscillation wavelength 780 nm) was used as the light source. The results were as follows.

Vo: −520 V
Vk: 80%
E½: 2.4 microjoule/cm$^2$

EXAMPLE 135-141

Photosensitive members were prepared in the same manner as in Example 134 except that azulenium salt compounds shown in the following Table were used in place of the azulenium salt compound No. (5)-(1) employed in Example 134. Charging characteristics of these photosensitive members are shown in Table 9.

TABLE 9

| Example No. | Azulenium salt (compound No.) | Vo (−V) | Vk (%) | E½ (μJ/cm$^2$) |
| --- | --- | --- | --- | --- |
| 135 | (5) - (3) | 540 | 84 | 4.1 |
| 136 | (5) - (6) | 520 | 81 | 3.8 |
| 137 | (5) - (10) | 545 | 86 | 5.8 |
| 138 | (5) - (11) | 470 | 76 | 4.6 |
| 139 | (5) - (21) | 480 | 81 | 8.4 |
| 140 | (5) - (23) | 430 | 80 | 11.4 |
| 141 | (5) - (27) | 490 | 83 | 9.4 |

EXAMPLE 142

A coating dispersion was prepared by dissolving 5 g of a polyester regin (Vylon 200, mfd. by Toyobo Co., Ltd.) and 5 g of 1-[pyridyl-(2)]-3-(4-N,N-diethylaminostyryl)-5-(4-N,N-diethylaminophenyl)pyrazoline in 80 ml of methyl ethyl ketone and dispersing 1.0 g of the azulenium salt compound No. (6)-(2) in the solution. The dispersion was applied to an aluminum layer vapor-deposited on a polyester film and was dried to prepare a photosensitive member having a photosensitive layer 13μ thick.

Charging characteristics of this photosensitive member measured according to the same manner as in Example 1 were as follows:

Vo: −480 V
Vk: 81%
E½: 38.5 lux·sec

EXAMPLES 143-147

Photosensitive members were prepared in the same manner as in Example 142 except that azulenium salt compounds shown in the following Table were used in place of the azulenium salt compound No. (6)-(2) employed in preparing a photosensitive member in Example 142. Charging characteristics of these photosensitive members are shown in Table 10.

TABLE 10

| Example No. | Azulenium salt (compound No.) | Vo (−V) | Vk (%) | E½ (lux · sec) |
| --- | --- | --- | --- | --- |
| 143 | (6) - (1) | 510 | 81 | 25.9 |
| 144 | (6) - (5) | 485 | 84 | 40.5 |
| 145 | (6) - (6) | 520 | 87 | 56.8 |
| 146 | (6) - (8) | 510 | 80 | 35.5 |
| 147 | (6) - (16) | 505 | 83 | 41.6 |

EXAMPLE 148

A coating dispersion was prepared by adding 1 g of poly(N-vinylcarbazole) and 5 mg of the azulenium salt compound No. (6)-(2) to 10 g of 1,2-dichloroethane, followed by sufficient stirring. The dispersion was applied by doctor blade coating on an aluminum layer vapor-deposited on a poly(ethylene terephthalate) film and was dried to form an electrophotographic photosensitive layer 15μ thick.

Charging characteristics of the photosensitive member thus prepared were measured by the same manner as in Example 1. The results were as follows: (positive charging polarity):

Vo: +520 V
Vk: 80%
E½: 37.5 lux·sec

EXAMPLE 149

An electrophotographic photosensitive member was prepared in the same manner as in Example 148 but using the azulenium salt compound No. (6)-(7) in place of No. (6)-(2). Charging characteristics of this photosensitive member were measured. The results were as follows. (positive charging polarity):

Vo: +470 V
Vk: 78%
E½: 42.5 lux·sec

EXAMPLE 150

A coating dispersion was prepared by thoroughly mixing 10 g of finely divided zinc oxide (Sazex 2000, mfd. by Sakai Chem. Ind. Co., Ltd.), 4 g of an acrylic resin (Dianal LR009, mfd. by Mitsubishi Rayon Co., Ltd.), 10 g of toluene, and 10 mg of the azulenium salt compound No. (6)-(1) in a ball mill. The dispersion was applied by doctor blade coating on an aluminum layer vapor-deposited on a poly(ethylene terephthalate) film and was dried to prepare an electrophotographic photosensitive member having a photosensitive layer 21μ thick.

The spectral sensitivity of this photosensitive member was measured with an electrophotographic spectrograph. The results indicated that this photosensitive layer is sensitive to rays of longer wavelengths as compared with the same zinc oxide layer but not containing such an azulenium salt compound.

EXAMPLE 151

A solution of casein in aqueous ammonia was applied to an 100-μ aluminum sheet and dried to form a 1.1-μ undercoat.

A charge-transfer complex was formed by dissolving 5 g of 2,4,7-trinitro-9-fluorenone and 5 g of poly(N-vinylcarbazole) (number-average mol. wt. 300,000) in 70 ml of tetrahydrofuran. This solution and 1 g of the azulenium salt compound No. (6)-(4) were added to a solution of 5 g of a polyester resin (Vylon, mfd. by Toyobo Co., Ltd.) in 70 ml of tetrahydrofuran to form a dispersion, which was applied to the undercoat and dried to form an electrophotographic photosensitive layer 12μ thick.

Charging characteristics of the photosensitive member thus prepared were measured in the same manner as in Example 1 but by positive charging. The results were as follows:

Vo: +460 V
Vk: 82%
E½: 12.5 lux·sec

EXAMPLE 152

A 1.1-μ poly(vinyl alcohol) film was formed on an aluminum layer vapor-deposited on a poly(ethylene terephthalate) film.

A coating dispersion containing the azulenium salt compound as shown in Example 41 was applied onto the previously formed poly(vinyl alcohol) layer by means of a Meyer bar and dried to form a charge generation layer 0.1μ thick.

A solution prepared by dissolving 5 g of a pyrazoline compound represented by the formula

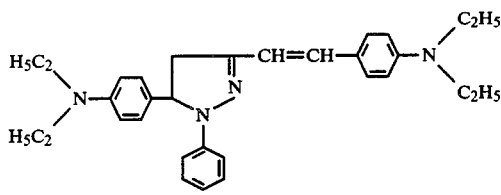

and 5 g of polyarylate (product of polycondensation of bisphenol A and a terephthalic acid-isophthalic acid mixture) in 70 ml of tetrahydrofuran was applied to the charge generation layer and dried to form a charge transport layer 10μ thick.

Charging characteristics of the photosensitive member thus prepared were measured by the same manner as in Example 1. The results were as follows.
Vo: −520 V
Vk: 84%
E½: 3.2 lux·sec

EXAMPLE 153

A solution of casein in aqueous ammonia (casein 11.2 g, 28% aqueous ammonia 1 g, water 222 ml) was applied to an aluminum cylinder by a dip coating method and dried to form an undercoat layer of 1.0 g/m².

1 wt. part of the azulenium salt compound No. (6)-(2), 1 wt. part of a butyral resin (S-lec BM-2, mfd. by Sekisui Chem. Co., Ltd.), and 30 wt. parts of isopropyl alcohol were dispersed in a ball mill for 4 hours. The dispersion was applied to the previously formed undercoat by the dip coating method and dried to form a charge generation layer 0.3μ thick.

A solution was prepared by dissolving 1 wt. part of p-diethylaminobenzaldehyde-N-phenyl-N-α-naphthylhydrazone and 1 wt. part of polysulfone (P 1700, mfd. by Union Carbide Corp.) in 6 wt. parts of monochlorobenzene with stirring. The solution was applied to the charge generation layer by the dip coating method and dried to form a charge transport layer 12μ thick.

The photosensitive member thus prepared was subjected to a corona discharge of −5 KV and the surface potential was measured (an initial potential Vo). Further, this photosensitive member in permitted to stand for 5 seconds in the dark place and the surface potential was measured (a dark decay Vk). The sensitivity was evaluated by measuring the exposure quantity for having the potential Vk after the dark decay (E½ microjoule/cm²). In this case, a gallium-aluminum-arsenic semiconductor laser (oscillation wavelength 780 nm) was used as the light source. The results were as follows.
Vo: −540 v
Vk: 86%
E½: 3.2 microjoule/cm²

EXAMPLES 154-157

Photosensitive members were prepared in the same manner as in Example 153 except that azulenium salt compounds shown in the following Table were used in place of the azulenium salt compound No. (6)-(2) employed in Example 153. Charging characteristics of these photosensitive members are shown in Table 11.

TABLE 11

| Example No. | Azulenium salt (compound No.) | Vo (−V) | Vk (%) | E½ (μJ/cm²) |
|---|---|---|---|---|
| 154 | (6) - (1) | 550 | 81 | 2.1 |
| 155 | (6) - (6) | 530 | 74 | 6.8 |
| 156 | (6) - (9) | 545 | 83 | 4.5 |
| 157 | (6) - (17) | 560 | 82 | 3.4 |

EXAMPLE 158

A coating dispersion was prepared by dissolving 5 g of a polyester resin (Vylon 200, mfd. by Toyobo Co., Ltd.) and 5 g of 1-[pyridyl-(2)]-3-(4-N,N-diethylaminostyryl)-5-(4-N,N-diethylaminophenyl)pyrazoline in 80 ml of methyl ethyl ketone and dispersing 1.0 g of the azulenium salt compound No. (7)-(25) in the solution. The dispersion was applied to an aluminum layer vapor-deposited on a polyester film and was dried to prepare a photosensitive member having a photosensitive layer 13μ thick.

Charging characteristics of this photosensitive member were as follows:
Vo: −560 V
Vk: 84%
E½: 42.0 lux·sec

EXAMPLES 159-169

Photosensitive members were prepared in the same manner as in Example 158 except that azulenium salt compounds shown in the following Table were used in place of the azulenium salt compound No. (7)-(25) employed in preparing a photosensitive member in Example 158. Charging characteristics of these photosensitive members are shown in Table 12.

TABLE 12

| Example No. | Azulenium salt (compound No.) | Vo (−V) | Vk (%) | E½ (lux · sec) |
|---|---|---|---|---|
| 159 | (7) - (1) | 515 | 83 | 35.4 |
| 160 | (7) - (3) | 460 | 87 | 26.8 |
| 161 | (7) - (10) | 570 | 86 | 64.0 |
| 162 | (7) - (13) | 520 | 89 | 57.4 |
| 163 | (7) - (16) | 500 | 86 | 84.0 |
| 164 | (7) - (19) | 545 | 84 | 41.5 |
| 165 | (7) - (22) | 530 | 87 | 31.5 |
| 166 | (7) - (27) | 435 | 80 | 46.8 |
| 167 | (7) - (30) | 505 | 84 | 20.5 |
| 168 | (7) - (37) | 475 | 78 | 31.0 |
| 169 | (7) - (39) | 480 | 80 | 42.1 |

EXAMPLE 170

A coating dispersion was prepared by adding 1 g of poly(N-vinylcarbazole) and 5 mg of the azulenium salt compound No. (7)-(24) to 10 g of 1,2-dichloroethane, followed by sufficient stirring. The dispersion was applied by doctor blade coating on an aluminum layer vapor-deposited on a poly(ethylene terephthalate) film and was dried to form an electrophotographic photosensitive layer 15μ thick.

Charging characteristics of the photosensitive member thus prepared were measured by the same manner as in Example 1. The results were as follows. (positive charging polarity):
Vo +420 v
Vk 78%
E½45.8 lux·sec

EXAMPLE 171

An electrophotographic photosensitive member was prepared in the same manner as in Example 170 but using the azulenium salt compound No. (7)-(1) in place of No. (7)-(24). Charging characteristics of this photosensitive member were measured. The results were as follows. (positive charging polarity):

Vo +490 V
Vk 82%
E½ 29.8 lux·sec

EXAMPLE 172

A coating dispersion was prepared by thoroughly mixing 10 g of finely divided zinc oxide (Sazex 2000, mfd. by Sakai Chem. Ind. Co., Ltd.), 4 g of an acrylic resin (Dianal LR009, mfd. by Mitsubishi Rayon Co., Ltd.), 10 g of toluene, and 10 mg of the azulenium salt compound No. (7)-(24) in a ball mill. The dispersion was applied by doctor blade coating on an aluminum layer vapor-deposited on a poly(ethylene terephthalate) film and was dried to prepare an electrophotographic photosensitive member having a photosensitive layer 21µ thick.

The spectral sensitivity of this photosensitive member was measured with an electrophotographic spectrograph. The results indicated that this photosensitive layer is sensitive to rays of longer wavelengths as compared with the same zinc oxide layer but not containing such an azulenium salt compound.

EXAMPLE 173

A solution of casein in aqueous ammonia was applied to an 100-µ aluminum sheet and dried to form a 1.1-µ undercoat.

A charge-transfer complex was formed by dissolving 5 g of 2,4,7-trinitro-9-fluorenone and 5 g of poly(N-vinylcarbazole) (number-average mol. wt. 300,000) in 70 ml of tetrahydrofuran. This solution and 1 g of the azulenium salt compound No. (7)-(31) were added to a solution of 5 g of a polyester resin (Vylon, mfd. by Toyobo Co., Ltd.) in 70 ml of tetrahydrofuran to form a dispersion, which was applied to the undercoat and dried to form an electrophotographic photosensitive layer 12µ thick.

Charging characteristics of the photosensitive member thus prepared were measured in the same manner as in Example 1 but by positive charging. The results were as follows:

Vo +430 V
Vk 83%
E½ 7.5 lux·sec

EXAMPLE 174

A 1.1-µ poly(vinyl alcohol) film was formed on an aluminum layer vapor-deposited on a poly(ethylene terephthalate) film.

A coating dispersion containing the azulenium salt compound as shown in Example 59 was applied onto the previously formed poly(vinyl alcohol) layer by means of a Meyer bar and dried to form a charge generation layer 0.1µ thick.

A solution prepared by dissolving 5 g of a pyrazoline compound represented by the formula

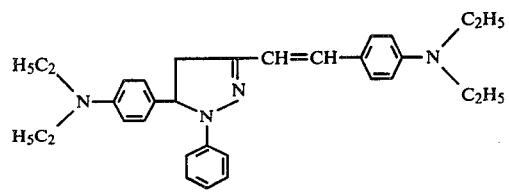

and 5 g of a polyarylate resin (product of polycondensation of bisphenol A and a terephthalic acid-isophthalic acid mixture) in 70 ml of tetrahydrofuran was applied to the charge generation layer and dried to form a charge transport layer 10µ thick.

Charging characteristics of the photosensitive member thus prepared were measured by the same manner as in Example 1. The results were as follows.

Vo −545 V
Vk 87%
E½ 3.4 lux·sec

EXAMPLE 175

A solution of casein in aqueous ammonia (casein 11.2 g, 28% aqueous ammonia 1 g, water 222 ml) was applied to an aluminum cylinder by a dip coating method and dried to form an undercoat layer of 1.0 g/m².

1 wt. part of the azulenium salt compound No. (7)-(30), 1 wt. part of a butyral resin (S-lec BM-2, mfd. by Sekisui Chem. Co., Ltd.), and 30 wt. parts of isopropyl alcohol were dispersed in a ball mill for 4 hours. The dispersion was applied to the previously formed undercoat by the dip coating method and dried to form a charge generation layer 0.3µ thick.

A solution was prepared by dissolving 1 wt. part of p-diethylaminobenzaldehyde-N-phenol-N-α-naphthylhydrazone and 1 wt. part of a polysulfone resin (P 1700, mfd. by Union Carbide Corp.) in 6 wt. parts of monochlorobenzene with stirring. The solution was applied to the charge generation layer by the dip coating method and dried to form a charge transport layer 12µ thick.

The photosensitive member thus prepared was subjected to a corona discharge of −5 KV and the surface potential was measured (an initial potential Vo). Further, this photosensitive member is permitted to stand for 5 seconds in the dark place and the surface potential was measured (a dark decay Vk). The sensitivity was evaluated by measuring the exposure quantity for halving the potential Vk after the dark decay (E½ microjoule/cm²). In this case, a gallium-aluminum-arsenic semiconductor laser (oscillation wavelength 780 nm) was used as the light source. The results were as follows.

Vo −540 V
Vk 87%
E½ 2.0 microjoule/cm²

EXAMPLES 176–185

Photosensitive members were prepared in the same manner as in Example 175 except that azulenium salt compounds shown in Table 13 were used in place of the azulenium salt compound No. (7)-(30) employed in Example 175. Charging characteristics of these photosensitive members are shown in Table 13.

TABLE 13

| Example No. | Azulenium salt (compound No.) | Vo (−V) | Vk (%) | E ½ (μJ/cm²) |
|---|---|---|---|---|
| 176 | (7) - (1) | 570 | 83 | 3.8 |
| 177 | (7) - (5) | 510 | 87 | 4.7 |
| 178 | (7) - (10) | 560 | 80 | 10.5 |
| 179 | (7) - (16) | 490 | 79 | 7.8 |
| 180 | (7) - (17) | 520 | 82 | 18.4 |
| 181 | (7) - (22) | 515 | 81 | 13.0 |
| 182 | (7) - (29) | 545 | 79 | 6.4 |
| 183 | (7) - (34) | 525 | 81 | 4.6 |
| 184 | (7) - (38) | 520 | 84 | 15.6 |
| 185 | (7) - (42) | 540 | 80 | 5.8 |

What is claimed is:

1. A photoconductive member which comprises an electroconductive substrate and at least one of the azulenium salt compounds represented by the formulae (1)-(9) as shown below;

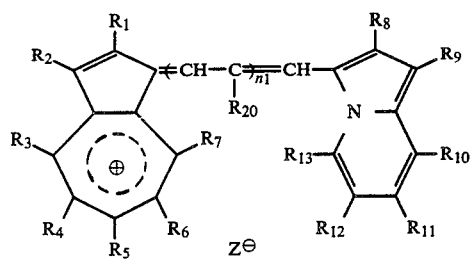

(1)

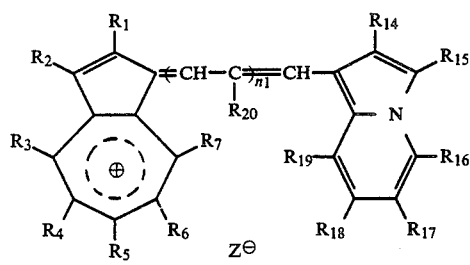

(2)

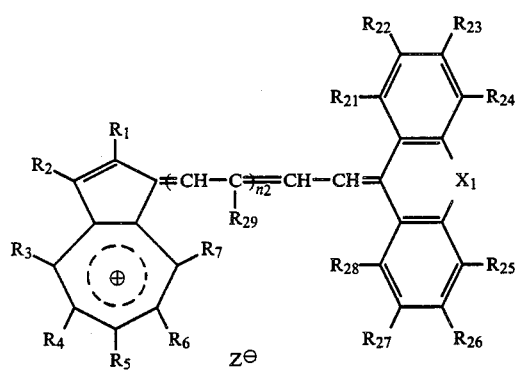

(3)

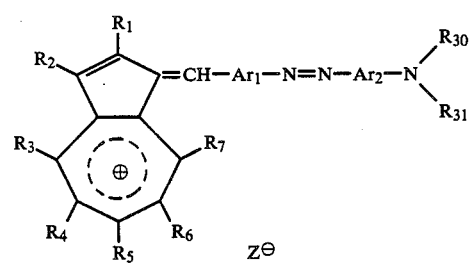

(4)

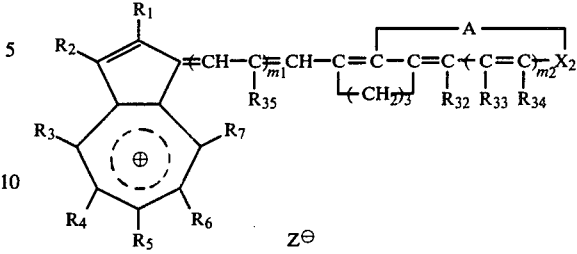

(5)

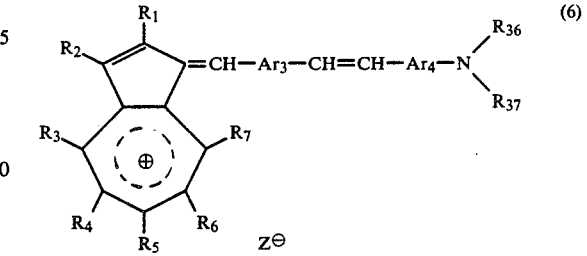

(6)

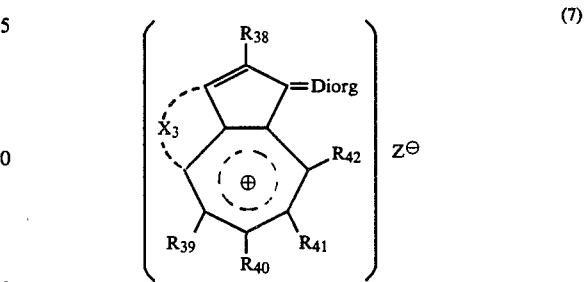

(7)

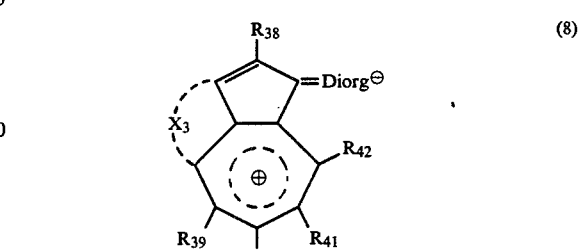

(8)

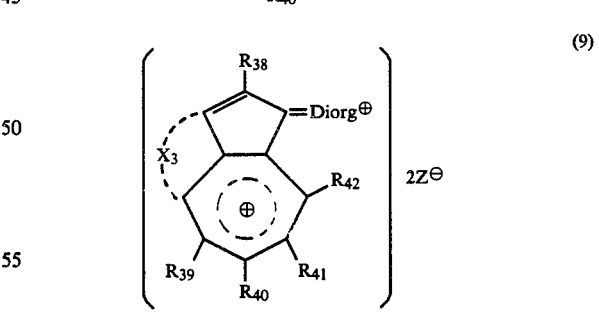

(9)

wherein each of $R_1$, $R_2$, $R_3$, $R_4$, $R_5$, $R_6$, and $R_7$ is hydrogen, halogen, or an organic monovalent residue and at least one of the combinations ($R_1$ and $R_2$), ($R_2$ and $R_3$), ($R_3$ and $R_4$), ($R_4$ and $R_5$), ($R_5$ and $R_6$) and ($R_6$ and $R_7$) may form a substituted or unsubstituted condensed ring;

each of $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ is hydrogen, halogen, alkyl, alkoxy, substituted or unsubstituted aryl, substituted or unsubstituted aralkyl, nitro, or acryl and at least one of the combinations ($R_8$ and $R_9$), ($R_9$ and $R_{10}$), ($R_{10}$ and $R_{11}$), ($R_{11}$ and $R_{12}$), ($R_{12}$ and $R_{13}$), ($R_{14}$ and $R_{15}$), ($R_{15}$ and $R_{16}$), ($R_{16}$ and $R_{17}$), ($R_{17}$ and $R_{18}$), and ($R_{18}$ and $R_{19}$) may form a substituted or unsubstituted condensed ring;

$R_{20}$ is hydrogen, nitro, alkyl, or aryl;

$n_1$ is 0, 1, or 2;

each of $R_{21}$, $R_{22}$, $R_{23}$, $R_{24}$, $R_{25}$, $R_{26}$, $R_{27}$, and $R_{28}$ is hydrogen, halogen, alkyl, alkoxy, hydroxyl, substituted or unsubstituted aryl, substituted or unsubstituted aralkyl, or nitro, and at least one of the combinations ($R_{21}$ and $R_{22}$), ($R_{22}$ and $R_{23}$), ($R_{23}$ and $R_{24}$), ($R_{25}$ and $R_{26}$), ($R_{26}$ and $R_{27}$) and ($R_{27}$ and $R_{28}$) may form a substituted or unsubstituted aromatic ring;

$X_1$ is oxygen, sulfur, or selenium;

$R_{29}$ is hydrogen, nitro, cyano, alkyl, or aryl;

$n_2$ is 0, 1, or 2;

each of $R_{30}$ and $R_{31}$ is substituted or unsubstituted alkyl, aryl or aralkyl, and $R_{30}$ and $R_{31}$ may be joined together with the nitrogen atom to which they are attached to form a ring;

each of $Ar_1$ and $Ar_2$ is substituted or unsubstituted arylene;

each of $R_{32}$, $R_{33}$, and $R_{34}$ is hydrogen, alkyl, alkoxy, substituted or unsubstituted aryl, substituted or unsubstituted styryl, substituted or unsubstituted 4-phenyl-1,3-butadienyl, or a substituted or unsubstituted heterocyclic ring group and the combination ($R_{32}$ and $R_{33}$) or ($R_{33}$ and $R_{34}$) may form a substituted or unsubstituted benzene ring;

$R_{35}$ is hydrogen, nitro, alkyl, or aryl;

$X_2$ is oxygen, sulfur, or selenium;

A is an atomic group necessary to complete pyran, thiapyran, selenapyran, benzopyran, benzothiapyran, benzoselenapyran, naphthopyran, naphthothiapyran, or naphthoselenapyran which may be substituted;

$m_1$ is 0, 1, or 2;

$m_2$ is 0, or 1;

each of $R_{36}$ and $R_{37}$ is substituted or unsubstituted alkyl, aryl, or aralkyl, and $R_{36}$ and $R_{37}$ may be joined together with the nitrogen atom to which they are attached to form a ring;

each of $Ar_3$ and $Ar_4$ is substituted or unsubstituted arylene;

each of $R_{38}$, $R_{39}$, $R_{40}$, $R_{41}$, and $R_{42}$ is hydrogen, halogen, or an organic monovalent residue;

$X_3$ is an atomic group necessary to form a substitued or unsubstituted, 5-, 6-, or 7-membered aromatic ring;

at least one of the combinations ($R_{38}$ and an aromatic ring formed by $X_3$), (an aromatic ring formed by $X_3$ and $R_{39}$), ($R_{39}$ and $R_{40}$), ($R_{40}$ and $R_{41}$), and ($R_{41}$ and $R_{42}$) may form a substituted or unsubstituted aromatic ring, heterocyclic ring or aliphatic ring;

Diorg is an organic divalent residue linked with a double bond;

$Z^\ominus$ is an anionic residue.

2. A photoconductive film according to claim 1, wherein the azulenium salt compounds represented by the formulae (7)-(9) are the compounds represented by the formulae (10)-(20) as shown below;

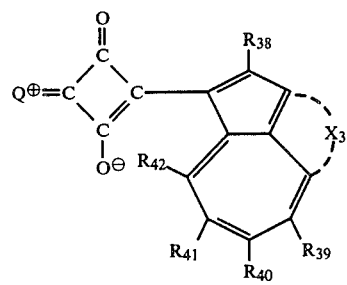
(10)

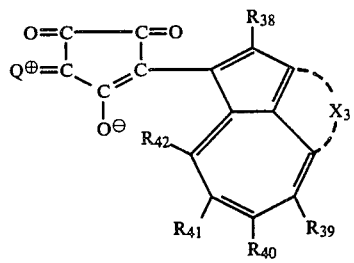
(11)

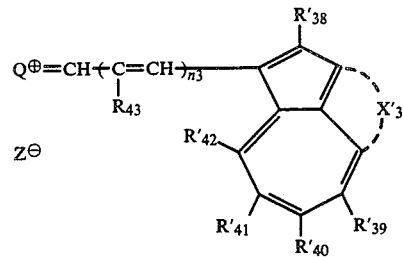
(12)

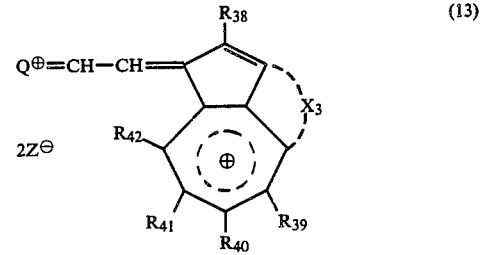
(13)

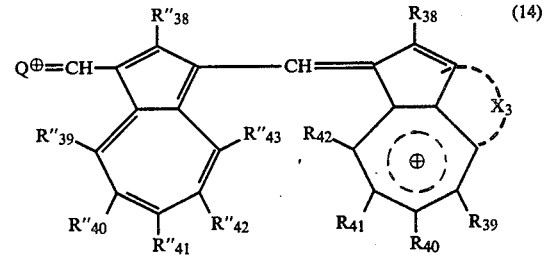
(14)

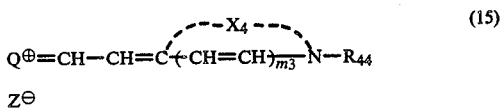
(15)

(16)

(17)

-continued $$Q^{\oplus}=CH-CH=\underset{\underset{R_{47}}{|}}{C}-R_{45} \quad Z^{\ominus} \qquad (18)$$

$$Q^{\oplus}=CH-C\equiv C-R_{45} \quad Z^{\ominus} \qquad (19)$$

$$Q^{\oplus}=CH-CH=C\underset{\underset{R_{48}}{|}}{\overset{\overset{X_{5}}{\frown}}{C}}=\underset{\underset{R_{49}}{|}}{C}\!\!\!\nmid_{l}Y \quad Z^{\ominus} \qquad (20)$$

wherein
$Q^{\oplus}$ is

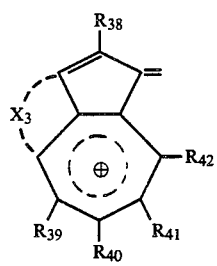

each of $R_{38}$, $R_{39}$, $R_{40}$, $R_{41}$, and $R_{42}$ is hydrogen, halogen or an organic monovalent residue;

$X_3$ is an atomic group necessary to form a substituted or unsubstituted 5-, 6-, or 7-membered aromatic ring;

at least one of the combinations ($R_{38}$ and an aromatic ring formed by $X_3$), (an aromatic ring formed by $X_3$ and $R_{39}$), ($R_{39}$ and $R_{40}$), ($R_{40}$ and $R_{41}$), and ($R_{41}$ and $R_{42}$) may form a substituted or unsubstituted aromatic ring, heterocyclic ring or aliphatic ring;

each of $R'_{38}$, $R'_{39}$, $R'_{40}$, $R'_{41}$, and $R'_{42}$ is hydrogen, halogen or an organic monovalent residue;

$X'_3$ is an atomic group necessary to form a substituted or unsubstituted (5-, 6-, or 7-membered aromatic ring);

at least one of the combinations ($R'_{38}$ and an aromatic ring formed by $X'_3$), (an aromatic ring formed by $X'_3$ and $R'_{39}$), ($R'_{39}$ and $R'_{40}$), ($R'_{40}$ and $R'_{41}$), and ($R'_{41}$ and $R'_{42}$) may form a substituted or unsubstituted aromatic ring, heterocyclic ring or aliphatic ring;

$R_{43}$ is hydrogen, nitro, cyano, alkyl, or aryl;

$n_3$ is 0, 1, or 2;

each of $R''_{38}$, $R''_{39}$, $R''_{40}$, $R''_{41}$, $R''_{42}$, and $R''_{43}$ is hydrogen, halogen, or an organic monovalent residue, and at least one of the combinations ($R''_{39}$ and $R''_{40}$), ($R''_{40}$ and $R''_{41}$), ($R''_{41}$ and $R''_{42}$), and ($R''_{42}$ and $R''_{43}$) may form a substituted or unsubstituted aromatic ring, heterocyclic ring or aliphatic ring;

$X_4$ is a nonmetal atomic group necessary to form a nitrogen-containing heterocyclic ring;

$R_{44}$ is alkyl, substituted alkyl, cyclic alkyl, alkenyl, aralkyl, substituted aralkyl, aryl, or substituted aryl;

$m_3$ is 0, 1, or 2;

$R_{45}$ is substituted or unsubstituted aryl;

$R_{46}$ is a monovalent heterocyclic ring group derived from a heterocyclic ring;

$R_{47}$ is hydrogen, alkyl, substituted or unsubstituted aryl;

$X_5$ is an atomic group necessary to complete pyran, thiapyran, selenapyran, benzopyran, benzothiapyran, benzoselenapyran, naphthopyran, naphthothiapyran, or naphthoselenapyran;

Y is sulfur, oxygen, or selenium;

each of $R_{48}$ and $R_{49}$ is hydrogen, alkyl, alkoxy, substituted or unsubstituted aryl, substituted or unsubstituted styryl, substituted or unsubstituted 4-phenyl-1,3-butadienyl, or a substituted or unsubstituted heterocyclic ring;

$l$ is 0 or 1.

3. An electrophotographic photosensitive member which comprises an electroconductive substrate and an photoconductive film comprising at least one of the azulenium salt compounds represented by the formulae (1)–(9) as shown below;

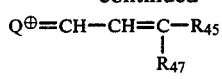

(1)

(2)

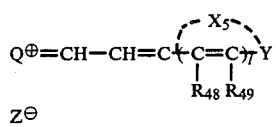

(3)

(4)

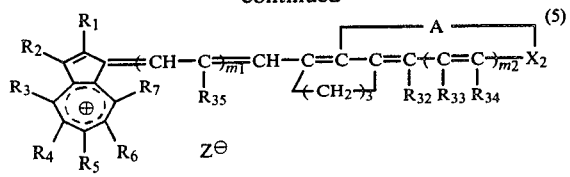
(5)

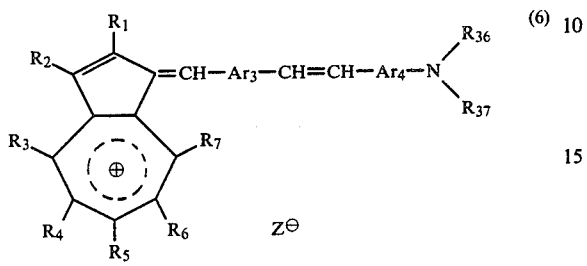
(6)

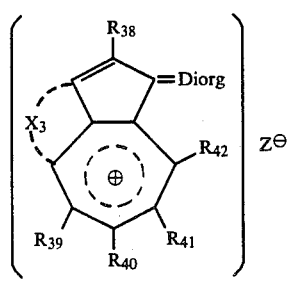
(7)

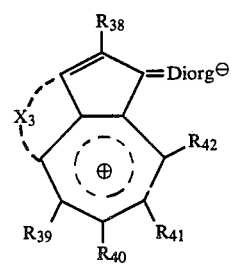
(8)

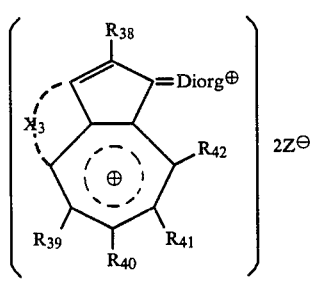
(9)

wherein each of $R_1$, $R_2$, $R_3$, $R_4$, $R_5$, $R_6$, and $R_7$ is hydrogen, halogen, or an organic monovalent residue and at least one of the combinations ($R_1$ and $R_2$), ($R_2$ and $R_3$), ($R_3$ and $R_4$), ($R_4$ and $R_5$), ($R_5$ and $R_6$), and ($R_6$ and $R_7$) may form a substituted or unsubstituted condensed ring;

each of $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ is hydrogen, halogen, alkyl, alkoxy substituted or unsubstituted aryl, substituted or unsubstituted aralkyl, nitro, or acyl, and at least one of the combinations ($R_8$ and $R_9$), ($R_9$ and $R_{10}$), ($R_{10}$ and $R_{11}$), ($R_{11}$ and $R_{12}$), ($R_{12}$ and $R_{13}$), ($R_{14}$ and $R_{15}$), ($R_{15}$ and $R_{16}$), ($R_{16}$ and $R_{17}$), ($R_{17}$ and $R_{18}$), and ($R_{18}$ and $R_{19}$) may form a substituted or unsubstituted condensed ring;

$R_{20}$ is hydrogen, nitro, alkyl, or aryl;

$n_1$ is 0, 1, or 2;

each of $R_{21}$, $R_{22}$, $R_{23}$, $R_{24}$, $R_{25}$, $R_{26}$, $R_{27}$, and $R_{28}$ is hydrogen, halogen, alkyl, alkoxy, hydroxyl, substituted or unsubstituted aryl, substituted or unsubstituted aralkyl, or nitro, and at least one of the combinations ($R_{21}$ and $R_{22}$), ($R_{22}$ and $R_{23}$), ($R_{23}$ and $R_{24}$), ($R_{25}$ and $R_{26}$), ($R_{26}$ and $R_{27}$), and ($R_{27}$ and $R_{28}$) may form a substituted or unsubstituted aromatic ring;

$X_1$ is oxygen, sulfur, or selenium;

$R_{39}$ is hydrogen, nitro, cyano, alkyl, or aryl; $n_2$ is 0, 1, or 2;

each of $R_{30}$ and $R_{31}$ is substituted or unsubstituted alkyl, aryl, or aralkyl, and $R_{30}$ and $R_{31}$ may be joined together with the nitrogen atom to which they are attached to form a ring;

each of $Ar_1$ and $Ar_2$ is substituted or unsubstituted arylene;

each of $R_{32}$, $R_{33}$, and $R_{34}$ is hydrogen, alkyl, alkoxy, substituted or unsubstituted aryl, substituted or unsubstituted styryl, substituted or unsubstituted 4-phenyl-1,3-butadienyl, or a substituted or unsubstituted heterocyclic ring group, and the combination ($R_{32}$ and $R_{33}$) or ($R_{33}$ and $R_{34}$) may form a substituted or unsubstituted benzene ring;

$R_{35}$ is a hydrogen, nitro, alkyl, or aryl;

$X_2$ is oxygen, sulfur, or selenium;

A is an atomic group necessary to complete pyran, thiapyran, selenapyran, benzopyran, benzothiapyran, benzoselenapyrane, naphthopyrane, naphthothiapyran, or naphthoselenapyran which may be substituted;

$m_1$ is 0, 1, or 2;

$m_2$ is 0 or 1;

each of $R_{36}$ and $R_{37}$ is substituted or unsubstituted alkyl, aryl, or aralkyl, and $R_{36}$ and $R_{37}$ may be joined together with the nitrogen atom to which they are attached to form a ring;

each of $Ar_3$ and $Ar_4$ is substituted or unsubstituted arylene;

each of $R_{38}$, $R_{39}$, $R_{40}$, $R_{41}$, and $R_{42}$ is hydrogen, halogen, or an organic monovalent residue;

$X_3$ is an atomic group necessary to form a substituted or unsubstituted 5-, 6-, or 7-membered aromatic ring;

at least one of the combinations ($R_{38}$ and an aromatic ring formed by $X_3$), (an aromatic ring formed by $X_3$ and $R_{39}$), ($R_{39}$ and $R_{40}$), ($R_{40}$ and $R_{41}$), and ($R_{41}$ and $R_{42}$) may form a substituted or unsubstituted aromatic ring, heterocyclic ring or aliphatic ring;

Diorg is an organic divalent residue linked with a double bond;

$Z^\ominus$ is an anionic residue.

4. An electrophotographic photosensitive member according to claim 3, wherein the azulenium salt compounds represented by the formulae (7)-(9) are the compounds represented by the formulae (10)-(20) as shown below:

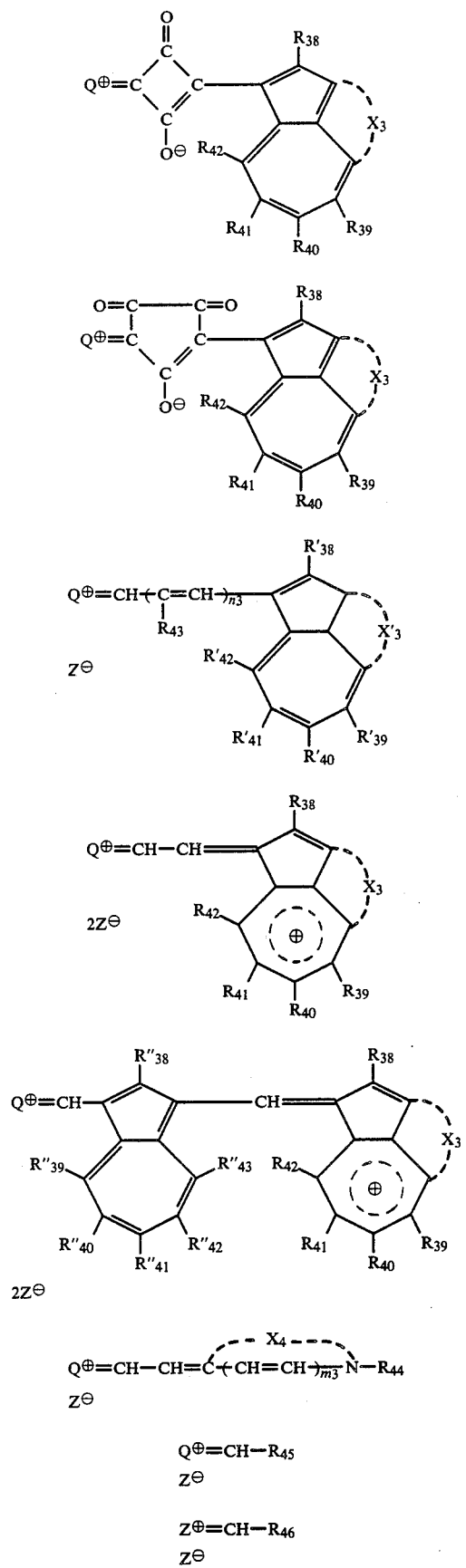

(10) $Q^{\oplus}=CH-CH=C-R_{45}$  (18)
$Z^{\ominus}$    $|$
        $R_{47}$

(19) $Q^{\oplus}=CH-C\equiv C-R_{45}$
$Z^{\ominus}$

(20)
$$Q^{\oplus}=CH-CH-C\overset{\overset{-X_5-}{\frown}}{\underset{R_{48}}{|}}C=C\underset{R_{49}}{\overset{|}{\underset{}{}}})_{\overline{r}}Y$$
$Z^{\ominus}$ wherein
$Q^{\oplus}$ is (structure with $R_{38}$, $R_{39}$, $R_{40}$, $R_{41}$, $R_{42}$, $X_3$, central ⊕)

each of $R_{38}$, $R_{39}$, $R_{40}$, $R_{41}$, and $R_{42}$ is hydrogen, halogen or an organic monovalent residue;

$X_3$ is an atomic group necessary to form a substituted or unsubstituted 5-, 6-, 7-membered aromatic ring;

at least one of the combination ($R_{38}$ and an aromatic ring formed by $X_3$), (an aromatic ring formed by $X_3$ and $R_{39}$), ($R_{39}$ and $R_{40}$), ($R_{40}$ and $R_{41}$), and ($R_{41}$ and $R_{42}$) may form a substituted or unsubstituted aromatic ring, heterocyclic ring or aliphatic ring;

each of $R'_{38}$, $R'_{39}$, $R'_{40}$, $R'_{41}$, and $R'_{42}$ is hydrogen, halogen or an organic monovalent residue;

$X'_3$ is an atomic group necessary to form a substituted or unsubstituted 5-, 6-, 7-membered aromatic ring;

at least one of the combinations ($R_{38}$ and an aromatic ring formed by $X'_3$), (an aromatic ring formed by $X'_3$, and $R'_{39}$), ($R'_{39}$ and $R'_{40}$), ($R'_{40}$ and $R'_{41}$), and ($R'_{41}$ and $R'_{42}$) may form a substituted or unsubstituted aromatic ring, heterocyclic ring or aliphatic ring;

$R_{43}$ is hydrogen, nitro, cyano, alkyl, or aryl;

$n_3$ is 0, 1, or 2;

each of $R''_{38}$, $R''_{39}$, $R''_{40}$, $R''_{41}$, $R''_{42}$, and $R''_{43}$ is hydrogen, halogen, or an organic monovalent residue, and at least one of the combinations ($R''_{39}$ and $R''_{40}$), ($R''_{40}$ and $R''_{41}$), ($R''_{41}$ and $R''_{42}$), ($R''_{42}$ and $R''_{43}$) may form a substituted or unsubstituted aromatic ring, heterocyclic ring or aliphatic ring;

$X_4$ is a nonmetal atomic group necessary to form a nitrogen-containing heterocyclic ring;

$R_{44}$ is alkyl, substituted alkyl, cyclic alkyl, alkenyl, aralkyl, substituted aralkyl, aryl, or substituted aryl;

$m_3$ is 0, 1, or 2;

$R_{45}$ is substituted or unsubstituted aryl;

$R_{46}$ is a monovalent heterocyclic group derived from a heterocyclic ring;

$R_{47}$ is hydrogen, alkyl, substituted or unsubstituted aryl;

$X_5$ in an atomic group necessary to complete pyran, thiapyran, selenapyran, benzopyran, benzothiapyran, benzoselenapyran, naphthapyran, naphthothiapyran, or naphthoselenapyran;

Y is sulfur, oxygen or selenium;

each of $R_{48}$ and $R_{49}$ is hydrogen, alkyl, alkoxy, substituted or unsubstituted aryl, substituted or unsubstituted styryl, substituted or unsubstituted 4-phenyl-1,3-butadienyl, or a substituted or unsubstituted heterocyclic ring;

l is 0 or 1.

5. An electrophotographic photosensitive member according to claim 3, wherein the photoconductive film comprises at least one of the azulenium salt compounds represented by the formulae (1)–(9) and a binder.

6. An electrophotographic photosensitive member according to claim 4, wherein the photosensitive film comprises at least one of the azulenium salt compounds represented by the formulae (10)–(20) and a binder.

7. An electrophotographic photosensitive member according to claim 3, wherein the photoconductive film is a vapor deposition film of at least one of the azulenium salt compounds represented by the formulae (1)–(9).

8. An electrophotographic photosensitive member according to claim 4, wherein the photoconductive film in a vapor deposition film of at least one of the azulenium salt compounds represented by the formulae (10)–(20).

9. An electrophotographic photosensitive member according to claim 3 in which the photoconductive film is used as a charge generation layer and a charge transport layer is provided.

10. An electrophotographic photosensitive member according to claim 9, wherein the charge generation layer is overlaid with the charge transport layer.

11. An electrophotographic photosensitive member according to claim 10, further comprising an intermediate layer between the charge generation layer and the electroconductive substrate.

12. An electrophotographic photosensitive member according to claim 9, wherein the charge generation layer comprises a hole-transporting material and a binder.

13. An electrophotographic photosensitive member according to claim 12, wherein the hole-transporting material is at least one composed selected from the group consisting of aromatic condensed ring compounds, hydrazones, pyrazolines, oxazoles, thiazoles, triaryl methanes, polyarylalkanes, polyphenylamines, and organic photoconductive polymers.

14. An electrophotographic photosensitive member according to claim 13, wherein the hole-transporting material is hydrazones.

15. An electrophotographic photosensitive member according to claim 3, wherein the photoconductive film comprises a photoconductive material and at least one of the azulenium salt compounds represented by the general formulae (1)–(9) as a sensitizer.

16. An electrophotographic photosensitive member according to claim 15, wherein the photoconductive material is at least one compound selected from the group consisting of aromatic condensed ring compounds, hydrazone, pyrazolines, oxazoles, thiazoles, triaryl methanes, polyarylalkanes, polyphenylamines, and organic photoconductive polysters.

17. An electrophotographic photosensitive member according to claim 15, wherein the photoconductive material is an inorganic photoconductive material.

18. An electrophotographic photosensitive member according to claim 15, wherein the azulenium salt compound is at least one of the compounds represented by the formulae (10)–(20).

19. An electrophotographic photosensitive member according to claim 3, wherein a laser beam can be used as an exposure light source.

20. An electrophotographic photosensitive member according to claim 19, wherein the exposure light source is a semiconductor laser.

* * * * *

UNITED STATES PATENT AND TRADEMARK OFFICE
CERTIFICATE OF CORRECTION

PATENT NO. : 4,629,670

DATED : December 16, 1986

INVENTOR(S) : KAZUHARU KATAGIRI, ET AL.

It is certified that error appears in the above-identified patent and that said Letters Patent is hereby corrected as shown below:

On the Title Page:

AT [56] IN THE REFERENCES CITED

Lines 1-3, "Katagini, et al." should read --Katagiri, et al.-- (all three occurrences).

COLUMN 1

Line 16, "3397086 and 3816118" should read --3,397,086 and 3,816,118--.
    Line 17, "discloses" should read --disclose--.
    Line 40, "light absorbing" should read --light-absorbing--.

COLUMN 4

Line 10, "there" should read --they--.
    Line 11, "Ar1 and Ar2" should read --$Ar_1$ and $Ar_2$--.
    Line 35, "Ar3 and Ar4" should read --$Ar_3$ and $Ar_4$--.
    Line 49, "Z- " should read --$Z^{\ominus}$--.
    Line 53, "an" should read --a--.

COLUMN 7

Line 3, "Ar1 and Ar2" should read --$Ar_1$ and $Ar_2$--.
    Line 25, "Ar3 and Ar4" should read --$Ar_3$ and $Ar_4$--.
    Line 39, "$Z^-$ " should read --$Z^{\ominus}$--.
    Line 46, "an" should read --a--.
    Line 59, "2-pheylethyl," should read --2-phenylethyl,--.

UNITED STATES PATENT AND TRADEMARK OFFICE
CERTIFICATE OF CORRECTION

PATENT NO. : 4,629,670

DATED : December 16, 1986

INVENTOR(S) : KAZUHARU KATAGIRI, ET AL.

It is certified that error appears in the above-identified patent and that said Letters Patent is hereby corrected as shown below:

COLUMN 8

Line 1,  "merxapto," should read --mercapto,--.
Line 13, "group e.g." should read --group (e.g.--.
Line 15, "2-ethylhexyl, alkoxy" should read
         --2-ethylhexyl), alkoxy--.
Line 36, "t-butyl, alkoxy" should read
         --t-butyl), alkoxy--.
Line 43, "nitrogenzyl)," should read --nitrobenzyl),--.
Line 51, "n-amyl n-hexyl," should read
         --n-amyl, n-hexyl,--.
Line 52, "t-octyl, substituted" should read
         --t-octyl), substituted--.
Line 63, "Ar1 and Ar2" should read --$Ar_1$ and $Ar_2$--.

COLUMN 9

Line 1,  "butoxy, halogens" should read
         --butoxy), halogens--.
Line 18, "carbozolyl," should read --carbazolyl,--.
Line 42, "pyrroly" should read --pyrrolyl--.
Line 43, "Ar3 and Ar4" should read --$Ar_3$ and $Ar_4$--.
Line 43, "a" should read --an--.
Line 45, "substituted" should read --substituents--.
Line 47, "2-ethykhexyl)," should read --2-ethylhexyl),--.

COLUMN 11

Line 16, 

UNITED STATES PATENT AND TRADEMARK OFFICE
CERTIFICATE OF CORRECTION

PATENT NO. : 4,629,670

DATED : December 16, 1986

INVENTOR(S) : KAZUHARU KATAGIRI, ET AL.

It is certified that error appears in the above-identified patent and that said Letters Patent is hereby corrected as shown below:

COLUMN 11

Line 58, "tolyazo)" should read --tolylazo)--.
Line 63, "methoxybenzene, heterocyclic" should read --methoxybenzene), heterocyclic--.

COLUMN 12

Line 32, "$R_{37}$" and $R_{38}$"" should read --$R_{37}$" to $R_{43}$"--.
Line 58, "carboxy," should read --carboxyl,--.
Line 65, "aromiatic" should read --aromatic--.
Line 67, "methoxybenzene, heterocyclic" should read --methoxybenzene), heterocyclic--.

COLUMN 13

Line 65, "benzofran," should read --benzofuran--.

COLUMN 14

Lines 29-31, Each "pyrane" should read --pyran--.
Line 34, "drogen alkyl" should read --drogen, alkyl--.

COLUMN 18

Line 67, "compounds react" should read --compounds to react--.

COLUMN 23

Line 30, "$CH_3$ ⟨" should read --$CH_3$ ⟨--.

UNITED STATES PATENT AND TRADEMARK OFFICE
CERTIFICATE OF CORRECTION

PATENT NO. : 4,629,670
DATED : December 16, 1986
INVENTOR(S) : KAZUHARU KATAGIRI, ET AL.

It is certified that error appears in the above-identified patent and that said Letters Patent is hereby corrected as shown below:

COULMN 25

Line 34, "CH$_3$ " should read --CH$_3$--.

COL. 28

Line 27, "succeis--" should read --succes- --.

COLUMN 29

Line 9, "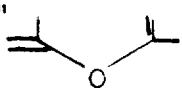" should read --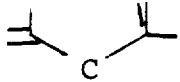-Ch$_3$--.

COLUMN 31

Line 7,   "mixed" should read --mixing--.
    Line 7,   "buthanol," should read --butanol,--.
    Line 9,   "boilding" should read --boiling--.
    Line 20, "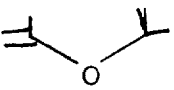" should read --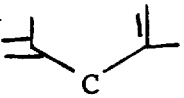--.

COLUMN 32

Line 17, "" should read -- --.

Line 52, "(5)-(12" should read --(5)-(12)--.
    Line 62, "(5)-(13" should read --(5)-(13)--.

COLUMN 35

Line 24, "appropriate solvent." should be deleted.

UNITED STATES PATENT AND TRADEMARK OFFICE
CERTIFICATE OF CORRECTION

PATENT NO. : 4,629,670  Page 5 of 9
DATED : December 16, 1986
INVENTOR(S) : KAZUHARU KATAGIRI, ET AL.

It is certified that error appears in the above-identified patent and that said Letters Patent is hereby corrected as shown below:

COLUMN 38

Line 53, "mixed" should read --mixing--.
    Line 54, "aocohol" should read --alchohol--.

COLUMN 40

Line 40, " 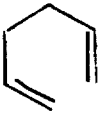 " should read --  --.

COLUMN 45

Line 59, "pages" should read --page--.

COLUMN 46

Line 39, "benzen" should read --benzene--.
    Line 40, "mixed" should read --mixing--.
    Line 57, "devided" should read --divided--.

COLUMN 48

Line 14, "hydrozones" should read --hydrazones--.
    Line 18, "drozone," should read --drazone,--.
    Line 35, "1-pne-" should read --1-phe- --.
    Line 65, "chlorinates" should read --chlorinated--.

COLUMN 49

Line 12, "aluminium," should read --aluminum,--.
    Line 39, "if the this" should read --if this--.

UNITED STATES PATENT AND TRADEMARK OFFICE
CERTIFICATE OF CORRECTION

PATENT NO. : 4,629,670
DATED : December 16, 1986
INVENTOR(S) : KAZUHARU KATAGIRI, ET AL.

It is certified that error appears in the above-identified patent and that said Letters Patent is hereby corrected as shown below:

COLUMN 50

Line 28,   "64 kinds" should read --63 kinds--.
    Line 59,   "64 kinds" should read --63 kinds--.

COLUMN 53

Line 10,   "an" should read --a--.

COLUMN 56

Line 4,   "an" should read --a--.

COLUMN 58

Line 63,   "an" should read --a--.

COLUMN 59

Line 16,   "onan" should read --on an--.
    Line 68,   "discharged" should read --discharge--.

COLUMN 60

Line 39,   "dispersion" should read --dispersing--.

COLUMN 61

Line 57,   "an" should read --a--.

COLUMN 62

Line 15,   "formed ( inyl" should read --formed poly(vinyl--.

UNITED STATES PATENT AND TRADEMARK OFFICE
CERTIFICATE OF CORRECTION

PATENT NO. : 4,629,670

DATED : December 16, 1986

INVENTOR(S) : KAZUHARU KATAGIRI, ET AL.

It is certified that error appears in the above-identified patent and that said Letters Patent is hereby corrected as shown below:

COLUMN 63

Line 8,   "EXAMPLE 135-141" should read --EXAMPLES 135-141--.

Line 29,  "regin" should read --resin--.

COLUMN 64

Line 44,  "an" should read --a--.

COLUMN 65

Line 51,  "in" should read --is--.

Line 54,  "hav-" should read --halv- --.

Line 60,  "Vo: -540v" should read --Vo: -540V--.

COLUMN 66

Lines 66-68,   "Vo +420v" should read --Vo: +420V--.
                   VK 78%                     VK: 78%
                   E½45.8 lux·sec        E½: 45.8 lux·sec

COLUMN 67

Lines 9-11,   "Vo +490V" should read --Vo: +490V--.
                   VK 82%                     VK: 82%
                   E½29.8 lux·sec        E½: 29.8 lux·sec Line 37,  "an" should read --a--.

Lines 53-55,  "Vo +430V" should read --Vo: +430V--.
                   VK 83%                     VK: 83%
                   E½ 7.5 lux·sec        E½: 7.5 lux·sec

UNITED STATES PATENT AND TRADEMARK OFFICE
CERTIFICATE OF CORRECTION

PATENT NO. : 4,629,670

DATED : December 16, 1986

INVENTOR(S) : KAZUHARU KATAGIRI, ET AL.

It is certified that error appears in the above-identified patent and that said Letters Patent is hereby corrected as shown below:

COLUMN 68

Lines 19-21, "Vo -545V" should read --Vo: -545V--.
VK 87%                          VK: 87%
E½3.4 lux.sec                   E½: 3.4 lux.sec Lines 57-59, "Vo -540V" should read --Vo: -540V--.
VK 87%                          VK: 87%
E½2.0 microjoule/cm$^2$         E½: 2.0 microjoule/cm$^2$

COLUMN 71

Line 53, "substitued" should read --substituted--.

COLUMN 73

Line 11, " $\begin{array}{c} X_5 \\ C+C \end{array}$ " should read -- $\begin{array}{c} X_5 \\ C+C \end{array}$ --.

COLUMN 75

Line 62, "alkoxy" should read --alkoxy,--.
Line 65, "(R$_8$and" should read --R$_8$ and--.

COLUMN 76

Line 36, "benzoselenapyrane, naphthopyrane," should read --benzoselenapyran, naphthopyran,--.

UNITED STATES PATENT AND TRADEMARK OFFICE
CERTIFICATE OF CORRECTION

PATENT NO.   : 4,629,670
DATED        : December 16, 1986
INVENTOR(S)  : KAZUHARU KATAGIRI, ET AL.

It is certified that error appears in the above-identified patent and that said Letters Patent is hereby corrected as shown below:

COLUMN 78

Line 31,    "6-, 7-membered" should read --6-, or 7-membered--.

Line 40,    "6-, 7-membered" should read --6-, or 7-membered--.

COLUMN 79

Line 1,    "naphthapyran," should read --naphthopyran,--.
    Line 30,    "3 in" should read --3, in--.

COLUMN 80

Line 7,    "composed" should read --compound--.
    Line 26,    "polyster" should read --polymers--.

Signed and Sealed this

Eleventh Day of August, 1987

*Attest:*

DONALD J. QUIGG

*Attesting Officer*      *Commissioner of Patents and Trademarks*